United States Patent
Keller

(10) Patent No.: US 10,869,653 B2
(45) Date of Patent: Dec. 22, 2020

(54) TISSUE SAMPLE HOLDER WITH BULK TISSUE COLLECTION FEATURE

(71) Applicant: Devicor Medical Products, Inc., Cincinnati, OH (US)

(72) Inventor: Bryan R. Keller, Loveland, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 316 days.

(21) Appl. No.: 15/965,203

(22) Filed: Apr. 27, 2018

(65) Prior Publication Data

US 2018/0242959 A1 Aug. 30, 2018
US 2019/0328372 A9 Oct. 31, 2019

Related U.S. Application Data

(63) Continuation of application No. PCT/US2016/059411, filed on Oct. 28, 2016.

(60) Provisional application No. 62/248,441, filed on Oct. 30, 2015.

(51) Int. Cl.
| | |
|---|---|
| *A61B 5/00* | (2006.01) |
| *A61B 10/02* | (2006.01) |
| *A61M 1/00* | (2006.01) |

(52) U.S. Cl.
CPC ...... *A61B 10/0275* (2013.01); *A61B 10/0283* (2013.01); *A61M 1/0056* (2013.01); *A61B 2010/0208* (2013.01); *A61B 2010/0225* (2013.01)

(58) Field of Classification Search
CPC ............ A61B 10/0096; A61B 10/0275; A61B 10/0283; A61B 2010/0225; A61M 1/0056
See application file for complete search history.

(56) References Cited

U.S. PATENT DOCUMENTS

| | | | |
|---|---|---|---|
| 5,526,822 A | 6/1996 | Burbank et al. | |
| 5,928,164 A | 7/1999 | Burbank et al. | |
| 6,017,316 A | 1/2000 | Ritchart et al. | |
| 6,086,544 A | 4/2000 | Hibner et al. | |

(Continued)

FOREIGN PATENT DOCUMENTS

| | | |
|---|---|---|
| CN | 104703549 | 6/2015 |
| WO | WO 2013/192606 A1 | 12/2013 |

(Continued)

OTHER PUBLICATIONS

Hahn, M., et al., "Diagnostic Primer: Vacuum-Assisted Breast Biopsy with Mammotome®" Devicor Medical Germany GmbH, Nov. 11, 2012, published in Germany by Springer Medizin Verlag, copyright 2013, 130 pgs.

(Continued)

*Primary Examiner* — Max F Hindenburg
(74) *Attorney, Agent, or Firm* — Frost Brown Todd LLC

(57) ABSTRACT

A biopsy device including a body, a needle, a cutter, and a tissue sample holder. The needle extends distally from the body. The cutter is longitudinally translatable relative to the needle and defines a cutter lumen. The tissue sample holder includes an outer cup or cover, a rotatable member, a tissue receiving tray, and a bulk cup assembly. The rotatable member defines a plurality of passages and a first cylindrical portion. Each strip of the plurality of strips are insertable into a corresponding passage of the plurality of passages. The bulk cup assembly is insertable into the first cylindrical portion of the rotatable member.

20 Claims, 36 Drawing Sheets

(56) References Cited

U.S. PATENT DOCUMENTS

| | | | |
|---|---|---|---|
| 6,162,187 A | 12/2000 | Buzzard et al. |
| 6,228,055 B1 | 5/2001 | Foerster et al. |
| 6,371,904 B1 | 4/2002 | Sirimanne et al. |
| 6,432,065 B1 | 8/2002 | Burdorff et al. |
| 6,444,174 B1 | 9/2002 | Lascombes |
| 6,626,849 B2 | 9/2003 | Huitema et al. |
| 6,752,768 B2 | 6/2004 | Burdorff et al. |
| 6,993,375 B2 | 1/2006 | Burbank et al. |
| 6,996,433 B2 | 2/2006 | Burbank et al. |
| 7,044,957 B2 | 5/2006 | Foerster et al. |
| 7,047,063 B2 | 5/2006 | Burbank et al. |
| 7,229,417 B2 | 6/2007 | Foerster et al. |
| 7,442,171 B2 | 10/2008 | Stephens et al. |
| 7,465,279 B2 | 12/2008 | Beckman et al. |
| 7,575,556 B2 | 8/2009 | Speeg et al. |
| 7,648,466 B2 | 1/2010 | Stephens et al. |
| 7,794,409 B2 | 9/2010 | Damarati |
| 7,837,632 B2 | 11/2010 | Stephens et al. |
| 7,854,706 B2 | 12/2010 | Hibner |
| 7,914,464 B2 | 3/2011 | Burdorff et al. |
| 7,918,803 B2 | 4/2011 | Ritchart et al. |
| 7,918,804 B2 | 4/2011 | Monson et al. |
| 7,938,786 B2 | 5/2011 | Ritchie et al. |
| 8,083,687 B2 | 12/2011 | Parihar |
| 8,118,755 B2 | 2/2012 | Hibner et al. |
| 8,206,316 B2 | 6/2012 | Hibner et al. |
| 8,241,226 B2 | 8/2012 | Hibner et al. |
| 8,251,916 B2 | 8/2012 | Speeg et al. |
| 8,371,443 B2 | 2/2013 | Nock et al. |
| 8,454,531 B2 | 6/2013 | Speeg et al. |
| 8,532,747 B2 | 9/2013 | Nock et al. |
| 8,532,748 B2 | 9/2013 | Leimbach et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,938,285 B2 | 1/2015 | Fiebig et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 9,486,186 B2 | 11/2016 | Fiebig et al. |
| 9,724,076 B2 | 8/2017 | Fiebig et al. |
| 9,877,706 B2 | 1/2018 | Speeg et al. |
| 10,064,607 B2 | 9/2018 | Keller et al. |
| 2006/0074345 A1 | 4/2006 | Hibner |
| 2008/0004545 A1 | 1/2008 | Garrison |
| 2009/0131821 A1 | 5/2009 | Speeg et al. |
| 2009/0209854 A1 | 8/2009 | Parihar et al. |
| 2010/0152610 A1 | 6/2010 | Parihar et al. |
| 2010/0160819 A1 | 6/2010 | Parihar et al. |
| 2011/0071391 A1 | 3/2011 | Speeg |
| 2011/0071423 A1 | 3/2011 | Speeg et al. |
| 2012/0283563 A1 | 11/2012 | Moore et al. |
| 2013/0324882 A1 | 12/2013 | Mescher |
| 2016/0183928 A1 | 6/2016 | Speeg et al. |

FOREIGN PATENT DOCUMENTS

| | | |
|---|---|---|
| WO | WO 2013/192607 A1 | 12/2013 |
| WO | WO 2014/151603 A1 | 9/2014 |

OTHER PUBLICATIONS

International Search Report and Written Opinion dated Jan. 26, 2017 for Application No. PCT/US2016/059411, 9 pgs.

U.S. Appl. No. 61/566,793, entitled "Biopsy Device With Slide-In Probe," filed Dec. 5, 2011.

U.S. Appl. No. 61/682,418, entitled "Biopsy System with Graphical User Interface," filed Aug. 13, 2012.

U.S. Appl. No. 61/727,889, entitled "Biopsy System with Graphical User Interface," filed Nov. 19, 2012.

U.S. Appl. No. 61/771,212, entitled "Biopsy System with Graphical User Interface," filed Mar. 1, 2013.

U.S. Appl. No. 62/248,441, entitled "Tissue Sample Holder with Bulk Tissue Collection Feature," filed Oct. 30, 2015.

Chinese Office Action dated Jun. 24, 2020 for Application No. 201680063544.X, 5 pages.

TISSUE SAMPLE HOLDER WITH BULK TISSUE COLLECTION FEATURE

FIELD OF THE INVENTION

This invention is in the field of obtaining and collecting tissue samples during biopsy procedures.

BACKGROUND OF THE INVENTION

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample may be analyzed at a lab (e.g. a pathology lab, biomedical lab, etc.) that is set up to perform the appropriate tests (such as histological).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

The state of the art for breast biopsy is vacuum-assisted breast biopsy. A current textbook in this area is "Vacuum-Assisted Breast Biopsy with Mammotome®," available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Biopsy devices may be used under ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used. The following briefly describes ultrasound image guided biopsy procedures, stereotactic guided biopsy procedures and MRI guided biopsy procedures.

In an ultrasound image guided breast biopsy procedure, the operator may position an ultrasound transducer on the patient's breast and maneuver the transducer while viewing an ultrasound image display screen to locate suspicious tissue in the patient's breast. Once the operator locates the suspicious tissue, the operator may anesthetize the target region of the breast. Once the breast has been anesthetized, the operator may create an initial incision using a scalpel at a location on the exterior of the breast offset from the transducer. A needle of a breast biopsy probe disposed coaxially within an introducer cannula is then inserted into the breast through the initial incision. The operator continues to hold the ultrasound transducer with one hand while maneuvering the biopsy probe with the other hand. While viewing the ultrasound image on the display screen, the operator guides the needle to a position adjacent to the suspicious tissue. A cutter within the needle of the probe is used to remove tissue which is then conveyed either to a manual pick-up location on the breast biopsy device or to a tissue sample chamber. The needle of the breast biopsy device is then removed, leaving the introducer cannula disposed within the breast. The introducer cannula may then be used to introduce a biopsy marker cannula for deploying a biopsy site marker at the biopsy site. Once a marker has been deployed at the biopsy site, the biopsy marker cannula and the introducer cannula are both removed from the breast and the incision is closed using a medically acceptable way to close breaks in the skin.

In a stereotactic image guided breast biopsy procedure, the patient is first positioned relative to x-ray equipment, which includes a breast localization assembly. In some procedures, the patient is oriented in a prone position, with the patient lying face down on a procedure table with at least one breast hanging pendulously through an aperture in the procedure table. The breast is then compressed between a compression paddle and an x-ray receptor of a localization assembly that is positioned under the procedure table. A breast biopsy device is positioned on an automatic guide device in front of the compression paddle and between the breast and an x-ray source. Once positioning of the patient and localization of the breast are complete, a scout image is acquired with the x-ray receptor in a zero-degree angular position (i.e., the x-rays are emitted along an axis normal relative to the x-ray receptor). If the scout image indicates that the patient has been positioned in a desired position, the procedure may proceed with the acquisition of stereotactic image pairs. Stereotactic image pairs are acquired by orienting the x-ray source at various complementary angular positions relative to the x-ray receptor (e.g., +15° and −15°), with at least one x-ray image acquired at each position.

Further in the stereotactic image guided breast biopsy procedure, once a suitable stereotactic image pair is acquired, an operator may identify a target site where biopsy sampling is desired by examining the stereotactic image pair. The target site is marked on each stereotactic image and a precise location of the target site on a Cartesian coordinate system is computed using an image processing module. The computed location of the target site is then communicated to the automatic guide device. The automatic guide device is responsive to this information to position the breast biopsy probe into a position that aligns with the target site. With the breast biopsy device positioned, an operator may then fire a needle of the biopsy probe into the breast of the patient, thereby positioning the needle at the target site. A cutter within the needle of the probe is used to remove tissue, which is then conveyed either to a manual pick-up location on the breast biopsy device or to a tissue sample chamber. After the biopsy tissue is removed, a biopsy marker cannula is inserted into the needle and is used to deploy a biopsy site marker at the biopsy site. Once a marker has been deployed at the biopsy site, the needle is removed from the breast and the incision is closed using a medically acceptable way to close breaks in the skin.

In an MRI guided breast biopsy procedure, after the patient is properly positioned on the table and a targeting device (e.g., a grid and cube combination or a pillar, post and cradle support combination) has been deployed and used, a baseline MRI image is taken to verify the target location. After that, a scalpel is used to incise the skin of the breast. Next, an assembly, formed by an obturator disposed in a sleeve, is inserted through the incision to penetrate the breast tissue under the skin. In some acceptable surgical techniques, the obturator is removed and an imaging rod is inserted into the sleeve in place of the obturator. An imaging rod is defined simply as an appropriately shaped rod that includes a feature that is detectable by an imaging technique being used for the biopsy procedure. The MRI image of the imaging rod is used to locate the site to which the sleeve/obturator assembly has penetrated. In some other acceptable surgical techniques, the obturator cooperates with the breast tissue to provide a visually observable artifact in an MRI image. With both of these techniques, after the location within the breast where the biopsy is to be taken is confirmed, the obturator or the imaging rod is removed.

Further in the MRI guided breast biopsy procedure, after the obturator or imaging rod has been removed, it is replaced in the sleeve with the needle of a breast biopsy probe. A cutter within the needle of the probe is used to remove tissue, which is then conveyed either to a manual pick up location on the breast biopsy device or to a breast biopsy device sample chamber. After the biopsy tissue is removed, a biopsy marker cannula is inserted into the needle and is used to deploy a biopsy site marker at the biopsy site. The needle is then removed from the sleeve. Optionally, the imaging rod or the obturator is put back into the breast for reimaging of the biopsy site. Then the imaging rod or obturator and the sleeve are removed.

Known biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015; U.S. Pat. No. 9,095,326, entitled "Biopsy System with Vacuum Control Module," issued Aug. 4, 2015 and U.S. Pat. No. 9,326,755, entitled "Biopsy Device Tissue Sample Holder with Bulk Chamber and Pathology Chamber," issued May 3, 2016. The disclosure of each of the above-cited U.S. patents is incorporated by reference herein.

Additionally known biopsy devices and biopsy system components are disclosed in U.S. Pub. No. 2006/0074345, entitled "Biopsy Apparatus and Method," published Apr. 6, 2006 and now abandoned; U.S. Pub. No. 2008/0214955, entitled "Presentation of Biopsy Sample by Biopsy Device," published Sep. 4, 2008; U.S. Patent Pub. No. 2009/0131821, entitled "Graphical User Interface For Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; U.S. Pub. No. 2013/0144188, entitled "Biopsy Device With Slide-In Probe," published Jun. 6, 2013; and U.S. Pub. No. 2013/0324882, entitled "Control for Biopsy Device," published Dec. 5, 2013. The disclosure of each of the above-cited U.S. patent application Publications is incorporated by reference herein.

U.S. Pub. No. 2014/0275999, entitled "Biopsy device" published Sep. 18, 2014, and U.S. Pub. No. 2016/0183928, entitled "Biopsy Device," published Jun. 30, 2016, both describe some aspect of a biopsy device including a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

At several steps during tissue processing using conventional techniques and instruments, it may be necessary to manually manipulate the tissue. This manual manipulation may take time and introduce the possibility of human error causing mistakes during the processing of tissue. Any and all mistakes during the processing of tissue may make the pathological examination of the tissue much more problematic to achieve the desired goal of having an accurate diagnosis. Thus, it is understood that a desired goal of modern tissue processing is the reduction of the requirement that tissue be manually manipulated.

International Pat. Pub. No. WO 2013/192606, entitled "Biopsy Tissue Sample Transport Device and Method of Using Thereof," published on Dec. 27, 2013, describes a biopsy tissue sample transport device and method of using the same including a tissue storage assembly having a sample container, having a holding structure to hold a tissue sample, the holding structure having a sample access opening formed in a sidewall; a housing that receives the tissue storage assembly, the housing comprising an assembly insertion opening through which the tissue storage assembly is inserted into the housing; a sealing member configured to engage and substantially seal the sample access opening of the holding structure of the sample container of the tissue storage assembly; and a lid to engage and substantially seal the assembly insertion opening of the housing.

International Pat. Pub. No. WO 2013/192607, entitled "Tissue Sample Container and Methods," published on Dec. 27, 2013, describes a tissue sample container including a base having a plurality of sample holding sections, which are configured to receive a plurality of tissue samples in a given orientation and are demarcated by section walls; and a lid configured to sealingly engage the base. The sample holding sections are sized and shaped to correspond to a specific tissue sample size and shape such that the base in cooperation with the section walls, maintain the given orientation and identity of the tissue samples within respective sample holding sections.

International Pat. Pub. No. WO 2014/151603, entitled "Biopsy Device," published on Sep. 25, 2014, describes a biopsy device that includes a probe, a holster, and a tissue sample holder for collecting tissue samples. The probe includes a needle and a hollow cutter. The tissue sample holder includes a housing having a plurality of chambers that are configured to receive a plurality of strips connected by at least one flexible member. The flexible member is configured to permit the strips to pivot relative to each other such that the strips can shift between a flat configuration and an arcuate configuration. The tissue sample holder is rotatable to successively index each chamber to the cutter lumen such that tissue samples may be collected in the strips. The strips may be removed from the tissue sample holder and placed in a tissue sample holder container for imaging of tissue samples.

While several systems and methods have been made and used for obtaining and processing a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
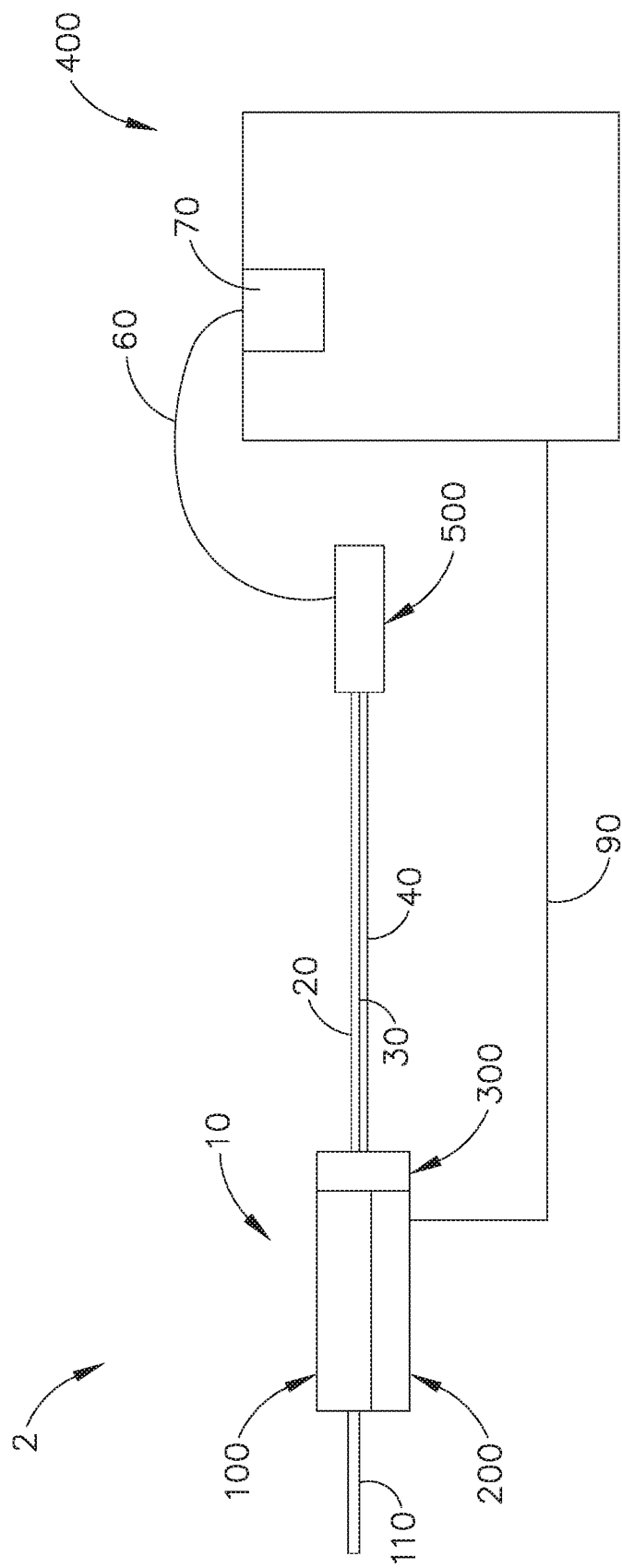
FIG. 1 depicts a schematic view of an exemplary biopsy system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

SUMMARY OF THE INVENTION

One aspect of this invention is a biopsy device comprising: a body; a needle extending distally from the body; a cutter longitudinally translatable relative to the needle, wherein the cutter defines a cutter lumen; and a tissue sample holder comprising, an outer cup or cover, a rotatable member, wherein the rotatable member defines a plurality of passages and a first cylindrical portion, a tissue receiving tray comprising a plurality of strips, wherein each strip of the plurality of strips are insertable into a corresponding passage of the plurality of passages, and a bulk cup assembly, wherein the bulk cup assembly is insertable into the first cylindrical portion of the rotatable member.

DETAILED DESCRIPTION OF THE INVENTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

The following "Parts List" giving the number and name of each part shown in the accompanying drawings is included to guide the reader:

| Reference Number | Part |
|---|---|
| 2 | Biopsy System |
| 10 | Biopsy Device |
| 20 | Tube |
| 30 | Tube |
| 40 | Tube |
| 46 | Tube |
| 70 | Vacuum Canister |
| 90 | Cable |
| 100 | Probe |
| 102 | Top Housing |
| 104 | Resilient Tabs |
| 106 | Chassis |
| 107 | Opening |
| 110 | Needle |
| 112 | Tissue Piercing Tip |
| 113 | Cannula |
| 114 | Lateral Aperture |
| 115 | Removable Cover |
| 116 | Thumbwheel |
| 117 | Resiliently biased latch |
| 118 | Annular Flange |
| 120 | Hub Member |
| 122 | Rotatable Member |
| 124 | Hollow Interior |
| 126 | Port |
| 130 | Gears |
| 140 | Gears |
| 142 | Nut |
| 144 | Internal Threading |
| 150 | Cutter |
| 151 | Lumen |
| 152 | Sharp Distal Edge |
| 160 | Overmold |
| 162 | Threading |
| 164 | Hexagonal Flats |
| 166 | Smooth and Cylindraceous Distal Portion |
| 170 | Sealing Member |
| 172 | Longitudinally Extending Cutter Seal |
| 174 | Opening |
| 176 | Opening |
| 178 | Port |
| 180 | Rotation Member |
| 182 | Gear |
| 184 | Grasping Feature |
| 190 | Longitudinal Wall |
| 192 | Second Lumen |
| 194 | Plurality of Openings |
| 200 | Holster |
| 202 | Top Housing Cover for Holster |
| 204 | Side Panels |
| 206 | Housing Base |
| 208 | Prongs |
| 210 | Knob |
| 212 | Gears |
| 222 | Fork |
| 224 | Prongs |
| 226 | Firing Rod |
| 230 | Gears |
| 240 | Gear |
| 400 | Vacuum Control Module |
| 300 | TSH |
| 302 | Transparent Outer Cup for Sample Chamber |
| 310 | Rotatable Member |
| 312 | Passages |
| 313 | Passage |
| 314 | Recesses |
| 315 | Recess |
| 316 | Shelves |
| 320 | Central Shaft |
| 330 | Tissue Receiving Trays |
| 332 | Grip |
| 334 | Proximal Wall |
| 336 | Pinched Regions |
| 338 | Numerical Indicia |
| 340 | Strips |
| 342 | Floor |
| 343 | Wiper Seal |
| 344 | Pair of Sidewalls |
| 345 | Openings |
| 346 | Chamber |
| 348 | Opening |
| 349 | Wiper Seal |
| 360 | Plug |
| 362 | Grip |
| 364 | Body |
| 366 | Seal |
| 368 | Seal |
| 400 | Vacuum Control Mod. |

-continued

| Reference Number | Part |
|---|---|
| 500 | Alt Tissue Sample Holder |
| 502 | Transparent Outer Cup for Sample Chamber |
| 510 | Rotatable Member |
| 511 | Vacuum Passage |
| 512 | Passages |
| 513 | Passage |
| 514 | Lateral Recess |
| 515 | Recess |
| 516 | Shelves |
| 517 | Shelf |
| 518 | Curved Portion |
| 519 | Opening |
| 520 | Central Shaft |
| 522 | First Cylindrical Portion |
| 524 | Second Cylindrical Portion |
| 530 | Tissue Receiving Trays |
| 532 | Grip |
| 534 | Proximal Wall |
| 536 | Pinched Regions |
| 538 | Numerical Indicia |
| 540 | Plurality of Strips |
| 542 | Floor |
| 543 | Wiper Seal |
| 544 | Pair of Sidewalls |
| 545 | Plurality of Openings |
| 546 | Tissue Sample Chamber |
| 548 | Opening |
| 549 | Wiper Seal |
| 600 | Bulk Cup Assembly |
| 610 | Body |
| 612 | Sample Cavity |
| 614 | Removal Knob |
| 616 | Graphical Indicator |
| 618 | Seal |
| 630 | Filter |
| 631 | End Portion |
| 632 | First Member |
| 634 | Fluid Chamber |
| 636 | Fluid Openings |
| 638 | Second Member |
| 640 | Vacuum Chamber |
| 642 | Vacuum Openings |
| 660 | Removable Top |
| 662 | Engagement Member |
| 664 | Shelf |
| 666 | Tissue Communication Port |
| 667 | Rectangular Opening |
| 668 | Raised Surface |
| 700 | Alt. Bulk Cup Assy. |
| 710 | Body |
| 712 | Sample Cavity |
| 714 | Removal Knob |
| 716 | Graphical Indicator |
| 718 | Seal |
| 719 | Opening |
| 730 | Filter |
| 731 | End Portion |
| 732 | First Member |
| 734 | Fluid Chamber |
| 736 | Fluid Openings |
| 738 | Second Member |
| 740 | Vacuum Chamber |
| 742 | Vacuum Openings |
| 750 | First Attachment Member |
| 752 | Tooth |
| 754 | Second Attachment Member |
| 766 | Tissue Communication Port |
| 767 | Rectangular Opening |
| 768 | Raised Surface |
| 800 | Alt. Bulk Cup Assembly |
| 810 | Body |
| 812 | Sample Cavity |
| 814 | Removal Knob |
| 816 | Graphical Indicator |
| 818 | Seal |

-continued

| Reference Number | Part |
|---|---|
| 819 | Opening |
| 830 | Filter |
| 831 | End Portion |
| 832 | First Member |
| 834 | Fluid Chamber |
| 836 | Fluid Openings |
| 838 | Second Member |
| 840 | Vacuum Chamber |
| 842 | Vacuum Openings |
| 850 | First Attachment Member |
| 852 | Tooth |
| 854 | Second Attachment Member |
| 866 | Tissue Communication Port |
| 867 | Rectangular Opening |
| 868 | Raised Surface |
| 1000 | Alt. Tissue Sample Holder |
| 1002 | Transparent Outer Cup |
| 1010 | Rotatable Member |
| 1011 | Vacuum Passage |
| 1012 | Passages |
| 1013 | Passage |
| 1014 | Lateral Recess |
| 1015 | Recess |
| 1016 | Shelves |
| 1017 | Shelf |
| 1018 | Open Proximal End |
| 1020 | Central Shaft |
| 1022 | First Cylindrical Portion |
| 1024 | Second Cylindrical Portion |
| 1030 | Tissue Receiving Trays |
| 1032 | Grip |
| 1034 | Proximal Wall |
| 1036 | Pinched Regions |
| 1038 | Numerical Indicia |
| 1040 | Plurality of Strips |
| 1042 | Floor |
| 1043 | Wiper Seal |
| 1044 | Pair of Sidewalls |
| 1045 | Plurality of Openings |
| 1046 | Tissue Sample Chamber |
| 1048 | Opening |
| 1049 | Wiper Seal |
| 1100 | Bulk Cup Assembly |
| 1110 | Body |
| 1112 | Sample Cavity |
| 1114 | Removal Knob |
| 1116 | Graphical Indicator |
| 1118 | Seal |
| 1130 | Filter |
| 1131 | End Portion |
| 1132 | First Member |
| 1134 | Fluid Chamber |
| 1136 | Fluid Openings |
| 1138 | Second Member |
| 1140 | Vacuum Chamber |
| 1142 | Vacuum Openings |
| 1150 | First Attachment Member |
| 1152 | Tooth |
| 1154 | Second Attachment Member |
| 1166 | Tissue Communication Port |
| 1167 | Open Distal End |
| 1168 | Cylindrical Portion |
| 1169 | Lateral Tissue Receiving Portion |
| 1170 | Opening |

Figure 2:
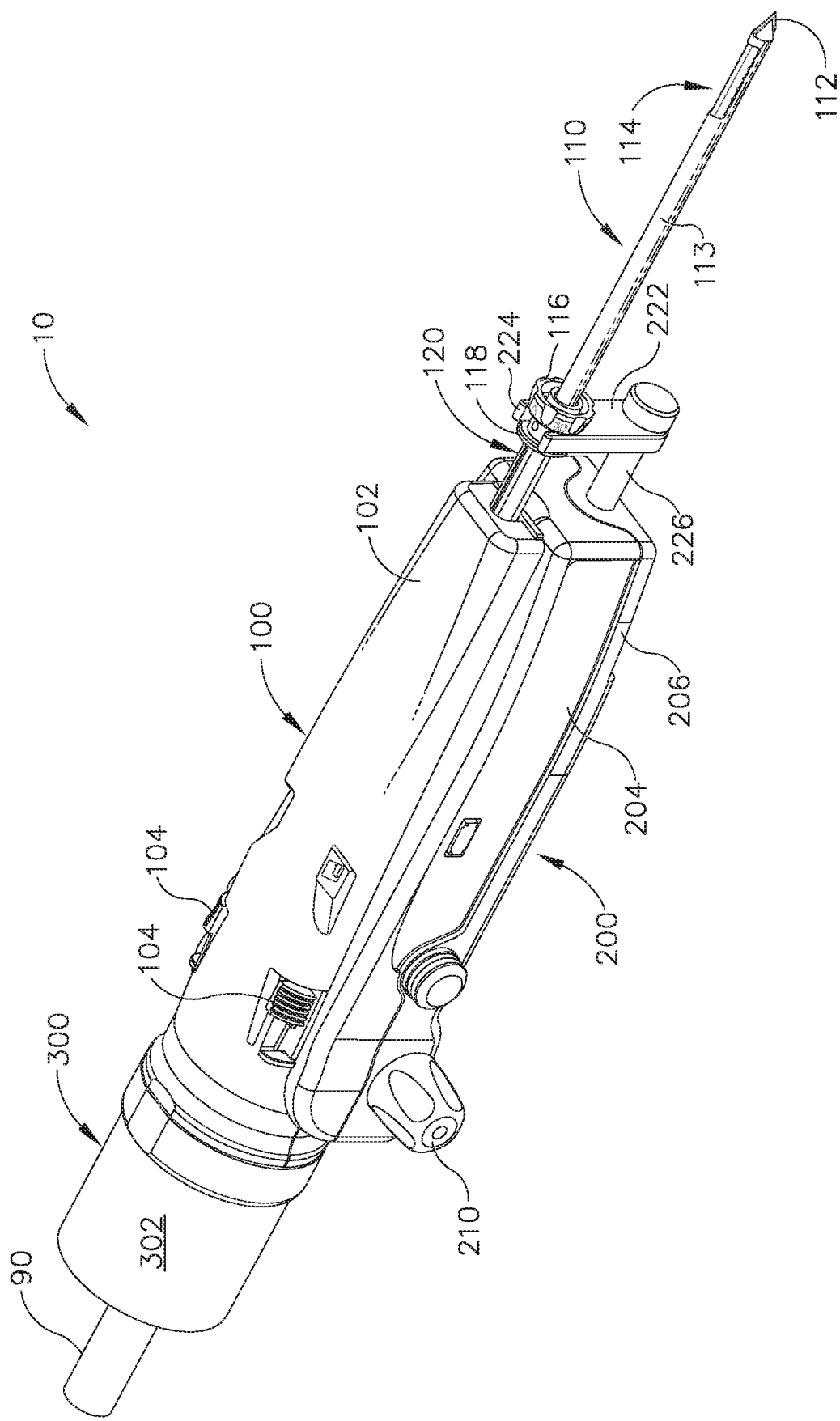
FIG. 2 depicts a perspective view of an exemplary biopsy device of the biopsy system of FIG. 1, including an exemplary probe coupled with an exemplary holster.
Figure 3:
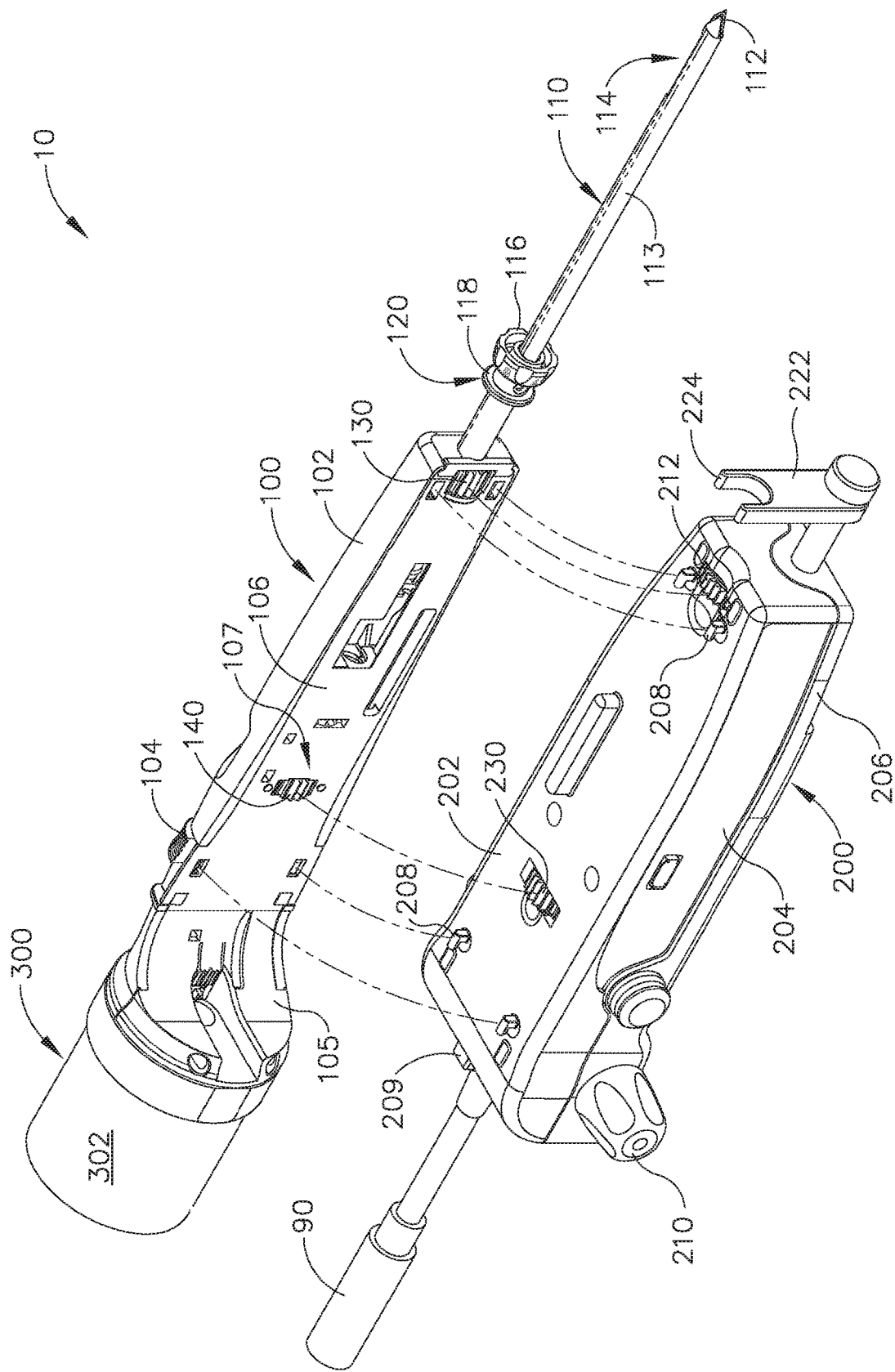
FIG. 3 depicts a perspective view of the biopsy device of FIG. 2, with the probe decoupled from the holster.

FIG. 1 depicts an exemplary biopsy system (2) comprising a biopsy device (10) and a vacuum control module (400). Biopsy device (10) of this example comprises a probe (100) and a holster (200), as shown in FIGS. 2-3. A needle (110) extends distally from probe (100), and is inserted into a patient's tissue to obtain tissue samples. These tissue samples are deposited in a tissue sample holder (300) at the proximal end of probe (100), as will also be described in greater detail below.

It should also be understood that the use of the term "holster" herein should not be read as requiring any portion of probe (100) to be inserted into any portion of holster (200). In the present example, holster (200) includes a set of prongs (208) that are received by the chassis (106) of probe (100) to releasably secure probe (100) to holster (200). In particular, probe (100) is first positioned on top of holster (200), just proximal to its final position relative to holster (200); then probe (100) is slid distally to fully engage prongs (208). Probe (100) also includes a set of resilient tabs (104) that may be pressed inwardly to disengage prongs (208), such that a user may simultaneously depress both tabs (104) then pull probe (100) rearwardly and away from holster (200) to decouple probe (100) from holster (200). Of course, a variety of other types of structures, components, features, etc. (e.g., bayonet mounts, latches, clamps, clips, snap fittings, etc.) may be used to provide removable coupling of probe (100) and holster (200). Furthermore, in some biopsy devices (10), probe (100) and holster (200) may be of unitary or integral construction, such that the two components cannot be separated. By way of example only, in versions where probe (100) and holster (200) are provided as separable components, probe (100) may be provided as a disposable component, while holster (200) may be provided as a reusable component. Still other suitable structural and functional relationships between probe (100) and holster (200) will be apparent to those of ordinary skill in the art in view of the teachings herein.

Some variations of biopsy device (10) may include one or more sensors (not shown), in probe (100) and/or in holster (200), that is/are configured to detect when probe (100) is coupled with holster (200). Such sensors or other features may further be configured to permit only certain types of probes (100) and holsters (200) to be coupled together. In addition or in the alternative, such sensors may be configured to disable one or more functions of probes (100) and/or holsters (200) until a suitable probe (100) and holster (200) are coupled together. In one merely illustrative example, probe (100) includes a magnet (not shown) that is detected by a Hall effect sensor (not shown) or some other type of sensor in holster (200) when probe (100) is coupled with holster (200). As yet another merely illustrative example, coupling of probe (100) with holster (200) may be detected using physical contact between conductive surfaces or electrodes, using RFID technology, and/or in numerous other ways as will be apparent to those of ordinary skill in the art in view of the teachings herein. Of course, such sensors and features may be varied or omitted as desired.

Biopsy device (10) of the present example is configured to mount to a table or fixture, and be used under stereotactic guidance. Of course, biopsy device (10) may instead be used under ultrasound guidance, MRI guidance, PEM guidance, BSGI guidance, or otherwise. It should also be understood that biopsy device (10) may be sized and configured such that biopsy device (10) may be operated by a single hand of a user. In particular, a user may grasp biopsy device (10), insert needle (110) into a patient's breast, and collect one or a plurality of tissue samples from within the patient's breast, all with just using a single hand. Alternatively, a user may grasp biopsy device (10) with more than one hand and/or with any desired assistance. In some settings, the user may capture a plurality of tissue samples with just a single insertion of needle (110) into the patient's breast. Such tissue samples may be deposited in tissue sample holder (300), and later retrieved from tissue sample holder (300) for analysis. While examples described herein often refer to the acquisition of biopsy samples from a patient's breast, it should be understood that biopsy device (10) may be used in a variety of other procedures for a variety of other purposes and in a variety of other parts of a patient's anatomy (e.g., prostate, thyroid, etc.). Various exemplary components, features, configurations, and operabilities of biopsy device (10) will be described in greater detail below; while other suitable components, features, configurations, and operabilities will be apparent to those of ordinary skill in the art in view of the teachings herein.

As shown in FIG. 3, holster (200) of the present example includes a top housing cover (202), side panels (204), and a housing base (206), which are fixedly secured together. Gears (212, 230) are exposed through top housing cover (202), and mesh with gears (130, 140) of probe (100) when probe (100) and holster (200) are coupled together. In particular, gears (230, 140) drive the actuation assembly of a cutter (150) within needle (110); while gears (212, 130) are employed to rotate needle (110). Gear (240) is located at the proximal end of holster (200) and meshes with gear (182) of probe (100) to rotate a rotatable member (310) or other rotatable feature of tissue sample holder (300).

As noted above, rotation of gear (212) provides rotation of needle (110) relative to probe (100). In the present example, gear (212) is rotated by rotating knob (210). In particular, knob (210) is coupled with gear (212) by a series of gears (not shown) and shafts (not shown), such that rotation of knob (210) rotates gear (212). A second knob (210) extends from the other side of holster (200). By way of example only, such a needle rotation mechanism may be constructed in accordance with the teachings of U.S. Pat. No. 9,345,457, issued May 24, 2016, "PRESENTATION OF BIOPSY SAMPLE BY BIOPSY DEVICE", the disclosure of which is incorporated by reference herein. As another merely illustrative example, a needle rotation mechanism may be constructed in accordance with the teachings of U.S. Pub. No. 2010/0160819, "Biopsy Device with Central Thumbwheel", now abandoned, the disclosure of which is incorporated by reference herein.

In some other versions, needle (110) is rotated by a motor. In still other versions, needle (110) is simply rotated by rotating thumbwheel (116). Various other suitable ways in which rotation of needle (110) may be provided will be apparent to those of ordinary skill in the art in view of the teachings herein. It should also be understood that some versions may provide no rotation of needle (110).

Holster (200) also includes a firing rod (226) and fork (222), which couple with needle (110) and fire needle (110) distally. By way of example only, such firing may be useful in instances where biopsy device (10) is mounted to a stereotactic table fixture or other fixture, with tip (112) adjacent to a patient's breast, such that the needle firing mechanism may be activated to drive needle (110) into the patient's breast. The needle firing mechanism may be configured to drive needle (110) along any suitable range of motion, to drive tip (112) to any suitable distance relative to fixed components of probe (100).

In the present example, the needle firing mechanism is coupled with needle (110) via a firing rod (226) and a firing fork (222). Firing rod (226) and firing fork (222) are unitarily secured together. Firing fork (222) includes a pair of prongs (224) that receive hub member (120) of needle (110) therebeteween. Prongs (224) are positioned between annular flange (118) and thumbwheel (116), such that needle (110) will translate unitarily with firing rod (226) and fork (222). Prongs (224) nevertheless removably receive hub member (120), such that fork (222) may be readily secured to hub member (120) when probe (100) is coupled with holster (200); and such that hub member (120) may be readily removed from fork (222) when probe (100) is decoupled from holster (200). Prongs (224) are also configured to permit hub member (120) to rotate between prongs (224). Other suitable components, configurations, and relationships will be apparent to those of ordinary skill in the art in view of the teachings herein. The internal components of the needle firing mechanism of the present example are configured and arranged as described in U.S. Pat. No. 8,858,465, entitled "Biopsy Device with Motorized Needle Firing," issued Oct. 14, 2014, the disclosure of which is incorporated by reference herein.

Holster (200) includes motors (not shown) to drive gears (230, 240) to thereby rotate and translate cutter (150) and rotate rotatable member (310) of tissue sample holder (300). Holster (200) also includes a motor (not shown) that is operable to drive firing rod (226), to thereby arm and fire needle (110). All motors referred to herein are contained within holster (200) in the present example and receive power from vacuum control module (400) via cable (90). In addition, data may be communicated between vacuum control module (400) and holster (200) via cable (90). In some other versions, one or more motors are powered by one or more batteries located within holster (200) and/or probe (100). It should therefore be understood that, as with other components described herein, cable (90) is merely optional. As yet another merely illustrative variation, motors may be powered pneumatically, such that cable (90) may be substituted with a conduit communicating a pressurized fluid medium to holster (200).

As still other merely illustrative variation, cable (90) may include one or more rotary drive cables that are driven by motors that are located external to holster (200). It should also be understood that two or three of the motors may be combined as a single motor. Other suitable ways in which various the motors may be driven will be apparent to those of ordinary skill in the art in view of the teachings herein.

Probe (100) of the present example includes a needle (110) extending distally from probe (100) that is inserted into a patient's tissue to obtain tissue samples. These tissue samples are deposited in a tissue sample holder (300) at the proximal end of probe (100). As shown in FIG. 1, vacuum control module (400) is coupled with probe (100) via a valve assembly (500) and tubes (20, 30, 40), which is operable to selectively provide vacuum, saline, atmospheric air, and venting to probe (100). The internal components of the valve assembly of the present example are configured and arranged as described in U.S. Pat. Pub. No. 2013/0218047, entitled "Biopsy Device Valve Assembly," published Aug. 22, 2013, the disclosure of which is incorporated by reference herein.

As shown in FIGS. 1-6, probe (100) also includes a chassis (106) and a top housing (102), which are fixedly secured together. As best seen in FIG. 3, a gear (140) is exposed through an opening (107) in chassis (106), and is operable to drive cutter actuation mechanism in probe (100). As also seen in FIG. 3, another gear (130) is exposed through chassis (106), and is operable to rotate needle (110) as will be described in greater detail below. Gear (140) of probe (100) meshes with exposed gear (230) of holster (200) when probe (100) and holster (200) are coupled together. Similarly, gear (130) of probe (100) meshes with exposed gear (212) of holster (200) when probe (100) and holster (200) are coupled together.

Needle (110) of the present example comprises a cannula (113) having a piercing tip (112), a lateral aperture (114) located proximal to tip (112), and a hub member (120). Tissue piercing tip (112) is configured to pierce and penetrate tissue, without requiring a high amount of force, and without requiring an opening to be pre-formed in the tissue prior to insertion of tip (112). Alternatively, tip (112) may be blunt (e.g., rounded, flat, etc.) if desired. By way of example only, tip (112) may be configured in accordance with any of the teachings in U.S. Pat. No. 8,801,742, entitled "Needle Assembly and Blade Assembly for Biopsy Device," filed Jun. 1, 2011, the disclosure of which is incorporated by reference herein. As another merely illustrative example, tip (112) may be configured in accordance with at least some of the teachings in U.S. Pat. Pub. No. 2013/0144188, entitled "Biopsy Device with Slide-In Probe," published Jun. 6, 2013, will issue on Nov. 8, 2016 as U.S. Pat. No. 9,486,186, the disclosure of which is incorporated by reference herein. Other suitable configurations that may be used for tip (112) will be apparent to those of ordinary skill in the art in view of the teachings herein.

Lateral aperture (114) is sized to receive prolapsed tissue during operation of device (10). A hollow tubular cutter (150) having a sharp distal edge (152) is located within needle (110). Cutter (150) is operable to rotate and translate relative to needle (110) and past lateral aperture (114) to sever a tissue sample from tissue protruding through lateral aperture (114). For instance, cutter (150) may be moved from an extended position to a retracted position, thereby "opening" lateral aperture (114) to allow tissue to protrude therethrough; then from the retracted position back to the extended position to sever the protruding tissue. As will be described in greater detail below, needle (110) may be rotated to orient lateral aperture (114) at any desired angular position about the longitudinal axis of needle (110). Such rotation of needle (110) is facilitated in the present example by hub member (120), which is described in greater detail below.

Figure 6:
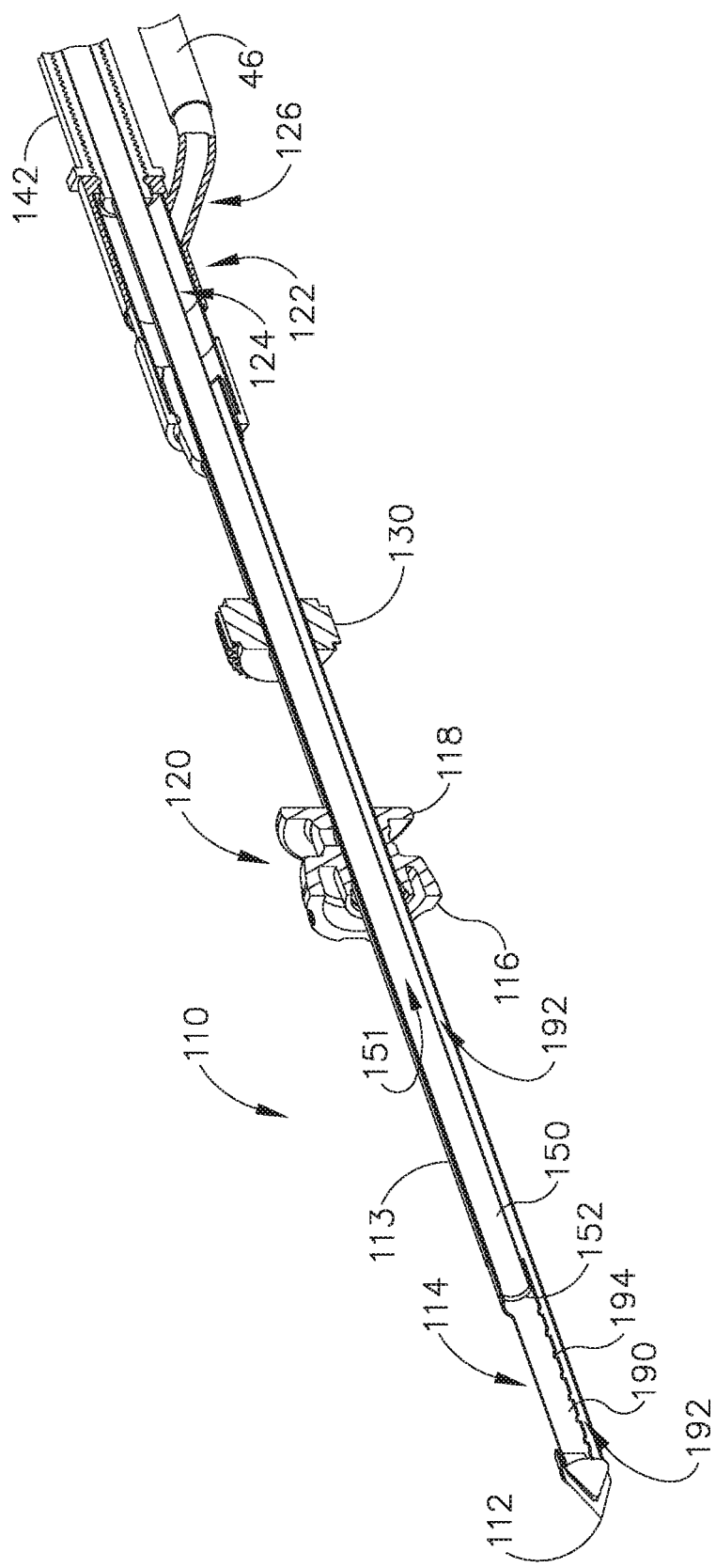
FIG. 6 depicts a cross-sectional view of a needle assembly of the probe of FIG. 4.

As best seen in FIG. 6, needle (110) also includes a longitudinal wall (190) extending proximally from the proximal portion of tip (112). While wall (190) does not extend along the full length of cannula (113) in this example, it should be understood that wall (190) may extend the full length of cannula (113) if desired. Wall (190) defines a distal portion of a second lumen (192) that is lateral to and parallel to cutter (150). Wall (190) proximally terminates at a longitudinal position that is just proximal to the location of distal cutting edge (152) of cutter (150) when cutter (150) is in a proximal-most position as shown in FIG. 6. The exterior of cutter (150) and the interior of cannula (113) together define the proximal portion of second lumen (192) in the length of needle (110) that is proximal to the proximal end of wall (190).

Wall (190) includes a plurality of openings (194) that provide fluid communication between second lumen (192) and the region within cannula (113) that is above wall (190) and below lateral aperture (114). This further provides fluid communication between second lumen (192) and the lumen (151) defined by the interior of cutter (150), as will be described in greater detail below. Openings (194) are arranged such that at least one opening (194) is located at a longitudinal position that is distal to the distal edge of lateral aperture (114). Thus, the lumen (151) of cutter (150) and second lumen (192) may remain in fluid communication even when cutter (150) is advanced to a position where the distal cutting edge of cutter (150) is located at a longitudinal position that is distal to the longitudinal position of the distal edge of lateral aperture (114). An example of such a configuration is disclosed in U.S. Pat. No. 7,918,803, entitled "Methods and Devices for Automated Biopsy and Collection of Soft Tissue," issued Apr. 5, 2011, the disclosure of which is incorporated by reference herein. Of course, as with any other component described herein, any other suitable configurations may be used.

A plurality of external openings (not shown) may also be formed in needle (110), and may be in fluid communication with second lumen (192). For instance, such external openings may be configured in accordance with the teachings of U.S. Pat. No. 7,918,804, entitled "Biopsy Device with Vacuum Assisted Bleeding Control," published Feb. 8, 2007, the disclosure of which is incorporated by reference herein. Of course, as with other components described herein, such external openings in needle (110) are merely optional.

Hub member (120) of the present example is overmolded about needle (110), such that hub member (120) and needle (110) rotate and translate unitarily with each other. By way of example only, needle (110) may be formed of metal, and hub member (120) may be formed of a plastic material that is overmolded about needle (110) to unitarily secure and form hub member (120) to needle (110). Hub member (120) and needle (110) may alternatively be formed of any other suitable material(s), and may be secured together in any other suitable fashion. Hub member (120) includes an annular flange (118) and a thumbwheel (116). Gear (130) is slidably and coaxially disposed on a proximal portion (150) of hub member (120) and is keyed to hub member (120), such that rotation of gear (130) will rotate hub member (120) and needle (110); yet hub member (120) and needle (110) may translate relative to gear (130). Gear (130) is rotatably driven by gear (212). Alternatively, needle (110) may be rotated by rotating thumbwheel (116). Various other suitable ways in which manual rotation of needle (110) may be provided will be apparent to those of ordinary skill in the art in view of the teachings herein. It should also be understood that rotation of needle (110) may be automated in various ways, including but not limited to the various forms of automatic needle rotation described in various references that are cited herein.

As shown in FIGS. 4-7, a rotatable member (122) or manifold is provided at the proximal end of needle (110). Rotatable member (122) defines a hollow interior (124) and includes a port (126) in fluid communication with hollow interior (124). As best seen in FIG. 6, hollow interior (124) is also in fluid communication with second lumen (192) of needle (110). Port (126) is coupled with tube (46), such that rotatable member (122) provides fluid communication between second lumen (192) and tube (46). Rotatable member (122) also seals against the exterior of needle (110) such that rotatable member (122) provides a fluid tight coupling between second lumen (192) and tube (46) even if needle (110) is translated and/or rotated relative to rotatable member (122), such as during firing of needle (110) or re-orientation of needle (110), respectively.

Figure 4:
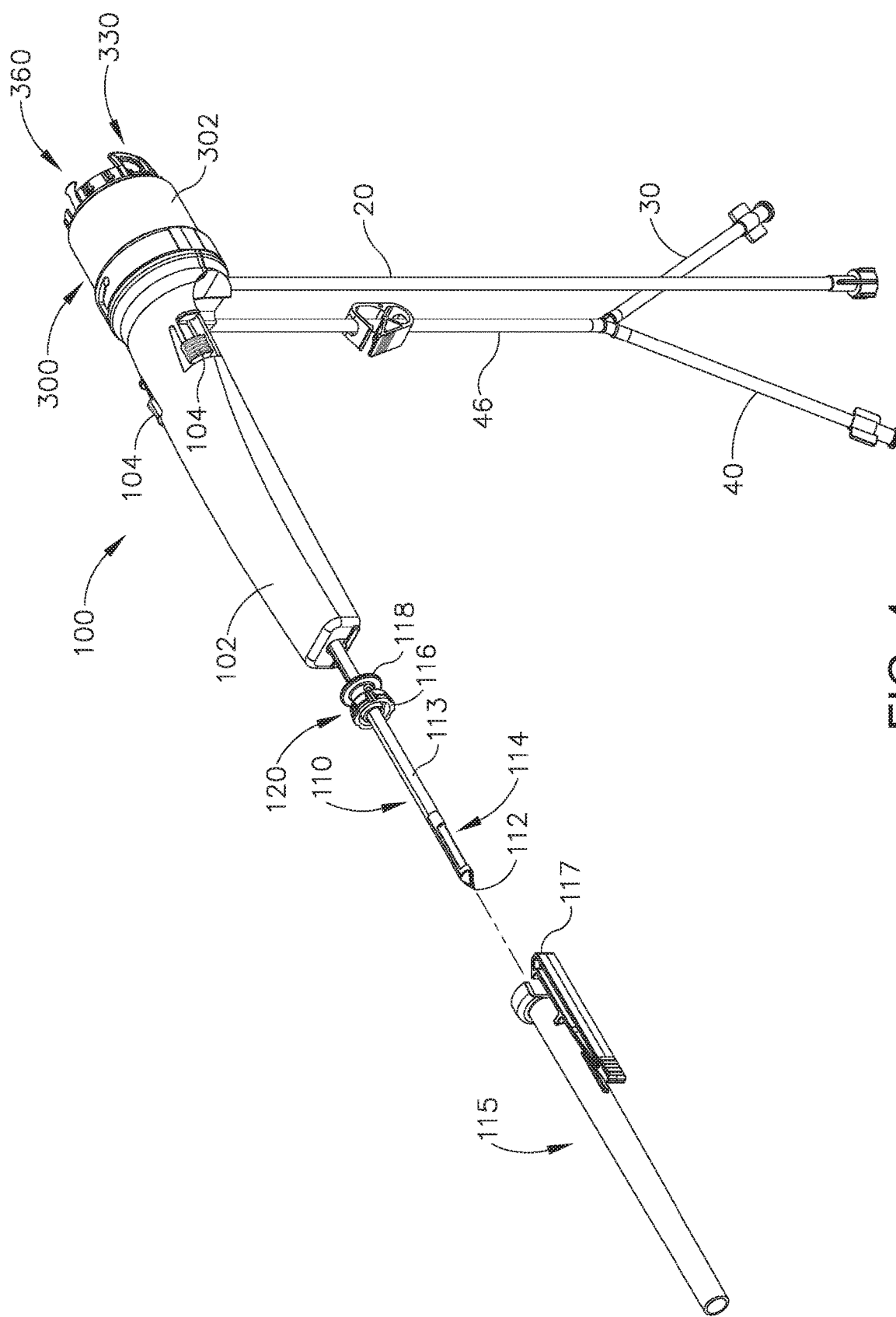
FIG. 4 depicts a perspective view of the probe of the biopsy device of FIG. 2.

As shown in FIG. 4, needle (110) may be provided with a removable cover (115). Cover (115) of this example includes a resiliently biased latch (117) that is configured to engage thumbwheel (116), to thereby removably secure cover (115) to needle (110). Cover (115) is configured to cover tip (112) when latch (117) is engaged with thumbwheel (116), such that cover (115) protects the user of biopsy device (10) from inadvertent contact with tip (112). Cover (115) may also include one or more wiper seals near the proximal end and/or distal end of cover (115), to seal against cannula (113). By way of example only, cover (115) may be configured in accordance with at least some of the teachings in U.S. Pat. Pub. No. 2013/0144188, the disclosure of which is incorporated by reference herein. Various other suitable configurations for cover (115) will be apparent to those of ordinary skill in the art in view of the teachings herein. Of course, cover (115) may simply be omitted if desired. It should also be understood that, as with other components described herein, needle (110) may be varied, modified, substituted, or supplemented in a variety of ways; and that needle (110) may have a variety of alternative features, components, configurations, and functionalities. For instance, needle (110) may be constructed in accordance with the teachings of U.S. Pat. No. 9,345,457, issued May 24, 2016, the disclosure of which is incorporated by reference herein, and/or in accordance with the teachings of any other reference cited herein.

Figure 5:
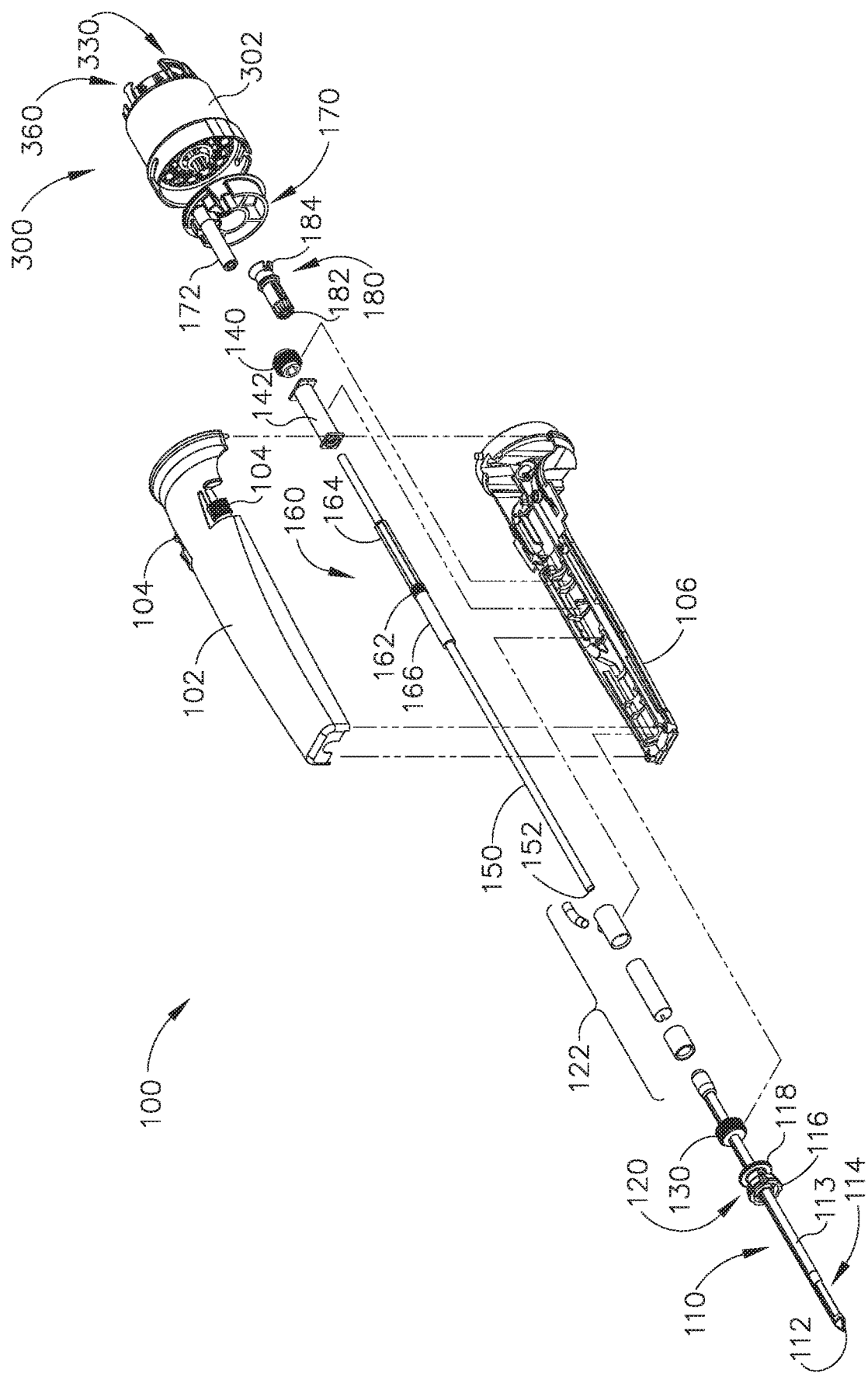
FIG. 5 depicts an exploded view of the probe of FIG. 4.
Figure 7:
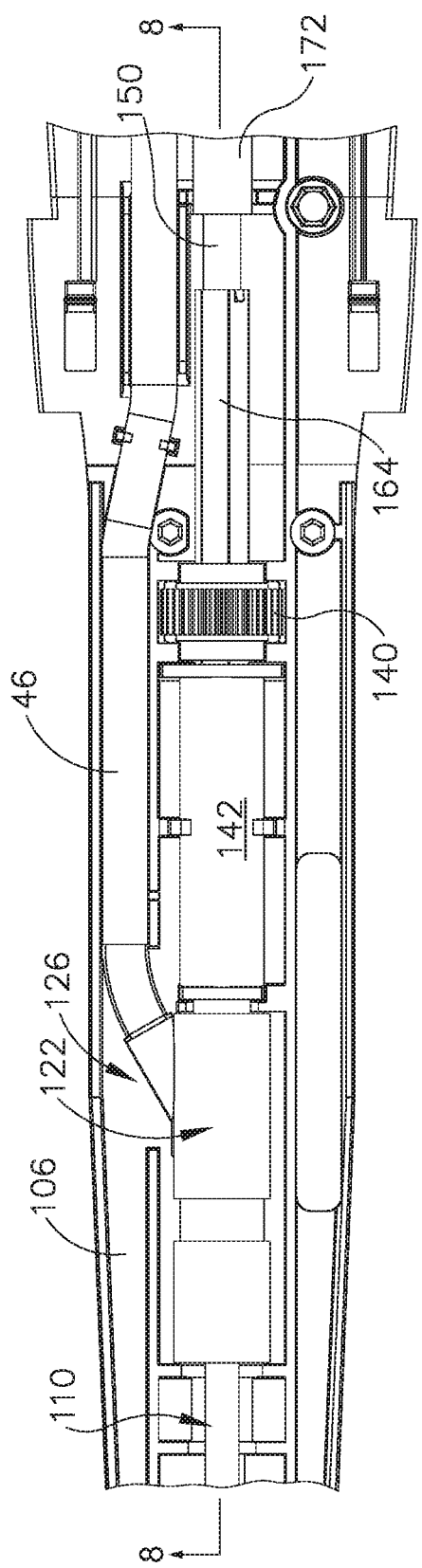
FIG. 7 depicts a partial top plan view of components of the probe of FIG. 4, with a top housing piece removed.

As noted above, cutter (150) is operable to simultaneously translate and rotate relative to needle (110) to sever a tissue sample from tissue protruding through lateral aperture (114). As best seen in FIGS. 5-7 cutter (150) includes an overmold (160) that is unitarily secured to cutter (150). Overmold (160) includes a generally smooth and cylindraceous distal portion (166), threading (162) in a mid-region of overmold (160), and a set of hexagonal flats (164) extending along a proximal portion of overmold (160). Distal portion (166) extends into rotatable member (122). Rotatable member (122) seals against distal portion (166) such that rotatable member (122) such that rotatable member (122) maintains the fluid tight coupling between second lumen (192) and tube (46) even when cutter (150) is translated and rotated relative to rotatable member (122).

Figure 8:
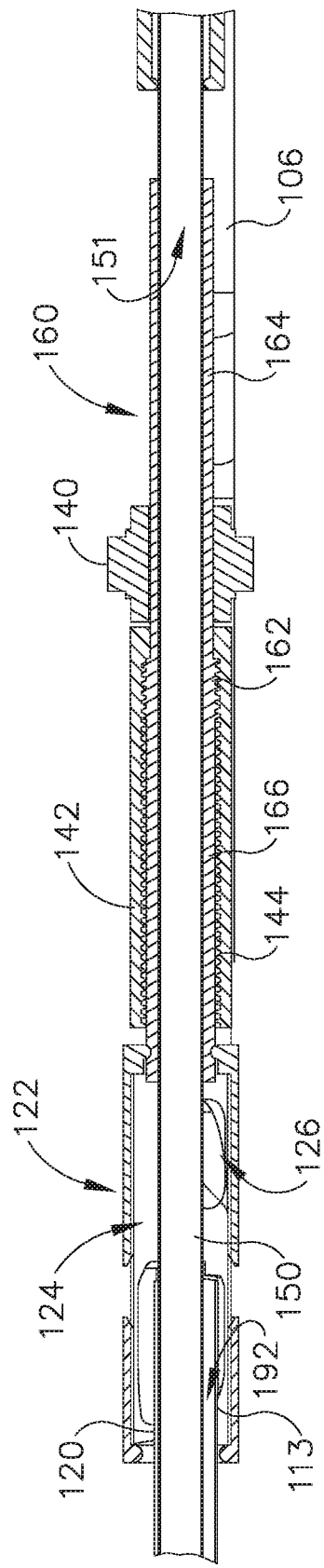
FIG. 8 depicts a side cross-sectional view of the components of FIG. 7, taken along line 8-8 of FIG. 7.

A gear (140) is positioned on flats (164) and includes a set of internal flats (not shown) that complement flats (164). Thus, gear (140) rotates overmold (160) and cutter (150) when gear (140) is rotated. However, overmold (160) is slidable relative to gear (140), such that cutter (150) may translate relative to chassis (160) despite gear (140) being longitudinally fixed relative to chassis (160). Gear (140) is rotated by gear (230). As best seen in FIGS. 7-8, a nut (142) is associated with threading (162) of overmold (160). In particular, nut (142) includes internal threading (144) that meshes with threading (162) of overmold (160). Nut (142) is fixedly secured relative to chassis (160). Thus, when gear (140) rotates cutter (150) and overmold (160), cutter (150) will simultaneously translate due to the meshing of threading (144, 162). In some versions, the foregoing cutter actuation components are further configured in accordance with at least some of the teachings of U.S. Pat. Pub. No. 2008/0214955, the disclosure of which is incorporated by reference herein. As yet another merely illustrative example, cutter (150) may be rotated and/or translated using pneumatic motors, etc. Still other suitable ways in which cutter (150) may be actuated will be apparent to those of ordinary skill in the art in view of the teachings herein.

Tissue sample holder (300) of the present example provides a plurality of discrete chambers that are configured to receive tissue samples that are severed by cutter (150) and communicated proximally through lumen (151) of cutter (150). In particular, and as will be described in greater detail below, tissue sample holder (300) includes tissue receiving trays (330) that are removably engaged with a rotatable member (310) or manifold. Rotatable member (310) is removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate rotatable member (310)

to index tissue chambers relative to lumen (151) of cutter (150) as will be described in greater detail below. A transparent outer cup (302) or cover is positioned about rotatable member (310) and is removably secured to chassis (106). While bayonet features provide coupling between outer cup (302) and chassis (106), it should be understood that any suitable type of coupling may be used. Rotatable member (310) is freely rotatable within a chamber defined by outer cup (302). However, rotatable member (310) is engaged with outer cup (302) such that rotatable member (310) will decouple relative to chassis (106) when outer cup (302) is removed from chassis (106). In other words, rotatable member (310) may be selectively coupled with and removed relative to chassis (106) by coupling and removing outer cup (302) from chassis (106).

Figure 11:
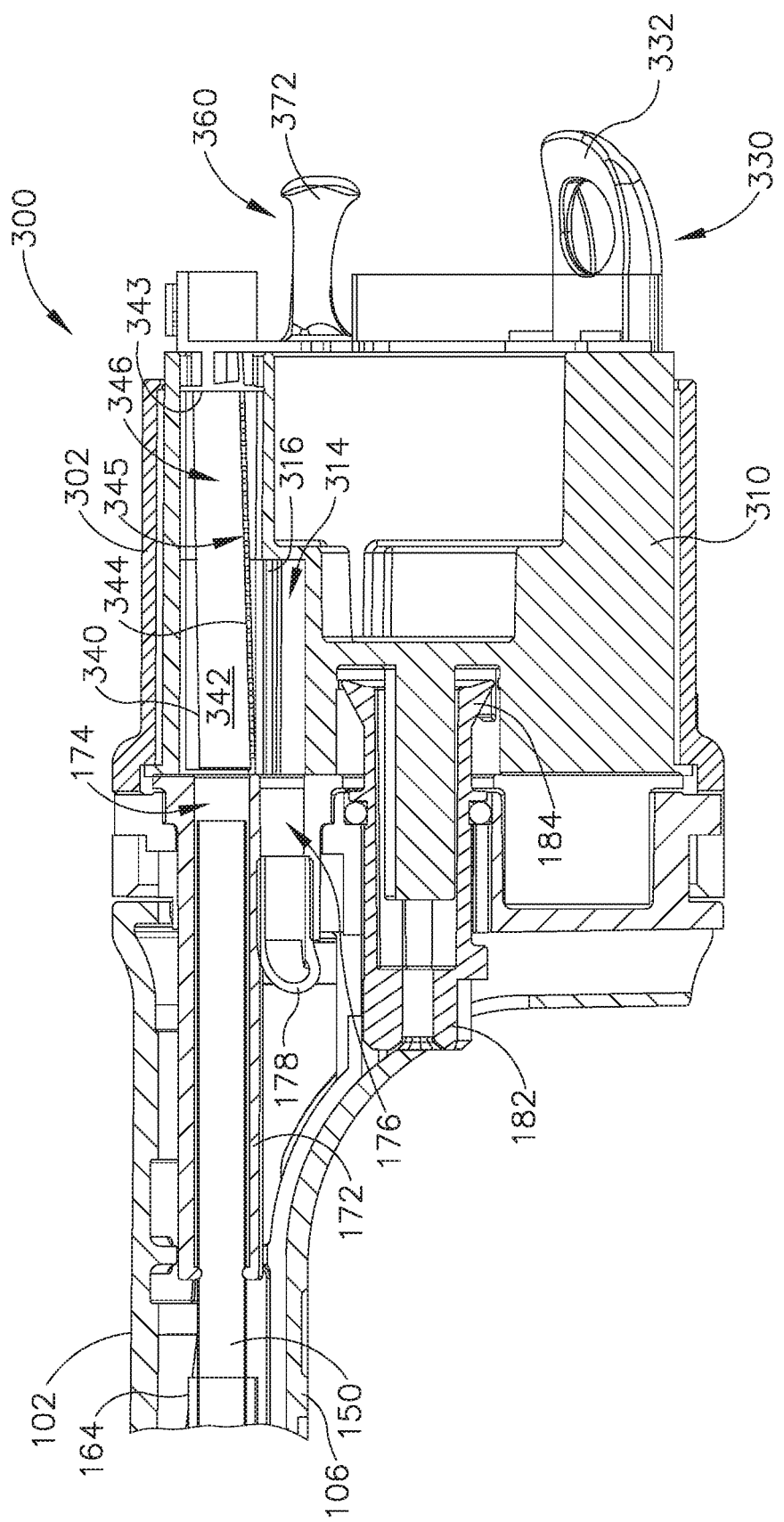
FIG. 11 depicts a side cross-sectional view of the tissue sample holder assembly of FIG. 9, with a tissue sample chamber aligned with the cutter.
Figure 12:
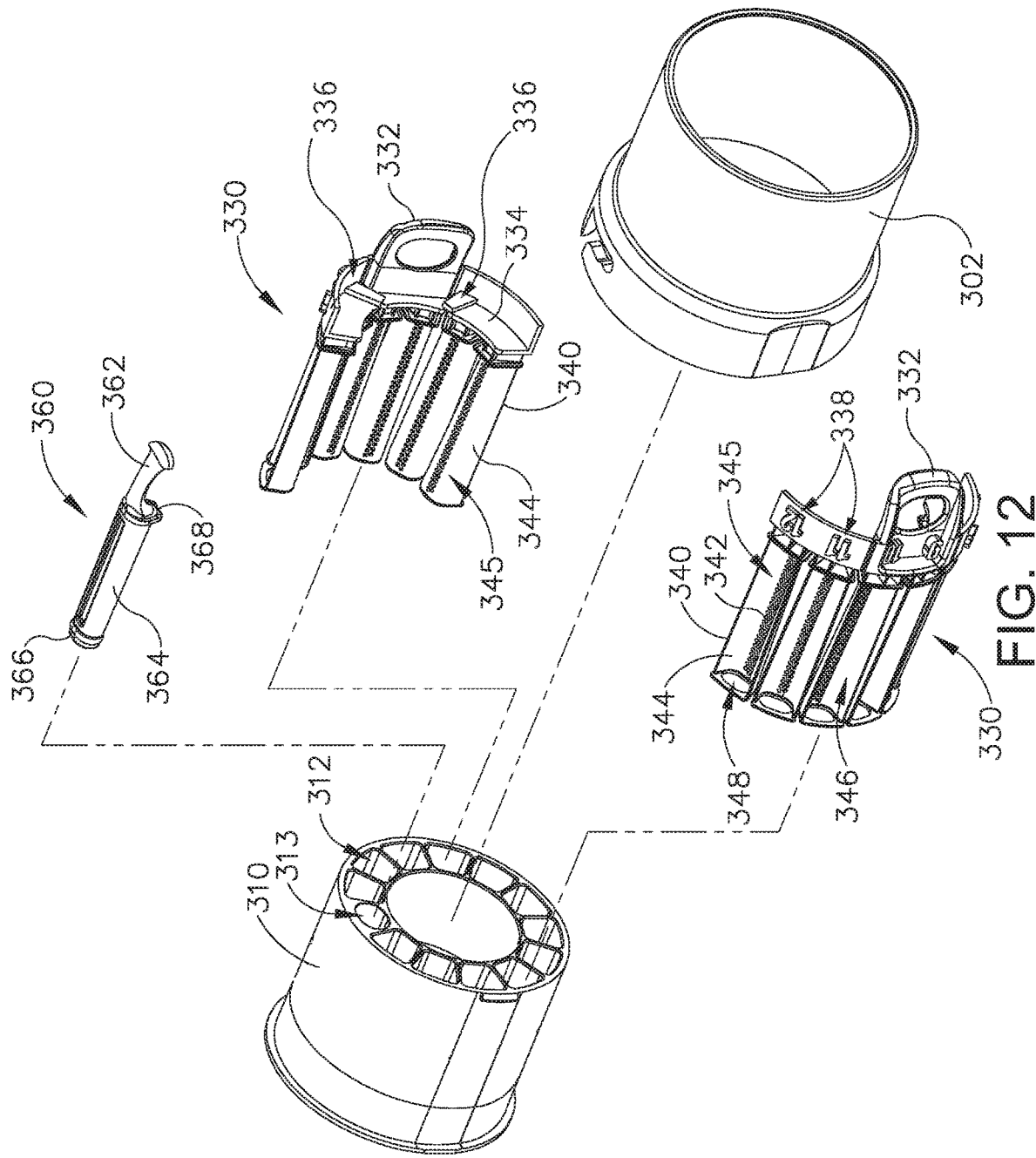
FIG. 12 depicts an exploded view of components of rotatable components of the tissue sample holder assembly of FIG. 9

As best seen in FIG. 12, rotatable member (310) of the present example generally comprises a rotatable member and defines a plurality of chambers in the form of passages (312) that extend longitudinally through rotatable member (310) and that are angularly arrayed about the central axis of rotatable member (310). A lateral recess (314) (FIG. 11) is associated with a distal portion of each passage (312). Shelves (316) demarcate boundaries between each passage (312) and the associate lateral recess (314). As will be described in greater detail below, passages (312) receive trays (330) while recesses (314) provide pneumatic passages. An additional passage (313) and recess (315) are associated with a plug (360), as will also be described in greater detail below. Rotatable member (310) also includes a central shaft (320), which is configured to removably engage grasping feature (184). Central shaft (320) couples with grasping feature (184) upon coupling of outer cup (302) with chassis (106), as described above. Engagement between central shaft (320) and grasping feature (184) provides rotation of rotatable member (310) upon rotation of gear (182).

Figure 9:
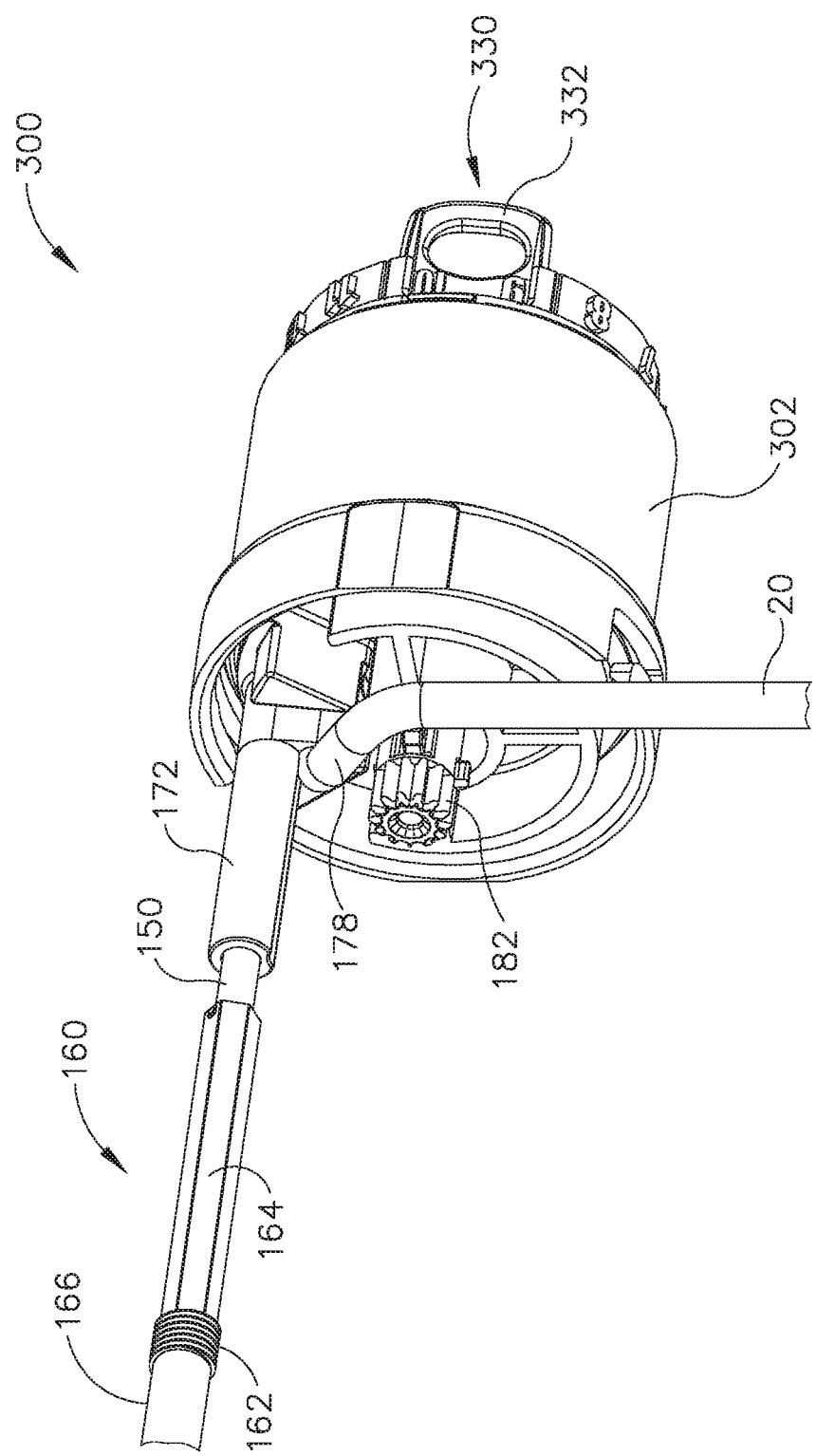
FIG. 9 depicts a perspective view of a tissue sample holder assembly of the probe of FIG. 4.
Figure 10:
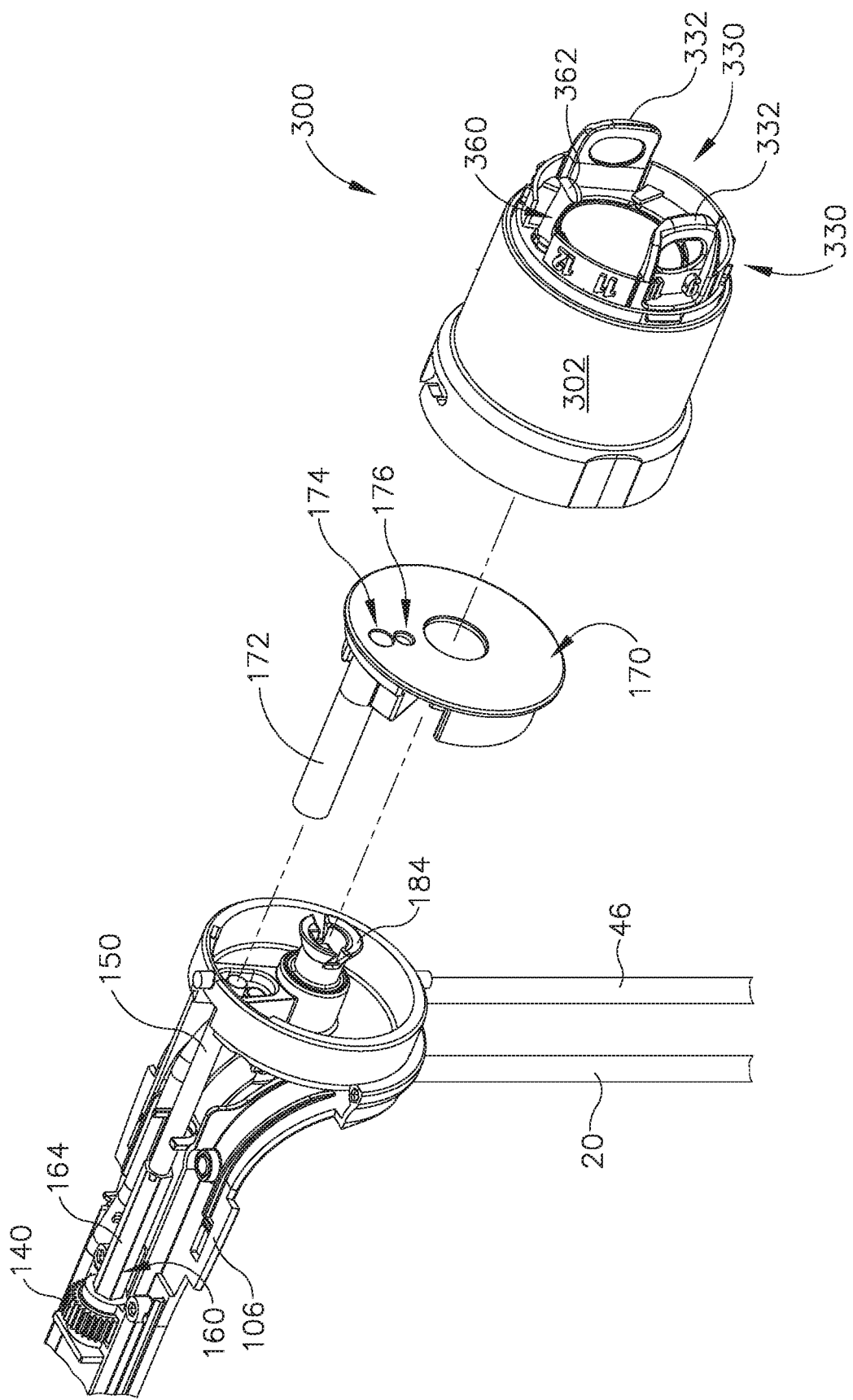
FIG. 10 depicts an exploded view of the tissue sample holder assembly of FIG. 9.

As best seen in FIGS. 10-11, a sealing member (170) is provided at the proximal end of chassis (106) and interfaces with the distal face of rotatable member (310). In the present example, sealing member (170) comprises rubber, though it should be understood that any other suitable material(s) may be used. Sealing member (170) includes a longitudinally extending cutter seal (172), which receives cutter (150) and seals against the exterior of cutter (150). The proximal end of cutter (150) remains within cutter seal (172) throughout the full range of travel of cutter (150). Cutter seal (172) maintains a fluid tight seal against cutter (150) during this full range of motion, including during rotation and translation of cutter (150). An opening (174) is positioned at the proximal end of cutter seal (170). This opening (174) is configured to align with whichever passage (312, 313) is at the 12 o'clock position. Another opening (176) is positioned below opening (174). Opening (176) is configured to align with whichever recess (314, 315) is at the 12 o'clock position. As best seen in FIGS. 9 and 11, opening (176) is in fluid communication with a port (178), which is coupled with tube (20). Thus, sealing member (170) provides fluid communication between tube (20) and whichever recess (314, 315) is at the 12 o'clock position. As will be described in greater detail below, rotatable member (310) further provides fluid communication between such recess (314, 315) and the associated passage (312, 313) at the 12 o'clock position; and thereby further to lumen (151) of cutter (150). In other words, sealing member (170) and rotatable member (310) cooperate to provide fluid communication between tube (20) and lumen (151) of cutter (150) via whichever passage (312, 313) and recess (314, 315) are at the 12 o'clock position. It should be understood that sealing member (170) of the present example maintains a fluid tight seal against the distal face of rotatable member (310), even as rotatable member (310) is rotated relative to sealing member (170).

As noted above, tissue sample holder trays (330) are configured to removably engage rotatable member (310). Each tissue sample holder tray (330) of the present example includes a grip (332), a proximal wall (334), and a plurality of strips (340) extending distally from proximal wall (334). Strips (340) are sized and configured for insertion into associated passages (312) of rotatable member (310). Each strip (340) includes a pair of sidewalls (344) and a floor (342). Each pair of sidewalls (344) and floor (342) together define a corresponding tissue sample chamber (346). An opening (348) is provided at the distal end of each tissue sample chamber (346). Opening is sized and positioned to correspond with opening (174) of sealing member (170). Thus, the lumen (151) of cutter (150) is in fluid communication with the tissue sample chamber (346) of the strip (340) inserted in the passage (312) that is at the 12 o'clock position. As best seen in FIG. 11, strips (340) are configured such that the distal portion of each strip (340) receives support from a corresponding shelf (316) of rotatable member (310). Each floor (342) includes a plurality of openings (345) that provide fluid communication between tissue sample chamber (346) of strip (340) and lateral recess (314) of the passage (312) associated with strip (340). Thus, vacuum, atmospheric air, etc. that is communicated to opening (176) via tube (20) is further communicated to lumen (151) of cutter (150) via lateral recess (314), openings (345), and tissue sample chamber (346). During operation of biopsy device (10), tissue samples severed by distal edge (152) of cutter (150) are communicated proximally through the lumen (151) of cutter (150) and are then deposited into the tissue sample chamber (346) that is aligned with lumen (151) of cutter (150). Rotatable member (310) is rotated to successively align tissue sample chambers (346) with lumen (151) of cutter (150), enabling several tissue samples to be separately deposited in different tissue sample chambers (346) during operation of biopsy device (10). Bodily fluids and saline, etc. that are pulled through lumen (151) will pass through tissue sample holder (300) and tube (20) and are eventually deposited in vacuum canister (70).

Each strip (340) also includes a pair of wiper seals (343, 349) that seal against the interior of passage (312) when strip (340) is fully inserted into passage (312). Wiper seals (343, 349) provide a fluid tight seal for tissue sample chambers (346) and further provide frictional resistance to removal of strips (340) from rotatable member (310). Grips (332) are configured to facilitate removal of strips (340) from rotatable member (310), such as during or after a biopsy procedure to retrieve or otherwise directly observe tissue samples deposited in tissue sample chambers (346). Trays (330) also include numerical indicia (338) associated with each tissue sample chamber (346). In addition, trays (330) include pinched regions (336) that facilitate flattening of trays (330). In particular, pinched regions (336) provide sufficient flexibility to enable trays (330) to form an arcuate configuration for insertion into rotatable member (310); while also enabling trays (330) to form a generally flat configuration such as after trays (330) are removed from rotatable member (310) for inspection of tissue samples in trays (330).

It should be understood that rotatable member (310) and/or trays (330) may be configured in numerous other ways. By way of example only, rotatable member (310) and/or trays (330) may be configured in accordance with at least some of the teachings of U.S. Pat. Pub. No. 2008/0214955, the disclosure of which is incorporated by reference herein. As another merely illustrative example, rotatable member (310) and/or trays (330) may be configured in accordance with at least some of the teachings of U.S. Pat. No. 8,702,623, the disclosure of which is incorporated by reference herein. It should also be understood that tissue sample holder (300) need not necessarily position chambers (346) coaxially with lumen (151) of cutter (150). Tissue sample holder (300) may index chambers (346) relative to cutter (150) in any other suitable fashion. For instance, chambers (346) may extend along axes that are always offset from the axis of lumen (151), along axes that are oblique or perpendicular relative to the axis of lumen (151), or along other axes. Similarly, it should be understood that rotatable member (310) may rotate about an axis that is oblique or perpendicular relative to the axis of lumen (151). Still other suitable configurations will be apparent to those of ordinary skill in the art in view of the teachings herein.

As best seen in FIG. 12, and as noted above, tissue sample holder (300) of the present example includes a plug (360) that is received in a dedicated passage (313) of rotatable member (310). Plug (360) includes a grip (362) and a longitudinally extending body (364). Body (364) extends through part of the length of passage (313), distally terminating at the longitudinal position corresponding with the proximal end of recess (315). Plug (360) includes a pair of seals (366, 368) that seal against the interior of passage (313) when plug (360) is fully inserted in passage (313). Seals (366, 368) thus keep passage (313) fluid tight when plug (360) is inserted in passage (313). Passage (313) is configured to receive the shaft of a biopsy site marker applier. Passage (313) may also receive an instrument for delivering medicine, etc. to a biopsy site. By way of example only, passage (313) may receive an adapter configured to provide an interface between passage (313) and a conventional medicine deliver device. An example of such an adapter and other uses/configurations for a passage like passage (313) are described in U.S. Pat. No. 8,118,755, the disclosure of which is incorporated by reference herein. Plug (360) and/or passage (313) may also be configured and operable in accordance with at least some of the teachings of U.S. Pat. No. 8,938,285, the disclosure of which is incorporated by reference herein. Still other suitable configurations will be apparent to those of ordinary skill in the art in view of the teachings herein. In some other versions, plug (360) and/or passage (313) are simply omitted.

As described above, tissue sample holder (300) is generally configured to collect a plurality of tissue samples individually in discrete tissue sample trays (330). However, it should be understood that in some examples it may be desirable to collect a plurality of tissue samples is a single chamber. By way of example only, such a feature may be desirable where tissue samples are collected merely for removal of tissue from a patient, rather than for diagnostic purposes. Of course, in such circumstances, tissue samples collected in a single chamber may later be used for diagnostic purposes, even if the original intent was merely for tissue removal. In addition or in alternative, some operators may prefer collecting a plurality of tissue samples in a single chamber rather than individual chambers when collecting tissue samples for diagnostic purposes. In still further instances, an operator may desire to alternate between the modes described above to briefly analyze tissue sample quality using an individual tissue sample mode of collection and then proceed to a bulk tissue sample mode of collection for collection of tissue samples in the same general anatomical area. Thus, it should be understood that in some examples it may be desirable to include a means of bulk tissue collection in a tissue sample holder similar to tissue sample holder (300) described above.

The following examples include several exemplary alternative tissue sample holders and/or tissue sample holder features that provide bulk tissue collection in addition to, or in lieu of, the individual mode of tissue sample collection described above. The following examples are provided in the context of biopsy device (10). However, it should be understood that the various examples described below may also be incorporated into various other kinds of biopsy devices.

Figure 13:
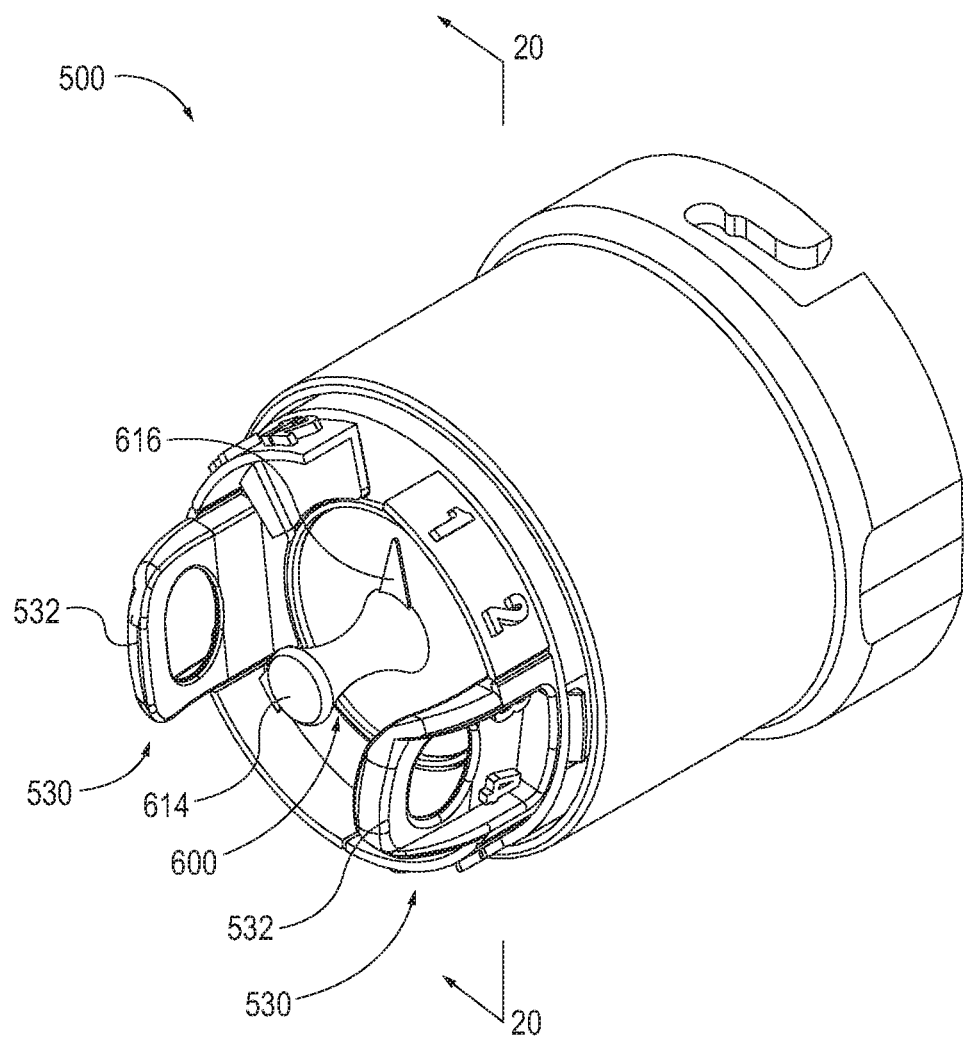
FIG. 13 depicts a perspective view of an exemplary alternative tissue sample holder for use with the biopsy device of FIG. 2.
Figure 14:
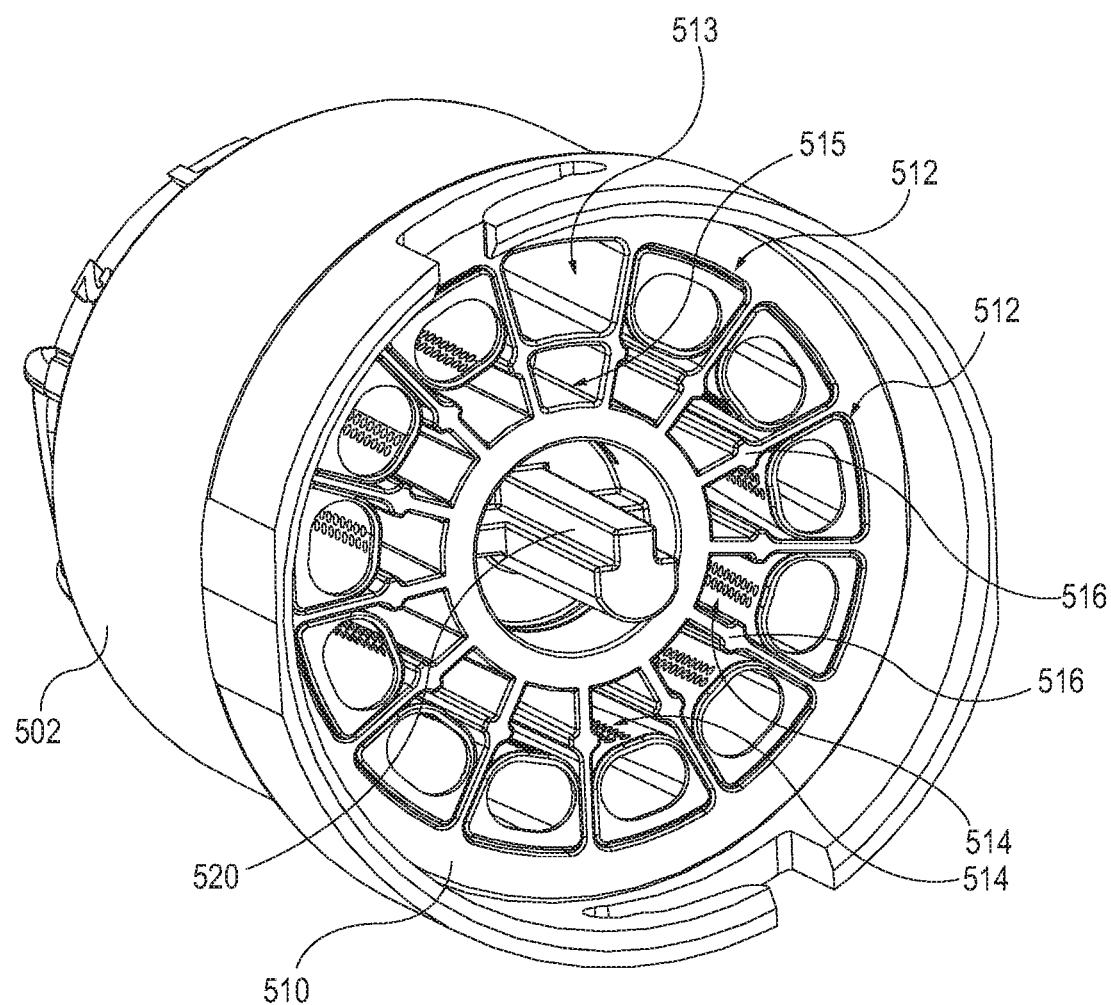
FIG. 14 depicts another perspective view of the tissue sample holder of FIG. 13.
Figure 15:
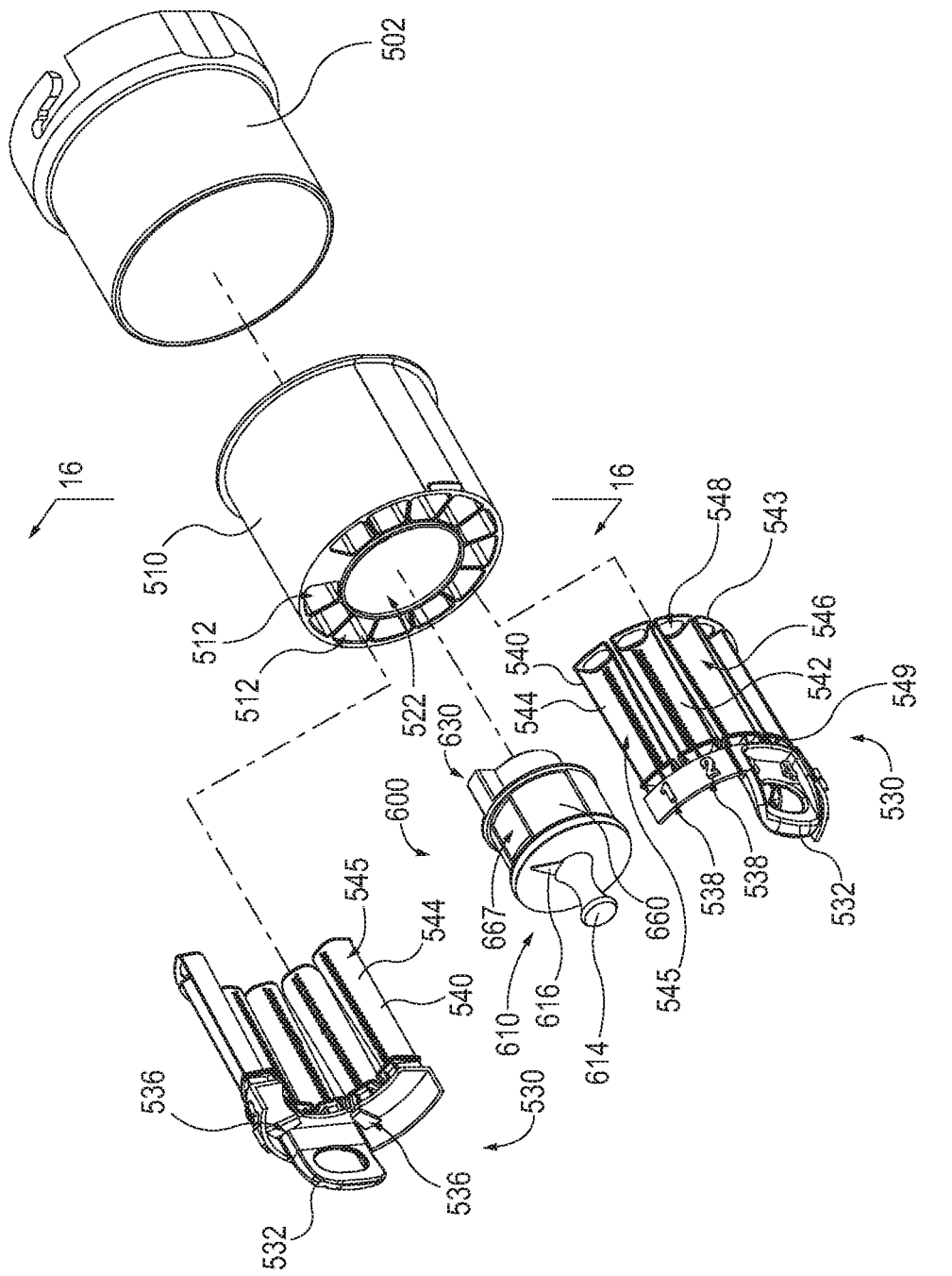
FIG. 15 depicts an exploded perspective view of the tissue sample holder of FIG. 13.

FIGS. 13-15 show an exemplary alternative tissue sample holder (500) that may be readily incorporated into biopsy device (10) as similarly described with respect to tissue sample holder (300) above. Unless otherwise indicated herein, it should be understood that tissue sample holder (500) is substantially the same as tissue sample holder (300) described above. Tissue sample holder (500) of the present example provides a plurality of discrete chambers that are configured to receive tissue samples that are severed by cutter (150) and communicated proximally through lumen (151) of cutter (150). In particular, and as will be described in greater detail below, tissue sample holder (500) includes tissue receiving trays (530) that are removably engaged with a rotatable member (510) or manifold. Unlike tissue sample holder (300) described above, tissue sample holder (500) of the present example further includes a bulk cup assembly (600) (also referred to as an inner cup) that is removably engaged with rotatable member (510). As will be described in greater detail below, tissue sample holder (500) of the present example is generally configured to permit an operator to selectably collect tissue samples in an individual tissue sample chamber or a bulk tissue sample collection chamber.

As with rotatable member (310) described above, rotatable member (510) generally comprises a rotatable member and is configured to be removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate rotatable member (510) to index tissue chambers relative to lumen (151) of cutter (150) as will be described in greater detail below. A transparent outer cup (502) or cover is positioned about rotatable member (510) and is configured to be removably secured to chassis (106). While bayonet features provide coupling between outer cup (502) and chassis (106), it should be understood that any suitable type of coupling may be used. Rotatable member (510) is freely rotatable within a chamber defined by outer cup (502). However, rotatable member (510) is engaged with outer cup (502) such that rotatable member (510) will decouple relative to chassis (106) when outer cup (502) is removed from chassis (106). In other words, rotatable member (510) may be selectively coupled with and removed relative to chassis (106) by coupling and removing outer cup (502) from chassis (106).

As best seen in FIGS. 14 and 15, rotatable member (510) of the present example defines a plurality of chambers in the form of passages (512) that extend longitudinally through rotatable member (510) and that are angularly arrayed about the central axis of rotatable member (510). Like with passages (312) described above, a lateral recess (314) (FIG. 14) is associated with a distal portion of each passage (512).

Shelves (516) demarcate boundaries between each passage (512) and the associated lateral recess (514). As will be described in greater detail below, passages (512) receive trays (530) while recesses (514) provide pneumatic passages.

Similarly to rotatable member (310) described above, rotatable member (510) includes an additional passage (513) and recess (515). However, unlike passage (313) and recess (315) described above, passage (513) and recess (515) are not associated with a plug similar to plug (370). Instead, as will be described in greater detail below, passage (513) and recess (515) are configured to communicate tissue samples to bulk cup assembly (600) when lumen (151) of cutter (150) is aligned with passage (513).

Rotatable member (510) also includes a central shaft (520), which is configured to removably engage grasping feature (184). Central shaft (520) is configured to couple with grasping feature (184) upon coupling of outer cup (502) with chassis (106), as described above. Engagement between central shaft (520) and grasping feature (184) provides rotation of rotatable member (510) upon rotation of gear (182).

As noted above, tissue sample holder trays (530) are configured to removably engage rotatable member (510). Each tissue sample holder tray (530) of the present example includes a grip (532), a proximal wall (534), and a plurality of strips (540) extending distally from proximal wall (534). Strips (540) are sized and configured for insertion into associated passages (512) of rotatable member (510). Each strip (540) includes a pair of sidewalls (544) and a floor (542). Each pair of sidewalls (544) and floor (542) together define a corresponding tissue sample chamber (546). An opening (548) is provided at the distal end of each tissue sample chamber (546). Opening is sized and positioned to correspond with opening (174) of sealing member (170). Thus, the lumen (151) of cutter (150) is in fluid communication with the tissue sample chamber (546) of the strip (540) inserted in the passage (512) that is at the 12 o'clock position. Strips (540) are configured such that the distal portion of each strip (540) receives support from a corresponding shelf (516) of rotatable member (510). Each floor (542) includes a plurality of openings (545) that provide fluid communication between tissue sample chamber (546) of strip (540) and lateral recess (514) of the passage (512) associated with strip (540). Thus, vacuum, atmospheric air, etc. that is communicated to opening (176) via tube (20) is further communicated to lumen (151) of cutter (150) via lateral recess (514), openings (545), and tissue sample chamber (546). During operation of biopsy device (10), tissue samples severed by distal edge (152) of cutter (150) are communicated proximally through the lumen (151) of cutter (150) and are then deposited into the tissue sample chamber (546) that is aligned with lumen (151) of cutter (150). Rotatable member (510) is rotated to successively align tissue sample chambers (546) with lumen (151) of cutter (150), enabling several tissue samples to be separately deposited in different tissue sample chambers (546) during operation of biopsy device (10). Bodily fluids and saline, etc. that are pulled through lumen (151) will pass through tissue sample holder (500) and tube (20) and are eventually deposited in vacuum canister (70).

Each strip (540) also includes a pair of wiper seals (543, 549) that seal against the interior of passage (512) when strip (540) is fully inserted into passage (512). Wiper seals (543, 549) provide a fluid tight seal for tissue sample chambers (546) and further provide frictional resistance to removal of strips (540) from rotatable member (510). Grips (532) are configured to facilitate removal of strips (540) from rotatable member (510), such as during or after a biopsy procedure to retrieve or otherwise directly observe tissue samples deposited in tissue sample chambers (546). Trays (530) also include numerical indicia (538) associated with each tissue sample chamber (546). In addition, trays (530) include pinched regions (536) that facilitate flattening of trays (530). In particular, pinched regions (536) provide sufficient flexibility to enable trays (530) to form an arcuate configuration for insertion into rotatable member (510); while also enabling trays (530) to form a generally flat configuration such as after trays (530) are removed from rotatable member (510) for inspection of tissue samples in trays (530).

Figure 16:
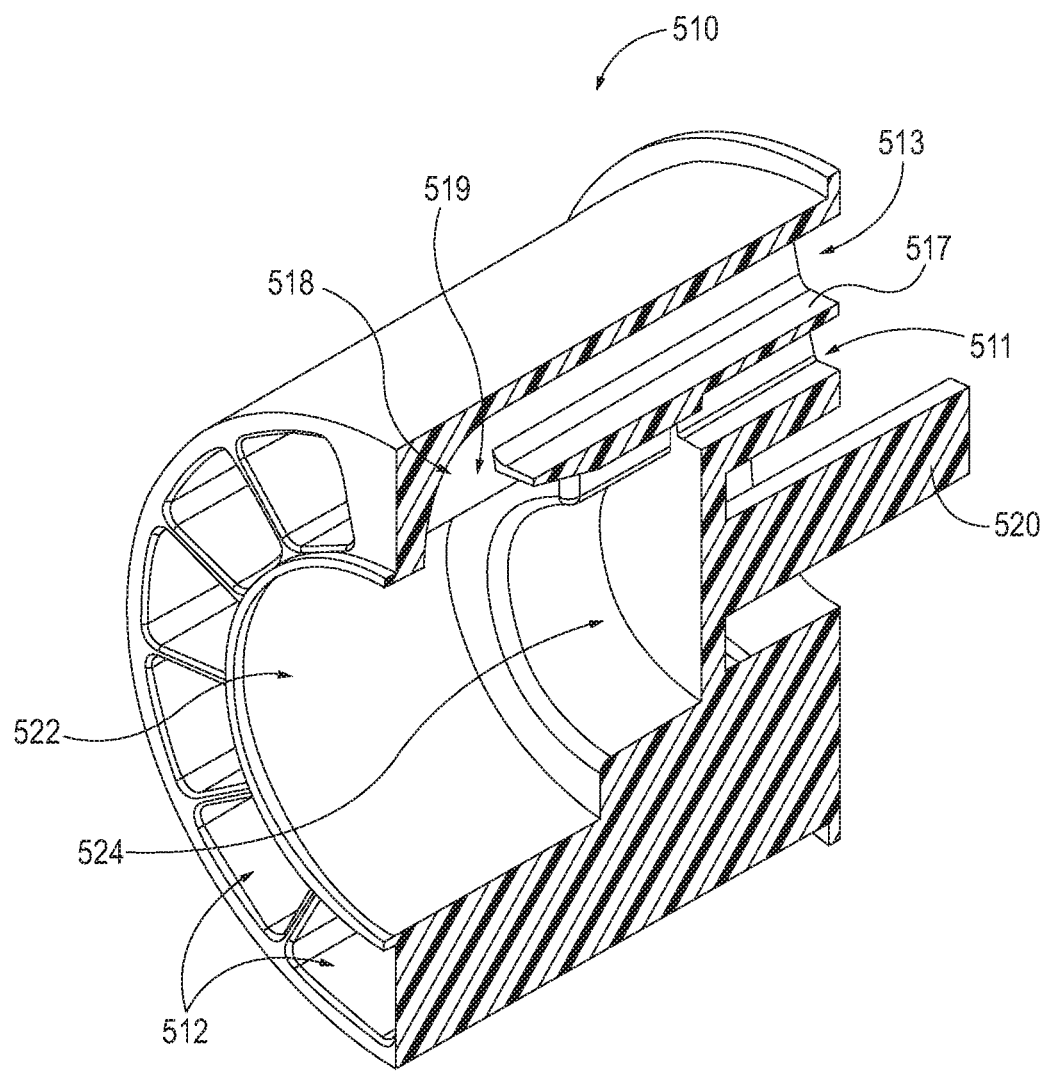
FIG. 16 depicts a perspective cross-sectional view of a rotatable member of the tissue sample holder of FIG. 13, the cross-section taken along line 16-16 of FIG. 15.

Like rotatable member (310) described above, rotatable member (510) of the present example includes passage (513) in addition to passages (512). However, unlike passage (313) of rotatable member (310), passage (513) of the present example is configured to communicate fluids from lumen (151) of cutter (150) to the interior of rotatable member (510). In particular, as can be seen in FIG. 16, passage extends longitudinally though rotatable member (510). However, instead of having an open proximal end, passage includes a curved portion (518) that shifts passage (513) perpendicularly relative to the longitudinal axis of rotatable member (510). Adjacent to passage (513) is a shelf (517). Shelf (517) also extends longitudinally though rotatable member (510), but terminates distally of curved portion (518) of passage (513). This configuration defines an opening (519) within passage (513) that is in communication with the interior of rotatable member (510).

Shelf (517) further defines a vacuum passage (511) disposed below shelf (517). Vacuum passage (511) extends longitudinally through rotatable member (510) and is in communication with the interior of rotatable member (510). As will be described in greater detail below, passage (513) is configured to communicate tissue samples from lumen (151) of cutter (150) to the interior of rotatable member (510), while passage (511) is configured to communicate vacuum from biopsy device (10) to the interior of rotatable member (510).

The interior of rotatable member (510) defines a first cylindrical portion (522) and a second cylindrical portion (524). As will be described in greater detail below, cylindrical portions (522, 524) are configured to receive a bulk cup assembly (600) such that passage (513) may be used to collect multiple tissue samples in a bulk collection mode. In the present example, first cylindrical portion (522) is in communication with passage (513), while second cylindrical portion (524) is in communication with passage (511). First cylindrical portion (522) is further open to the proximal end of rotatable member (510) such that first cylindrical portion (522) is in communication with the exterior of rotatable member (510). First cylindrical portion (522) of the present example has a generally greater diameter than the diameter of second cylindrical portion (524). Although cylindrical portions (522, 524) of the present example are shown as discrete portions of rotatable member (510), it should be understood that in other examples, cylindrical portions (522, 524) are consolidated into a single cylindrical portion. Additionally, although cylindrical portions (522, 524) are described herein as having a generally cylindrical shape, in other examples any other suitable shape is used.

Figure 17:
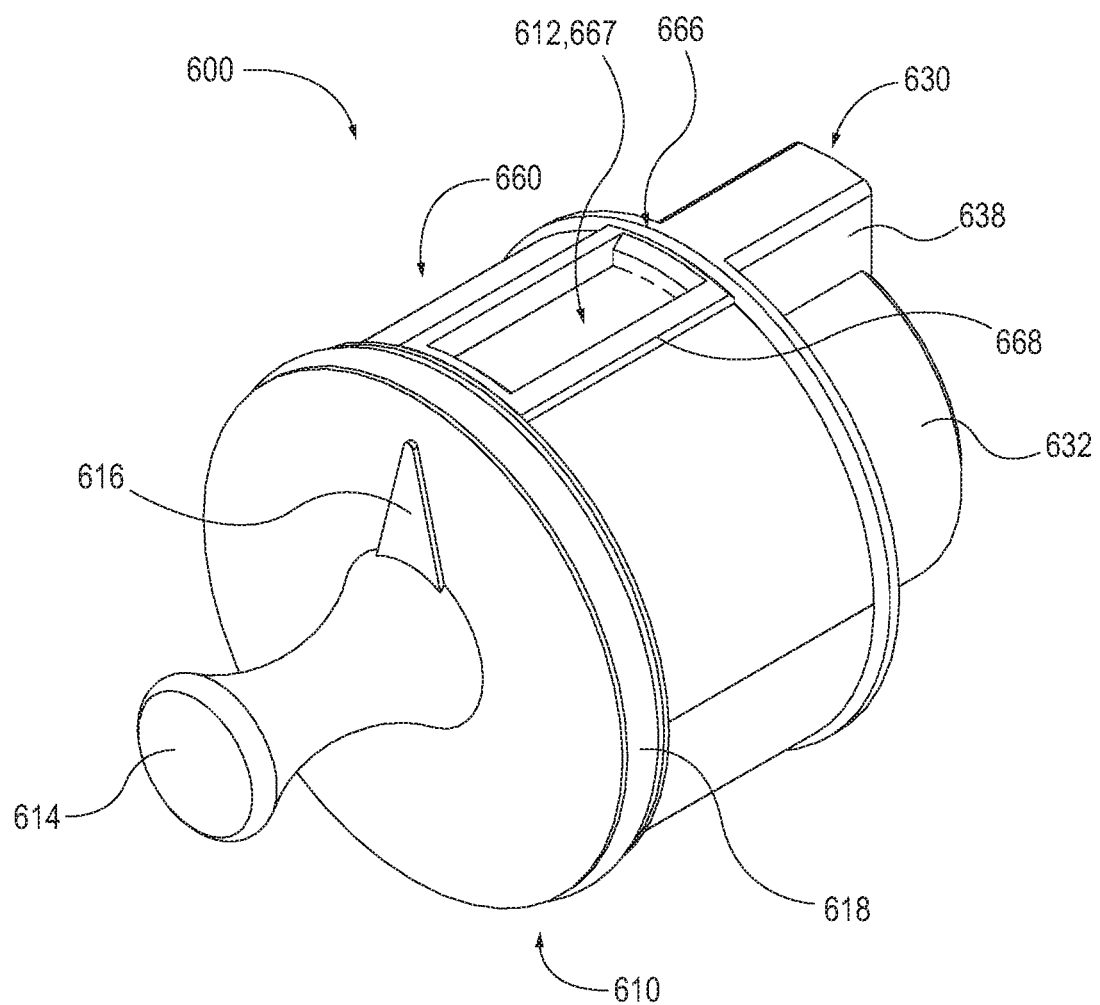
FIG. 17 depicts a perspective view of a bulk cup assembly of the tissue sample holder of FIG. 13.

FIG. 17 shows an exemplary bulk cup assembly (600). As can be seen, bulk cup assembly (600) comprises a body (610), a filter (630) and a removable top (660). As will be described in greater detail below, bulk cup assembly (600) is generally configured to align with passage (513) of rotatable member (510) to receive a plurality of tissue samples when passage (513) is aligned with lumen (151) of cutter (150). Body (610) is generally cylindrical in shape and is configured to be removably received within first cylindrical portion (522) of rotatable member (510). The cylindrical shape of body (610) defines a sample cavity (612). Cavity (612) is configured to receive a plurality of tissue samples. In the present example, cavity (612) is configured to receive 20 to 25 tissue samples, or as many as 30 tissue samples. Of course, in other examples cavity (612) is configured to receive any suitable number of tissue samples as will be apparent to those of ordinary skill in the art in view of the teachings herein.

The proximal end of body (610) includes a removal knob (614), a graphical indicator (616), and a seal (618). Knob (614) is configured to be grasped by an operator to facilitate removal of bulk cup assembly (600) from the proximal end of rotatable member (510). Indicator (616) is configured to indicate proper alignment of body (610) with rotatable member (510) when bulk cup assembly (600) is inserted into rotatable member (510). Seal (618) is configured to sealingly engage the interior of first cylindrical portion (522) to seal body (610) relative to the proximal end of rotatable member (510).

Figure 18:
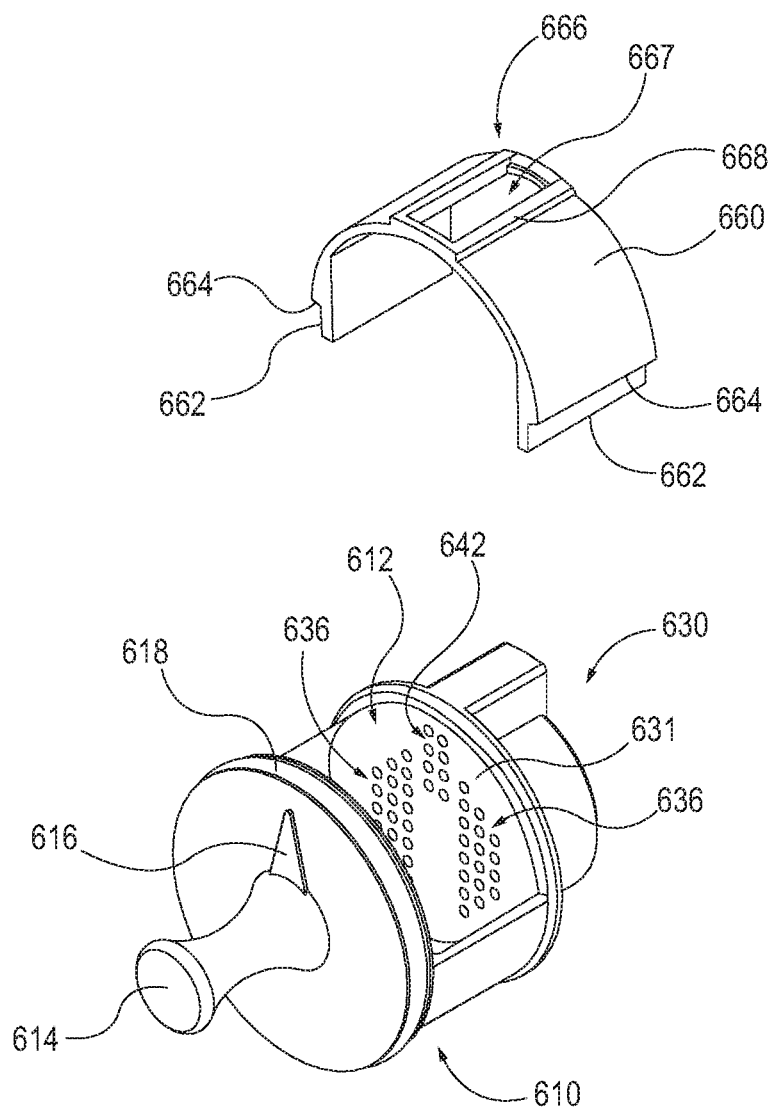
FIG. 18 depicts an exploded perspective view of the bulk cup assembly of FIG. 17.

As is best seen in FIG. 18, top (660) generally corresponds to the cylindrical shape of body (610). In the present example, top (660) defines approximately one half of the cylindrical shape of body (610), although top (660) defines any suitable amount of body (610) in other examples. Top (660) is removable from body (610) to provide access to cavity (612). As will be described in greater detail below, an operator may generally remove top (660) to remove tissue samples from cavity (612).

Top (660) comprises two engagement members (662) and a tissue communication port (666). Engagement members (662) extend downwardly from top (660) and are configured to engage the interior of body (610) to locate top (660) relative to body (610). Each engagement member (662) is indented relative to top (660) to define a shelf (664). Each shelf (664) extends laterally from engagement member (662) and is configured to rest on body (610). Thus, when top (660) is attached to body (610), each shelf (664) locates top (660) axially relative to body (610). Although not shown, it should be understood that in some examples engagement members (662) and/or shelves (664) include attachment features configured to selectively attach top (660) to body (610). In such examples, various suitable attachment features may be used such as snap fits, compression fittings, latches, and/or any other suitable attachment feature as will be apparent to those of ordinary skill in the art in view of the teachings herein.

Tissue communication port (666) is disposed at the upper most portion of top (660). Tissue communication port (666) of the present example defines a generally rectangular opening (667) in top (660) that is in communication with cavity (612) when top (660) is attached to body (610). As will be described in greater detail below, tissue communication port (666) is generally configured to align with passage (513) of rotatable member (510) such that cavity (612) may receive tissue samples when lumen (151) of cutter (150) is aligned with passage (513). Although opening (667) is shown as having a generally rectangular shape, it should be understood that in other examples numerous alternative shapes are used. For instance, in some examples, opening (667) is ovular, circular, triangular, or any other suitable shape as will be apparent to those of ordinary skill in the art in view of the teachings herein.

Tissue communication port (666) further includes a raised surface (668) surrounding the outer perimeter of opening (667). In particular, raised surface (668) protrudes from the outer surface of top (660). Raised surface (668) of the present example is configured to engage the interior of first cylindrical portion (522) of rotatable member (510) to thereby promote communication of fluid and tissue samples from passage (513) of rotatable member (510) to cavity (612) of body (610). It should be understood that raised surface (668) of the present example is merely optional and may be omitted in some examples.

Figure 19:
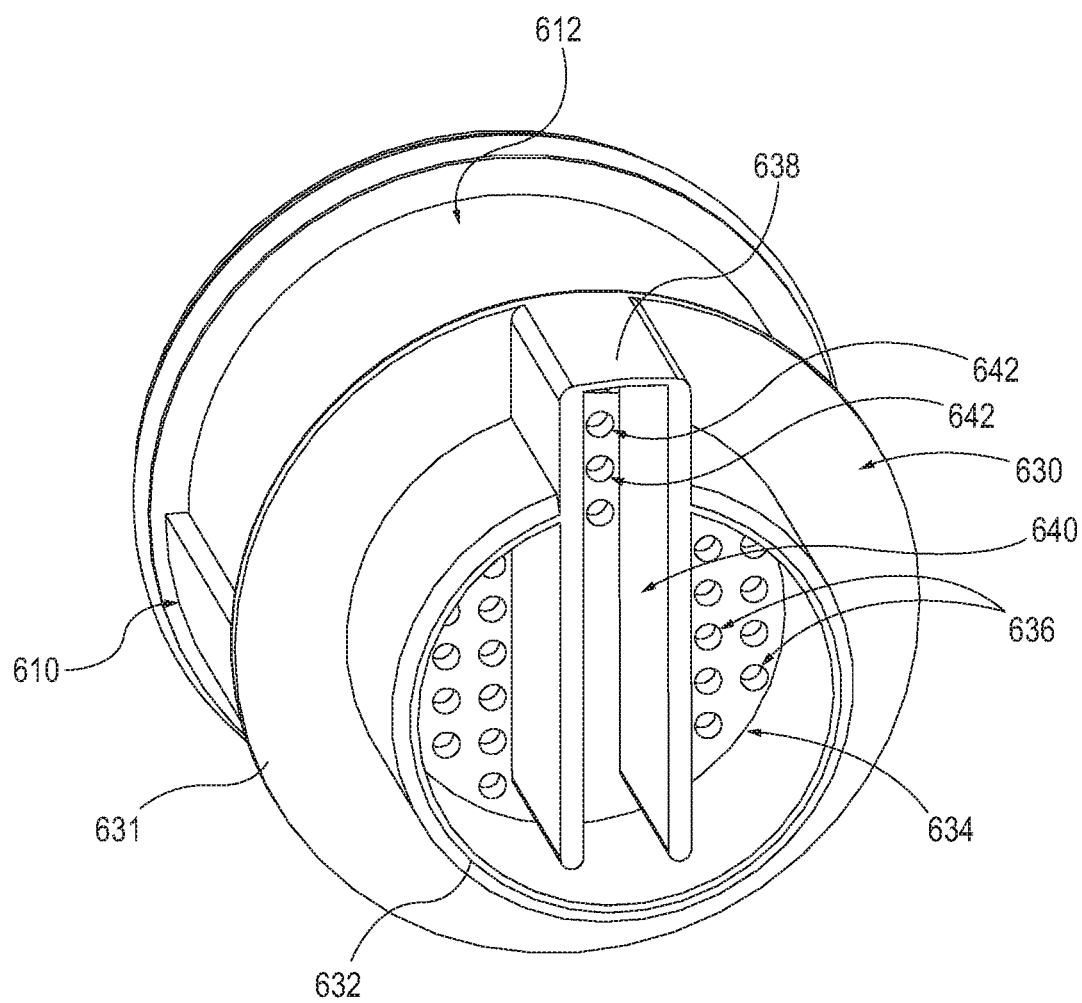
FIG. 19 depicts another perspective view of the bulk cup assembly of FIG. 17.

FIG. 19 shows filter (630) in greater detail. Filter (630) includes an end portion (631), a first fluid control member (632) and a second fluid control member (638). End portion (631) is integral with body (610) and is disposed on the distal end of body (610) adjacent to cavity (612). End portion (631) is generally configured to seal the distal end of body (610) such that cavity (612) may contain tissue samples. Additionally, as will be described in greater detail below, end portion (631) is generally configured to control the flow of fluid out of cavity (612).

First member (632) comprises a thin wall with a circular lateral cross-section extending distally from end portion (631). In particular, first member (632) defines a generally circular fluid chamber (634) and surrounds two sets of fluid openings (636) in end portion (631). As will be described in greater detail below, fluid chamber (634) is configured to permit some accumulation of fluid. As will also be described in greater detail below, openings (636) permit fluids but not tissue to pass though end portion (631) and into fluid chamber (634).

Second member (638) comprises a thin wall with a rectangular lateral cross-section extending distally from end portion (631). In particular, second member (638) defines a generally rectangular vacuum chamber (640) and surrounds a set of vacuum openings (642) in end portion (631). An upper portion of second member (638) extends through first member (632) such that a portion of vacuum chamber (640) extends into fluid chamber (634). As will be described in greater detail below, vacuum chamber (640) is configured to receive vacuum from biopsy device (10) and direct such a vacuum through vacuum openings (642) and into chamber (612) of body (610). As will also be described in greater detail below, vacuum chamber (640) is further configured to remove excessive fluid from fluid chamber (634) using vacuum from biopsy device (10).

Figure 20:
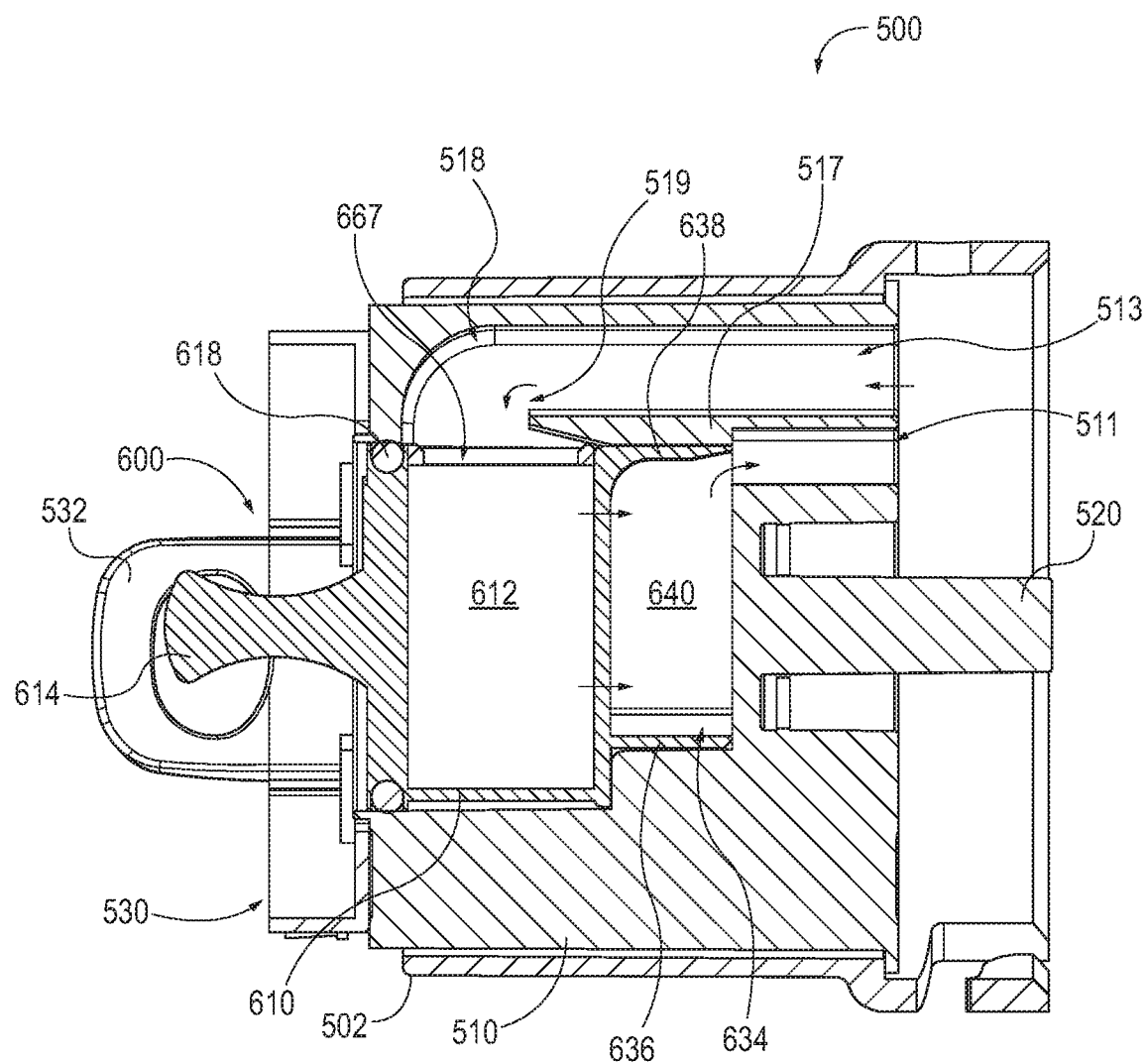
FIG. 20 depicts a side cross-sectional view of the tissue sample holder of FIG. 13, the cross-section taken along line 20-20 of FIG. 13.

FIG. 20 shows an exemplary fluid path through tissue sample holder (500) when tissue sample holder (500) is configured for bulk tissue collection. When tissue sample holder (500) is configured for bulk tissue collection, rotatable member (510) is rotatably oriented to position passage (513) in the twelve o'clock position such that passage (513) is positioned to communicate with cutter lumen (151) of cutter (150). Additionally, passage (511) is positioned to communicate with port (178) of biopsy device (10) to provide vacuum to passage (511).

With passage (511) positioned to receive vacuum from port (178), a air and liquid fluid as well as tissue samples may be pulled through passage (513). Once through passage, fluid and tissue samples collect in chamber (612) of bulk cup assembly (600). Gaseous fluid will pass through openings (636, 642) of filter (630) into vacuum chamber (640) and out of tissue sample holder (500) through passage (511).

Any liquid (e.g., blood, saline, etc.) passing through passage (513) and into chamber (612) may begin to accumulate in chamber. Excessive liquid will flow through fluid openings (636) of filter and begin to collect in fluid chamber (634). Once such excessive liquid has reached vacuum chamber (640) of filter (630), any excessive fluid will be vacuumed from vacuum chamber (640) through passage (511) and out of tissue sample holder (500).

While fluid may pass through fluid openings (636), it should be understood that any tissue samples will generally remain in chamber (612). In particular, each fluid opening (636) is sized smaller than any tissue sample, such that only fluid may flow through each opening (636).

As described above, bulk cup assembly (600) is configured to receive a plurality of tissue samples when aligned with lumen (151) of cutter (150). In particular, when used with biopsy device (10), bulk cup assembly (600) may be used by an operator using a variety of operational methods. In one merely exemplary use, an operator may select a bulk sample collection mode using control module (400). Control module (400) will then index rotatable member (510) relative to lumen (151) of cutter (150) to position passage (513) in the twelve o'clock position. Once passage (513) is in the twelve o'clock position, bulk cup assembly (600) is in communication with lumen (151) of cutter (150) via passage (513) to collect a plurality of successive tissue samples.

While biopsy device (10) is in the bulk sample collection mode, an operator may use biopsy device (10) to remove an entire cancerous lesion. During the removal process, if chamber (612) becomes full, an operator may remove bulk cup assembly (600) from rotatable member (510) and empty the contents of chamber (612). Once empty, an operator may continue removing tissue from a patient.

In an alternative use, an operator may use biopsy device (10) in an individual tissue collection mode. In some examples such a mode may be used diagnostic purposes to collect individual tissue samples for subsequent pathological testing. It should be understood that although the individual tissue collection mode is described herein as being used in connection with collection of tissue for pathological testing, such a mode should not be so limited. Furthermore, any other modes described herein may be used in connection with collection of tissue for pathological testing.

To transition biopsy device (10) to individual tissue collection mode, an operator may select such a mode using control module (400). Once individual tissue collection mode is selected, biopsy device (10) may collect tissue samples using tissue sample holder (500) as similarly described above with respect to tissue sample holder (300) (e.g., depositing a single tissue sample in successive tissue receiving trays (530)).

In still another alternative use, an operator may use biopsy device (10) in a combination mode by selecting such a mode using control module (400). When the combination mode is selected, biopsy device (10) may rotate rotatable member (510) after collection of one or more tissue samples to alternate between indexing passages (512) or passage (513) with lumen (151) of cutter (150). In this way, biopsy device (10) may alternate between being configured for collection of individual tissue samples and tissue samples in bulk.

By way of example only, in one implementation of combination mode, biopsy device (10) initially indexes one of passages (512) with lumen (151) of cutter (150). After collecting a sample, biopsy device (10) may then rotate rotatable member (510) to index passage (513) with lumen (151) of cutter (150). A predetermined number of tissue samples may then be collected into bulk cup assembly (600). Next, biopsy device (10) may rotate rotatable member (510) to index the next successive passage (512) with lumen (151) of cutter (150) and the process may repeat until the procedure is complete or all tissue receiving trays (530) are filled.

In another merely exemplary implementation of combination mode, biopsy device (10) initially indexes one of passages (512) with lumen (151) of cutter (150). Once a tissue sample is taken and deposited in the corresponding tissue receiving tray (530) an operator may determine whether another individual sample will be taken using the next successive tissue receiving tray (530); or whether sampling should shift to bulk cup assembly (600). Thus, in one implementation of combination mode, an operator is able to selectably alternate between individual tissue collection and bulk tissue collection as the biopsy procedure is performed. Such an implementation may be desirable to permit an operator to visually inspect tissue samples periodically to determine whether a lesion is being sampled. It should be understood while various implementations of combination mode are described herein, other suitable implementations will be apparent to those of ordinary skill in the art in view of the teachings herein.

Figure 21:
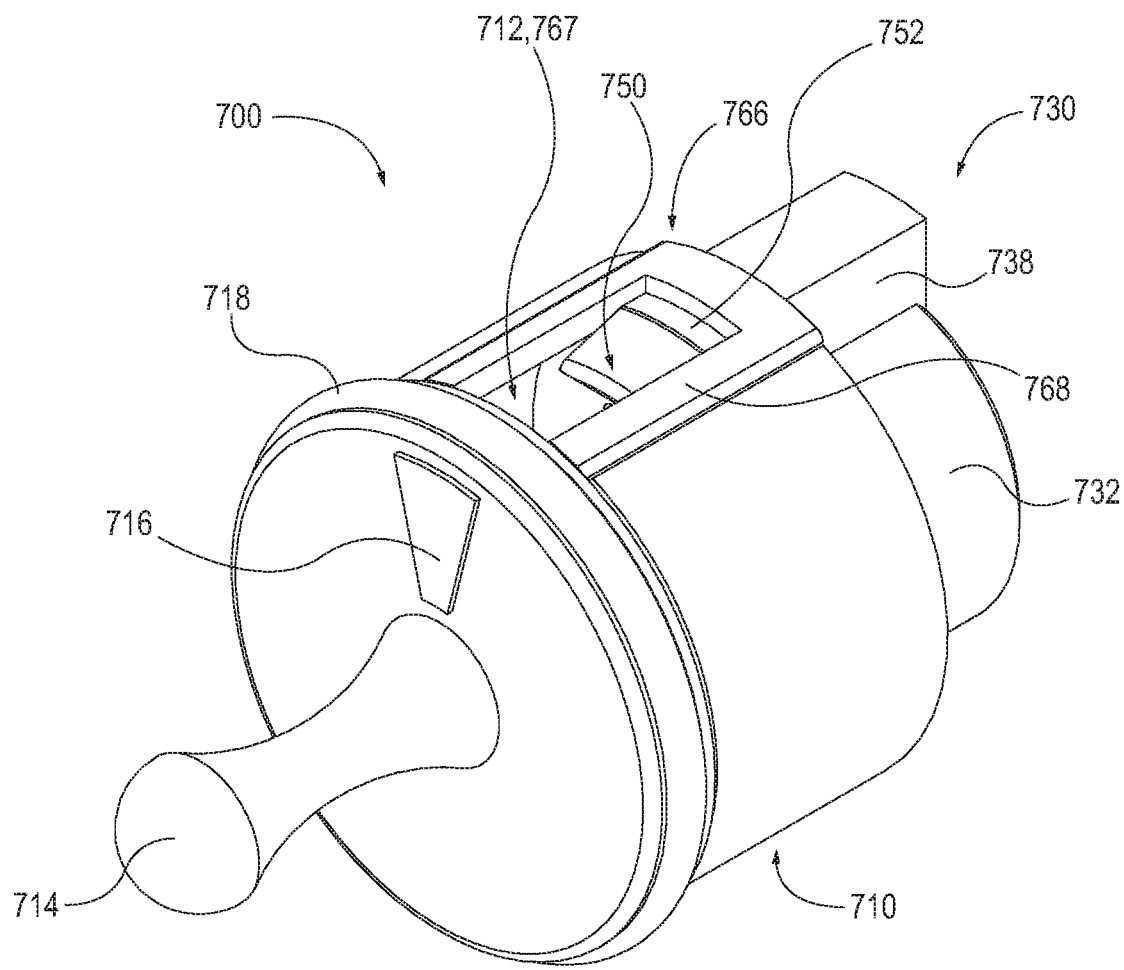
FIG. 21 depicts a perspective view of an exemplary alternative bulk cup assembly that may be readily incorporated into the tissue sample holder of FIG. 13.

FIG. 21 shows another exemplary alternative bulk cup assembly (700) that may be readily used with rotatable member (510) described above in lieu of bulk cup assembly (600). As can be seen, bulk cup assembly (700) comprises a body (710), and a detachable filter (730). Unlike bulk cup assembly (600) described above, bulk cup assembly (700) of the present example omits top. As will be described in greater detail below, bulk cup assembly (700) is generally configured to align with passage (513) of rotatable member (510) to receive a plurality of tissue samples when passage (513) is aligned with lumen (151) of cutter (150). Body (710) is generally cylindrical in shape and is configured to be removably received within first cylindrical portion (522) of rotatable member (510). The cylindrical shape of body (710) defines a sample cavity (712). Cavity (712) is configured to receive a plurality of tissue samples. In the present example, cavity (712) is configured to receive 20 to 25 tissue samples, or as many as 30 tissue samples. Of course, in other examples cavity (712) is configured to receive any suitable number of tissue samples as will be apparent to those of ordinary skill in the art in view of the teachings herein.

The proximal end of body (710) includes a removal knob (714), a graphical indicator (716), and a seal (718). Knob (714) is configured to be grasped by an operator to facilitate removal of bulk cup assembly (700) from the proximal end of rotatable member (510). Indicator (716) is configured to indicate proper alignment of body (710) with rotatable member (510) when bulk cup assembly (700) is inserted into rotatable member (510). Seal (718) is configured to sealingly engage the interior of first cylindrical portion (522) to seal body (710) relative to the proximal end of rotatable member (510).

Body (710) further includes a tissue communication port (766) disposed at the upper most portion of body (710). Tissue communication port (766) of the present example defines a generally rectangular opening (767) in body (710) that is in communication with cavity (712). As will be described in greater detail below, tissue communication port (766) is generally configured to align with passage (513) of rotatable member (510) such that cavity (712) may receive tissue samples when lumen (151) of cutter (150) is aligned with passage (513). Although opening (767) is shown as having a generally rectangular shape, it should be understood that in other examples numerous alternative shapes are used. For instance, in some examples, opening (767) is ovular, circular, triangular, or any other suitable shape as will be apparent to those of ordinary skill in the art in view of the teachings herein.

Tissue communication port (766) further includes a raised surface (768) surrounding the outer perimeter of opening (767). In particular, raised surface (768) protrudes from the outer surface of body (710). Raised surface (768) of the present example is configured to engage the interior of first cylindrical portion (522) of rotatable member (510) to thereby promote communication of fluid and tissue samples from passage (513) of rotatable member (510) to cavity (712) of body (710). It should be understood that raised surface (768) of the present example is merely optional and may be omitted in some examples.

Figure 22:
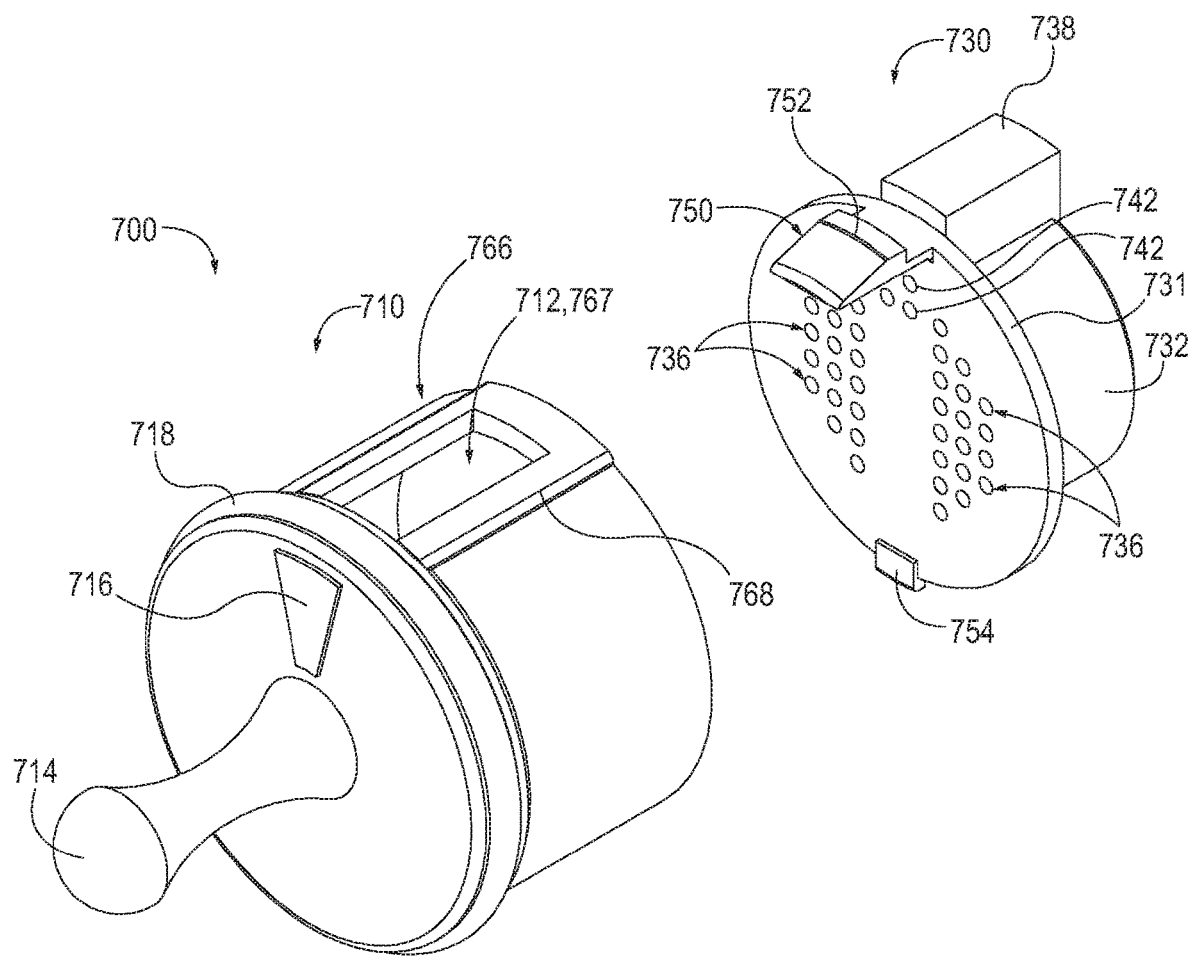
FIG. 22 depicts a perspective exploded view of the bulk cup assembly of FIG. 21.
Figure 23:
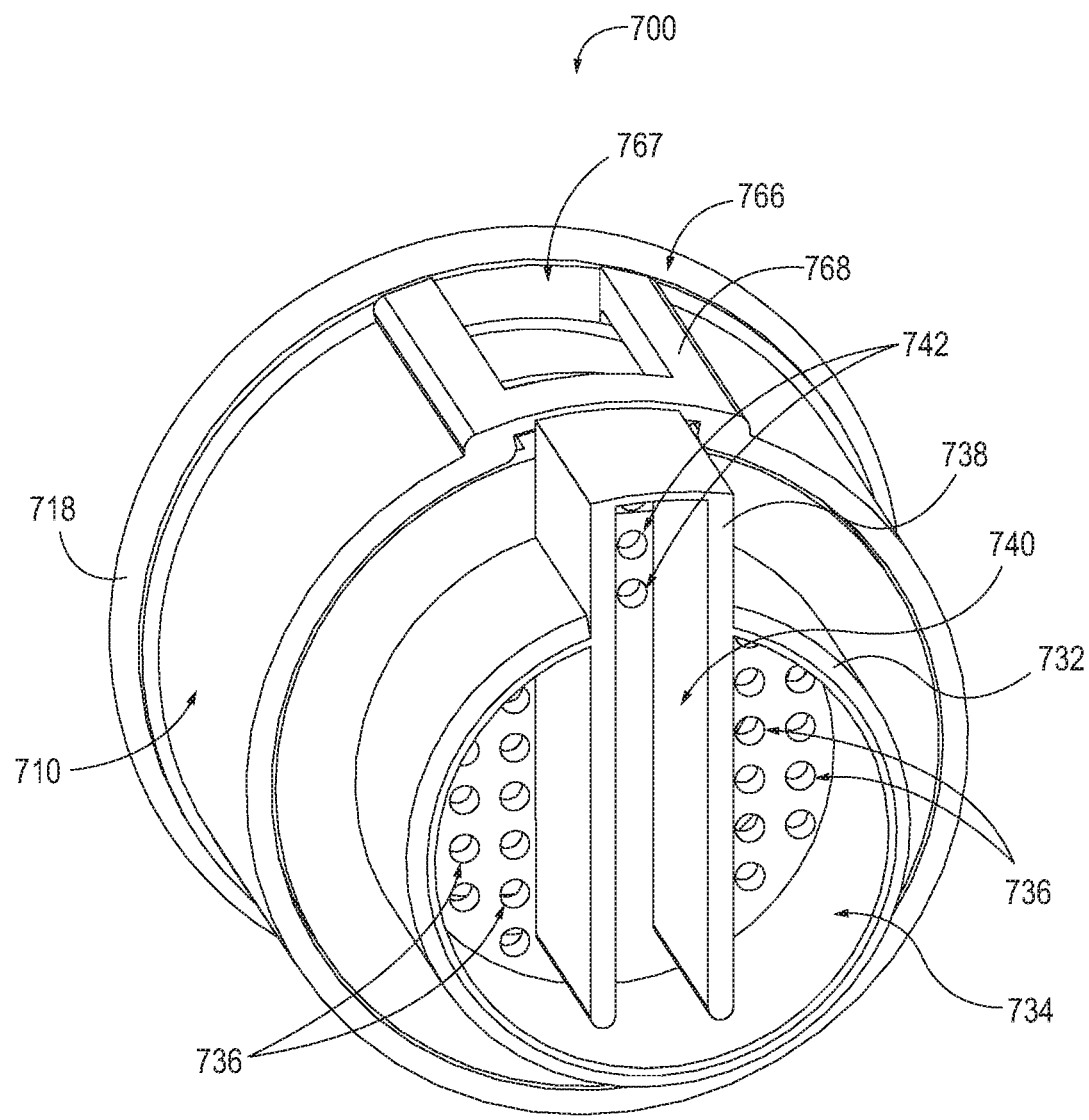
FIG. 23 depicts another perspective view of the bulk cup assembly of FIG. 21.

FIGS. 22 and 23 show filter (730) in greater detail. Filter (730) includes an end portion (731), a first fluid control member (732) and a second fluid control member (738). End portion (731) is detachable from body (710) and is selectively securable to the distal end of body (710) adjacent to cavity (712). Unlike end portion (631) described above, end portion (731) includes a first attachment member (750) and a second attachment member (754). Attachment members (750, 754) are generally configured to form a snap fit mechanism with body (710). In particular, first attachment member (750) is generally configured to be resiliently biased towards the position shown in FIG. 22. To facilitate fastening to body (710), first attachment member (750) includes a tooth (752) extending upwardly from first attachment member (750). Tooth (752) is configured to engage with opening (767) of tissue communication port (766) to selectively secure filter (730) to body.

Second attachment member (754) protrudes downwardly from end portion (731). Second attachment member (754) is generally rigid and is configured to engage a corresponding opening (719) (FIG. 24) in body (710). This permits second attachment member (754) to act as a mechanical ground for filter (730). Thus, when filter (730) is secured to body (710), second attachment member (754) is inserted into opening (719) of body (710). First attachment member (750) is then deflected inwardly as it is inserted into the distal end of body (710) until tooth (752) engages with opening (767) of tissue communication port (766), thereby permitting first attachment member (750) to return to the position shown in FIG. 22.

When end portion (731) is secured to body (710), end portion (731) is generally configured to seal the distal end of body (710) such that cavity (712) may contain tissue samples. Additionally, as will be described in greater detail below, end portion (731) is generally configured to control the flow of fluid out of cavity (712). Although not shown, it should be understood that in some examples bulk cup assembly (700) may include a seal at the interface between body (710) and end portion (731).

As best seen in FIG. 23, first member (732) of filter (730) comprises a thin wall with a circular lateral cross-section extending distally from end portion (731). In particular, first member (732) defines a generally circular fluid chamber (734) and surrounds two sets of fluid openings (736) in end portion (731). As will be described in greater detail below, fluid chamber (734) is configured to permit some accumulation of fluid. As will also be described in greater detail below, openings (736) permit fluids but not tissue to pass though end portion (731) and into fluid chamber (734).

Second member (738) comprises a thin wall with a rectangular lateral cross-section extending distally from end portion (731). In particular, second member (738) defines a generally rectangular vacuum chamber (740) and surrounds a set of vacuum openings (742) in end portion (731). An upper portion of second member (738) extends through first member (732) such that a portion of vacuum chamber (740) extends into fluid chamber (734). As will be described in greater detail below, vacuum chamber (740) is configured to receive vacuum from biopsy device (10) and direct such a vacuum through vacuum openings (742) and into chamber (712) of body (710). As will also be described in greater detail below, vacuum chamber (740) is further configured to remove excessive fluid from fluid chamber (734) using vacuum from biopsy device (10).

Figure 24:
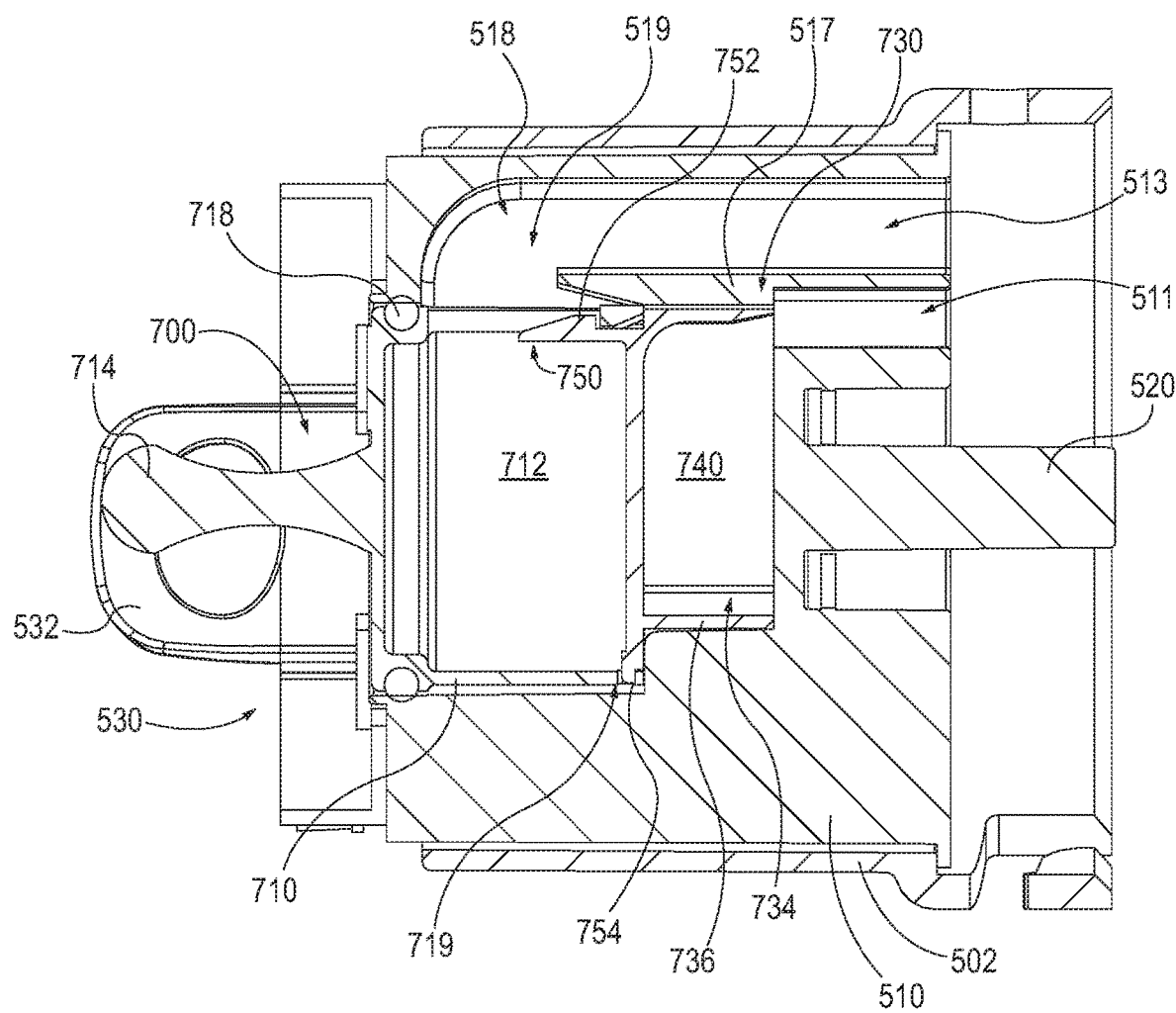
FIG. 24 depicts a side cross-sectional view of the tissue sample holder of FIG. 13, with the bulk cup assembly of FIG. 21 incorporated therein, the cross-section taken along line 20-20 of FIG. 13.

FIG. 24 shows an exemplary fluid path through tissue sample holder (500) when tissue sample holder (500) is equipped with bulk cup assembly (700) and is configured for bulk tissue collection. As similarly described above with respect to bulk cup assembly (600), when tissue sample holder (500) is configured for bulk tissue collection, rotatable member (510) is rotatably oriented to position passage (513) in the twelve o'clock position such that passage (513) is positioned to communicate with cutter lumen (151) of cutter (150). Additionally, passage (511) is positioned to communicate with port (178) of biopsy device (10) to provide vacuum to passage (511).

With passage (511) positioned to receive vacuum from port (178), a air and liquid fluid as well as tissue samples may be pulled through passage (513). Once through passage, fluid and tissue samples collect in chamber (712) of bulk cup assembly (700). Gaseous fluid will pass through openings (736, 742) of filter (730) into vacuum chamber (740) and out of tissue sample holder (500) through passage (511).

Any liquid (e.g., blood, saline, etc.) passing through passage (513) and into chamber (712) may begin to accumulate in chamber. Excessive liquid will flow through fluid openings (736) of filter and begin to collect in fluid chamber (734). Once such excessive liquid has reached vacuum chamber (740) of filter (730), any excessive fluid will be vacuumed from vacuum chamber (740) through passage (511) and out of tissue sample holder (500).

While fluid may pass through fluid openings (736), it should be understood that any tissue samples will generally remain in chamber (712). In particular, each fluid opening (736) is sized smaller than any tissue sample, such that only fluid may flow through each opening (736).

Figure 25:
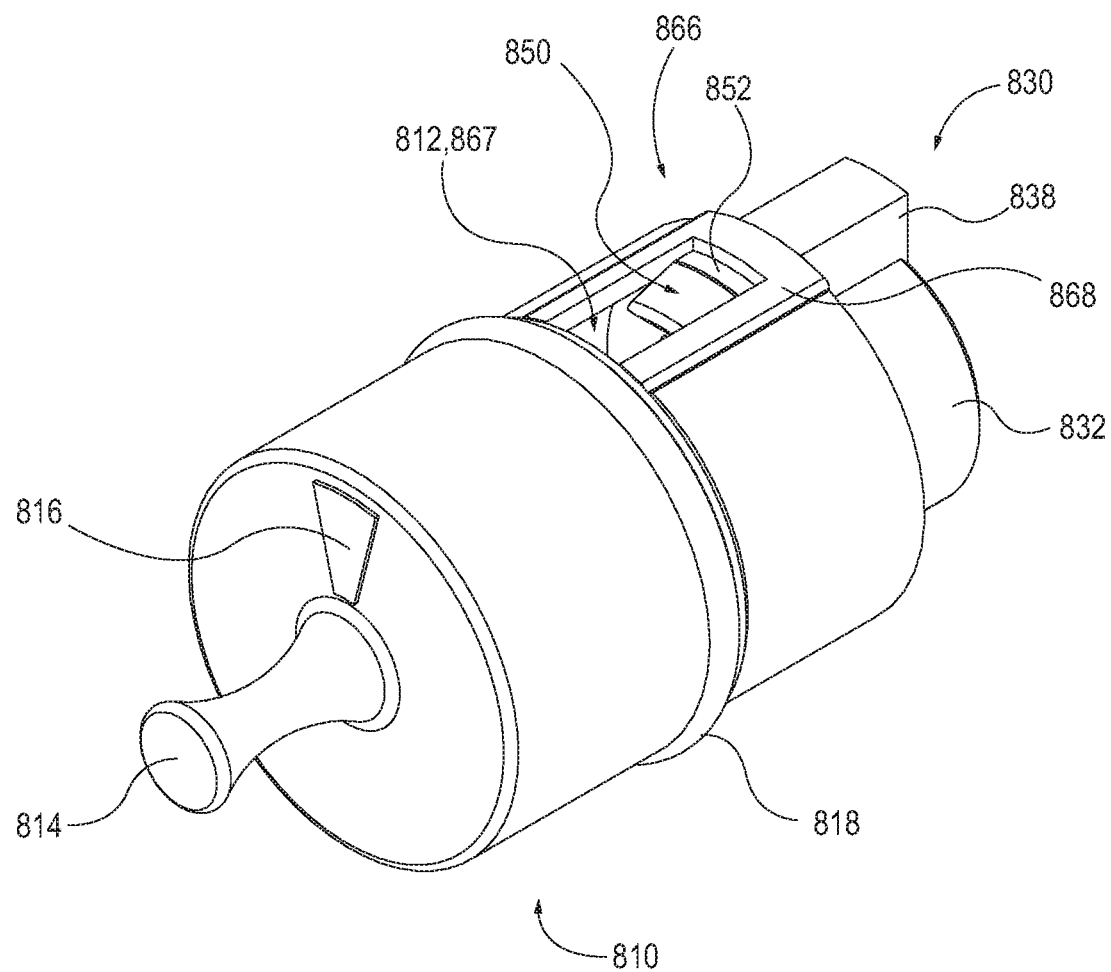
FIG. 25 depicts a perspective view of still another exemplary alternative bulk cup assembly that may be readily incorporated into the tissue sample holder of FIG. 13.

FIG. 25 shows still another exemplary alternative bulk cup assembly (800) that may be readily used with rotatable member (510) described above in lieu of bulk cup assemblies (600, 700). Bulk cup assembly (800) of the present example is substantially the same as bulk cup assembly (700) described above, except where otherwise noted herein. For instance, like bulk cup assembly (700) described above, bulk cup assembly (800) of the present example comprises a body (810), and a detachable filter (830). Also similarly to bulk cup assembly (700), bulk cup assembly (800) is generally configured to align with passage (513) of rotatable member (510) to receive a plurality of tissue samples when passage (513) is aligned with lumen (151) of cutter (150).

Body (810) is generally substantially similar to body (710) described above. For instance, body (810) is cylindrical in shape and is configured to be removably received within first cylindrical portion (522) of rotatable member (510). However, unlike body (710) described above, body (810) of the present example extends longitudinally for a longer length relative to body (710). This feature defines a sample cavity (812) that is substantially larger relative to cavity (712). In the present example, cavity (812) is configured to receive generally double the amount of tissue samples. For instance, while cavity (712) described above is configured to receive as many as 30 tissue samples, cavity (812) of the present example is configured to receive as many as 60 tissue samples. Of course, in other examples cavity (812) is configured to receive any suitable number of tissue samples as will be apparent to those of ordinary skill in the art in view of the teachings herein.

The proximal end of body (810) includes a removal knob (814), a graphical indicator (816), and a seal (818). Knob (814) is configured to be grasped by an operator to facilitate removal of bulk cup assembly (800) from the proximal end of rotatable member (510). Indicator (816) is configured to indicate proper alignment of body (810) with rotatable member (510) when bulk cup assembly (800) is inserted into rotatable member (510). Seal (818) is configured to sealingly engage the interior of first cylindrical portion (522) to seal body (810) relative to the proximal end of rotatable member (510). However, because body (810) is longer relative to body (710) described above, seal (818) of the present example is positioned further distally on body (810). Thus, when body (810) is inserted into rotatable member (510), at least some of body (810) will protrude from the proximal end of rotatable member (510).

Body (810) further includes a tissue communication port (866) disposed at the upper most portion of body (810). Tissue communication port (866) of the present example defines a generally rectangular opening (867) in body (810) that is in communication with cavity (812). As will be described in greater detail below, tissue communication port (866) is generally configured to align with passage (513) of rotatable member (510) such that cavity (812) may receive tissue samples when lumen (151) of cutter (150) is aligned with passage (513). Although opening (867) is shown as having a generally rectangular shape, it should be understood that in other examples numerous alternative shapes are used. For instance, in some examples, opening (867) is ovular, circular, triangular, or any other suitable shape as will be apparent to those of ordinary skill in the art in view of the teachings herein.

Tissue communication port (866) further includes a raised surface (868) surrounding the outer perimeter of opening (867). In particular, raised surface (868) protrudes from the outer surface of body (810). Raised surface (868) of the present example is configured to engage the interior of first cylindrical portion (522) of rotatable member (510) to thereby promote communication of fluid and tissue samples from passage (513) of rotatable member (510) to cavity (812) of body (810). It should be understood that raised surface (868) of the present example is merely optional and may be omitted in some examples.

Figure 26:
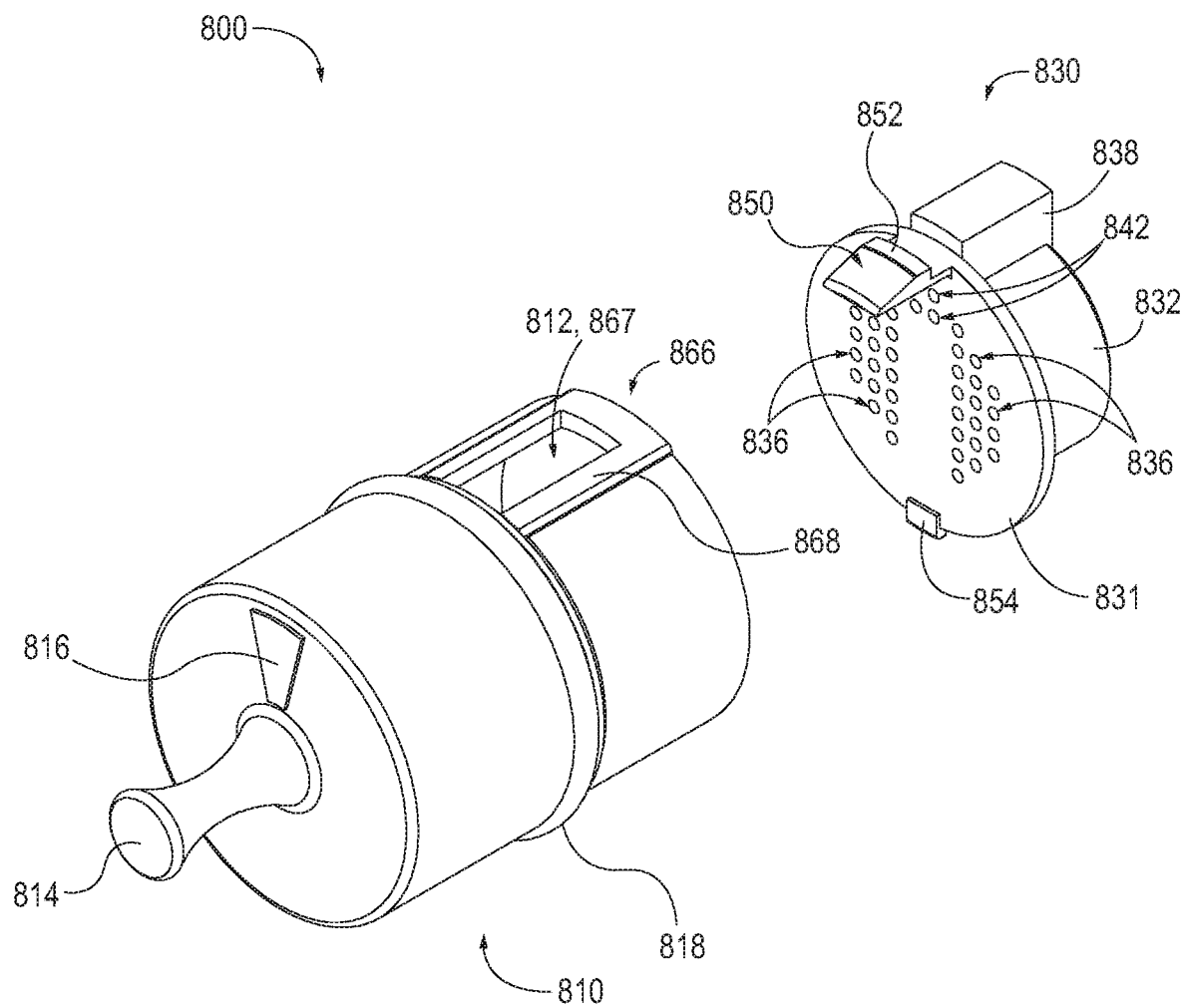
FIG. 26 depicts a perspective exploded view of the bulk cup assembly of FIG. 25.
Figure 27:
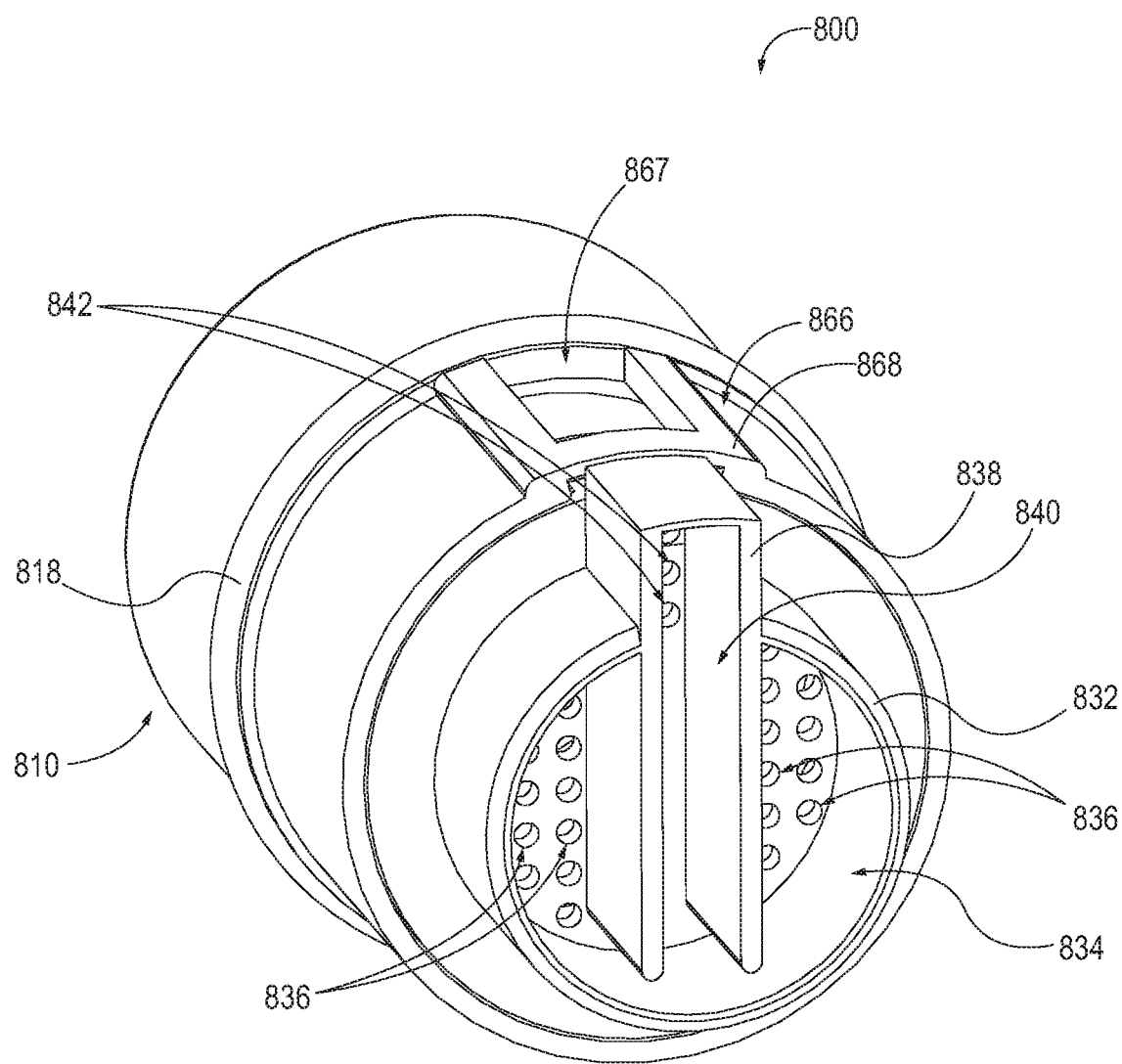
FIG. 27 depicts another perspective view of the bulk cup assembly of FIG. 25.

FIGS. 26 and 27 show filter (830) in greater detail. Filter (830) includes an end portion (831), a first fluid control member (832) and a second fluid control member (838). End portion (831) is detachable from body (810) and is selectively securable to the distal end of body (810) adjacent to cavity (812). Unlike end portion (731) described above, end portion (831) includes a first attachment member (850) and a second attachment member (854). Attachment members (850, 854) are generally configured to form a snap fit mechanism with body (810). In particular, first attachment member (850) is generally configured to be resiliently biased towards the position shown in FIG. 26. To facilitate fastening to body (810), first attachment member (850) includes a tooth (852) extending upwardly from first attachment member (850). Tooth (852) is configured to engage with opening (867) of tissue communication port (866) to selectively secure filter (830) to body.

Second attachment member (854) protrudes downwardly from end portion (831). Second attachment member (854) is generally rigid and is configured to engage a corresponding opening (819) (FIG. 28) in body (810). This permits second attachment member (854) to act as a mechanical ground for filter (830). Thus, when filter (830) is secured to body (810), second attachment member (854) is inserted into opening (819) of body (810). First attachment member (850) is then deflected inwardly as it is inserted into the distal end of body (810) until tooth (852) engages with opening (867) of tissue communication port (866), thereby permitting first attachment member (850) to return to the position shown in FIG. 26.

When end portion (831) is secured to body (810), end portion (831) is generally configured to seal the distal end of body (810) such that cavity (812) may contain tissue samples. Additionally, as will be described in greater detail below, end portion (831) is generally configured to control the flow of fluid out of cavity (812). Although not shown, it should be understood that in some examples bulk cup assembly (800) may include a seal at the interface between body (810) and end portion (831).

As best seen in FIG. 27, first member (832) of filter (830) comprises a thin wall with a circular lateral cross-section extending distally from end portion (831). In particular, first member (832) defines a generally circular fluid chamber (834) and surrounds two sets of fluid openings (836) in end portion (831). As will be described in greater detail below, fluid chamber (834) is configured to permit some accumulation of fluid. As will also be described in greater detail below, openings (836) permit fluids but not tissue to pass though end portion (831) and into fluid chamber (834).

Second member (838) comprises a thin wall with a rectangular lateral cross-section extending distally from end portion (831). In particular, second member (838) defines a generally rectangular vacuum chamber (840) and surrounds a set of vacuum openings (842) in end portion (831). An upper portion of second member (838) extends through first member (832) such that a portion of vacuum chamber (840) extends into fluid chamber (834). As will be described in greater detail below, vacuum chamber (840) is configured to receive vacuum from biopsy device (10) and direct such a vacuum through vacuum openings (842) and into chamber (812) of body (810). As will also be described in greater detail below, vacuum chamber (840) is further configured to remove excessive fluid from fluid chamber (834) using vacuum from biopsy device (10).

Figure 28:
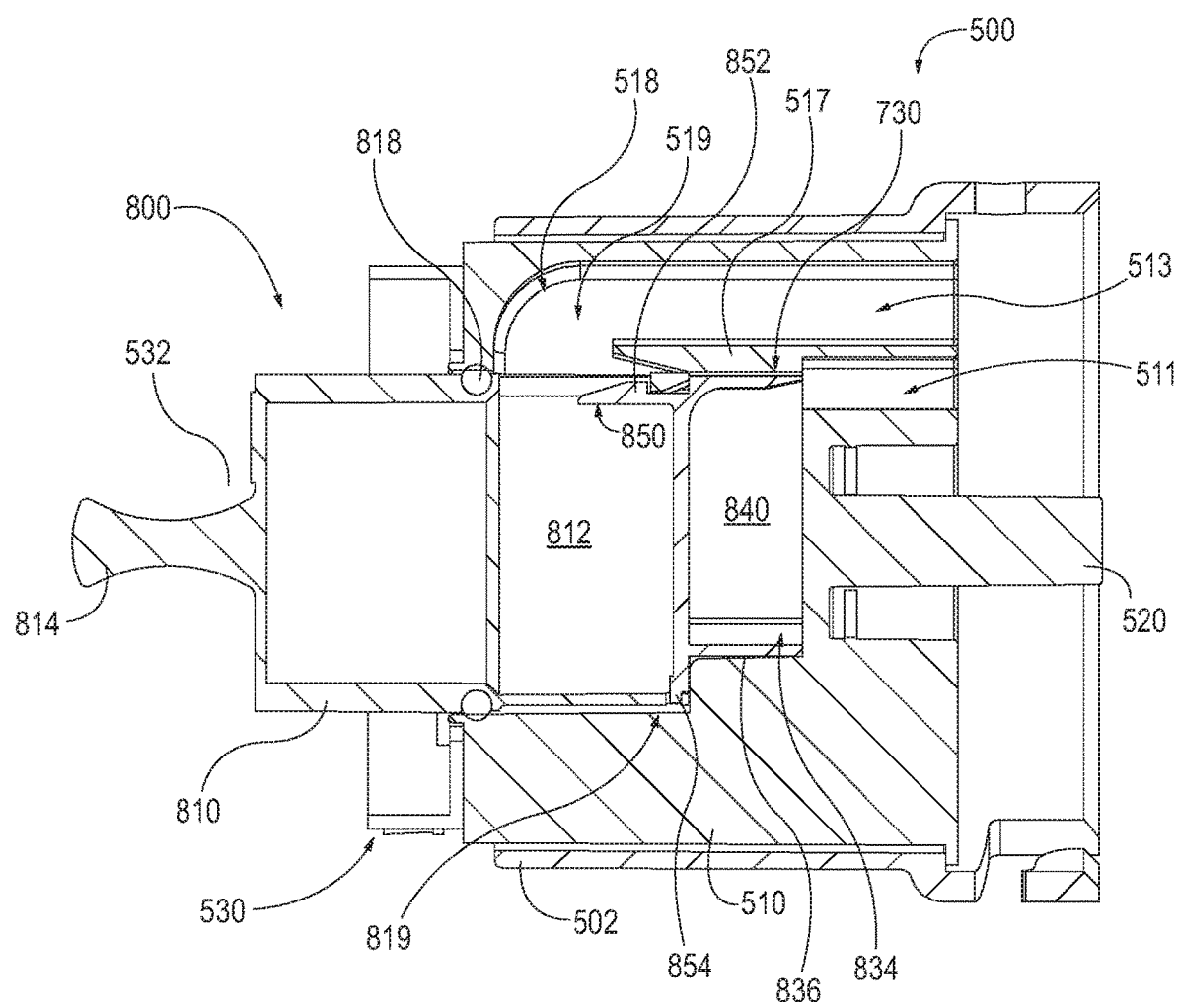
FIG. 28 depicts a side cross-sectional view of the tissue sample holder of FIG. 13, with the bulk cup assembly of FIG. 25 incorporated therein, the cross-section taken along line 20-20 of FIG. 13.
Figure 29:
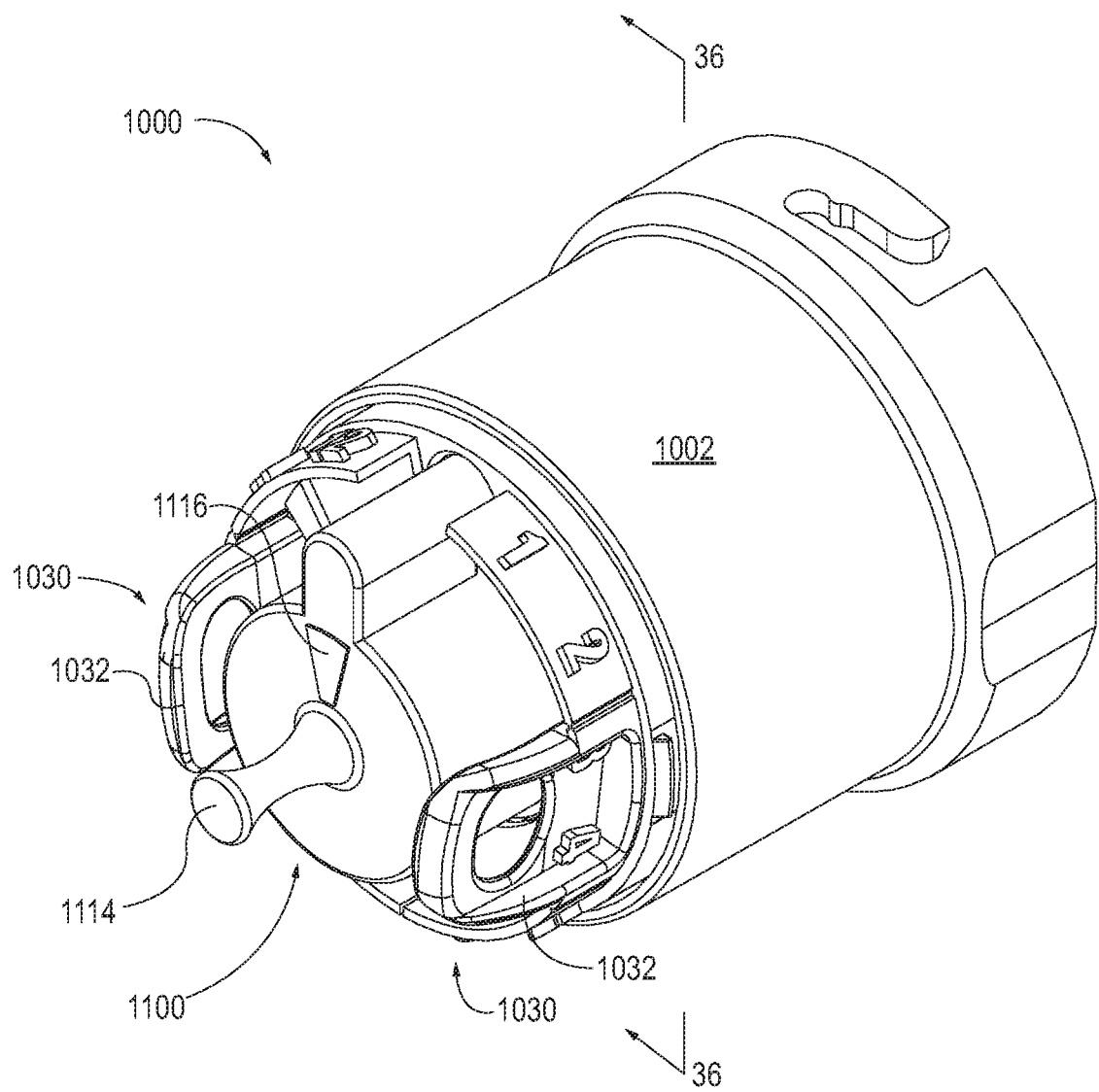
FIG. 29 depicts a perspective view of another exemplary alternative tissue sample holder for use with the biopsy device of FIG. 2.

FIG. 28 shows an exemplary fluid path through tissue sample holder (500) when tissue sample holder (500) is equipped with bulk cup assembly (800) and is configured for bulk tissue collection. As similarly described above with respect to bulk cup assemblies (600, 700), when tissue sample holder (500) is configured for bulk tissue collection, rotatable member (510) is rotatably oriented to position passage (513) in the twelve o'clock position such that passage (513) is positioned to communicate with cutter lumen (151) of cutter (150). Additionally, passage (511) is positioned to communicate with port (178) of biopsy device (10) to provide vacuum to passage (511).

With passage (511) positioned to receive vacuum from port (178), a air and liquid fluid as well as tissue samples may be pulled through passage (513). Once through passage, fluid and tissue samples collect in chamber (812) of bulk cup assembly (800). Gaseous fluid will pass through openings (836, 842) of filter (830) into vacuum chamber (840) and out of tissue sample holder (500) through passage (511).

Any liquid (e.g., blood, saline, etc.) passing through passage (513) and into chamber (812) may begin to accumulate in chamber. Excessive liquid will flow through fluid openings (836) of filter and begin to collect in fluid chamber (834). Once such excessive liquid has reached vacuum chamber (840) of filter (830), any excessive fluid will be vacuumed from vacuum chamber (840) through passage (511) and out of tissue sample holder (500).

While fluid may pass through fluid openings (836), it should be understood that any tissue samples will generally remain in chamber (812). In particular, each fluid opening (836) is sized smaller than any tissue sample, such that only fluid may flow through each opening (836).

FIGS. 29-32 show another exemplary alternative tissue sample holder (1000) that may be readily incorporated into biopsy device (10) as similarly described with respect to tissue sample holder (300) above. Unless otherwise indicated herein, it should be understood that tissue sample holder (1000) is substantially the same as tissue sample holder (500) described above. Like with tissue sample holder (500) described above, tissue sample holder (1000) of the present example provides a plurality of discrete chambers that are configured to receive tissue samples that are severed by cutter (150) and communicated proximally through lumen (151) of cutter (150). In particular, and as will be described in greater detail below, tissue sample holder (1000) includes tissue receiving trays (1030) that are removably engaged with a rotatable member (1010). Also like tissue sample holder (500) described above, tissue sample holder (1000) of the present example further includes a bulk cup assembly (1100) that is removably engaged with rotatable member (1010). As will be described in greater detail below, tissue sample holder (1000) of the present example is generally configured to permit an operator to selectably collect tissue samples in an individual tissue sample chamber or a bulk tissue sample collection chamber. However, unlike tissue sample holder (500) described above, tissue sample holder (1000) of the present example is generally configured to communicate with bulk cup assembly (1100) via the proximal end of rotatable member (1010).

As with rotatable member (510) described above, rotatable member (1010) is configured to be removably engaged with a grasping feature (184) of a rotation member (180). Rotation member (180) is longitudinally fixed relative to chassis (106) yet is rotatable relative to chassis (106). Rotation member (180) includes an integral gear (182), which meshes with gear (240) of holster (200) when probe (100) and holster (200) are coupled together. Gears (182, 240) cooperate to rotate rotatable member (510) to index tissue chambers relative to lumen (151) of cutter (150) as will be described in greater detail below. A transparent outer cup (1002) or cover is positioned about rotatable member (1010) and is configured to be removably secured to chassis (106). While bayonet features provide coupling between outer cup (1002) and chassis (106), it should be understood that any suitable type of coupling may be used. Rotatable member (1010) is freely rotatable within a chamber defined by outer cup (1002). However, rotatable member (1010) is engaged with outer cup (1002) such that rotatable member (1010) will decouple relative to chassis (106) when outer cup (1002) is removed from chassis (106). In other words, rotatable member (1010) may be selectively coupled with and removed relative to chassis (106) by coupling and removing outer cup (1002) from chassis (106).

Figure 30:
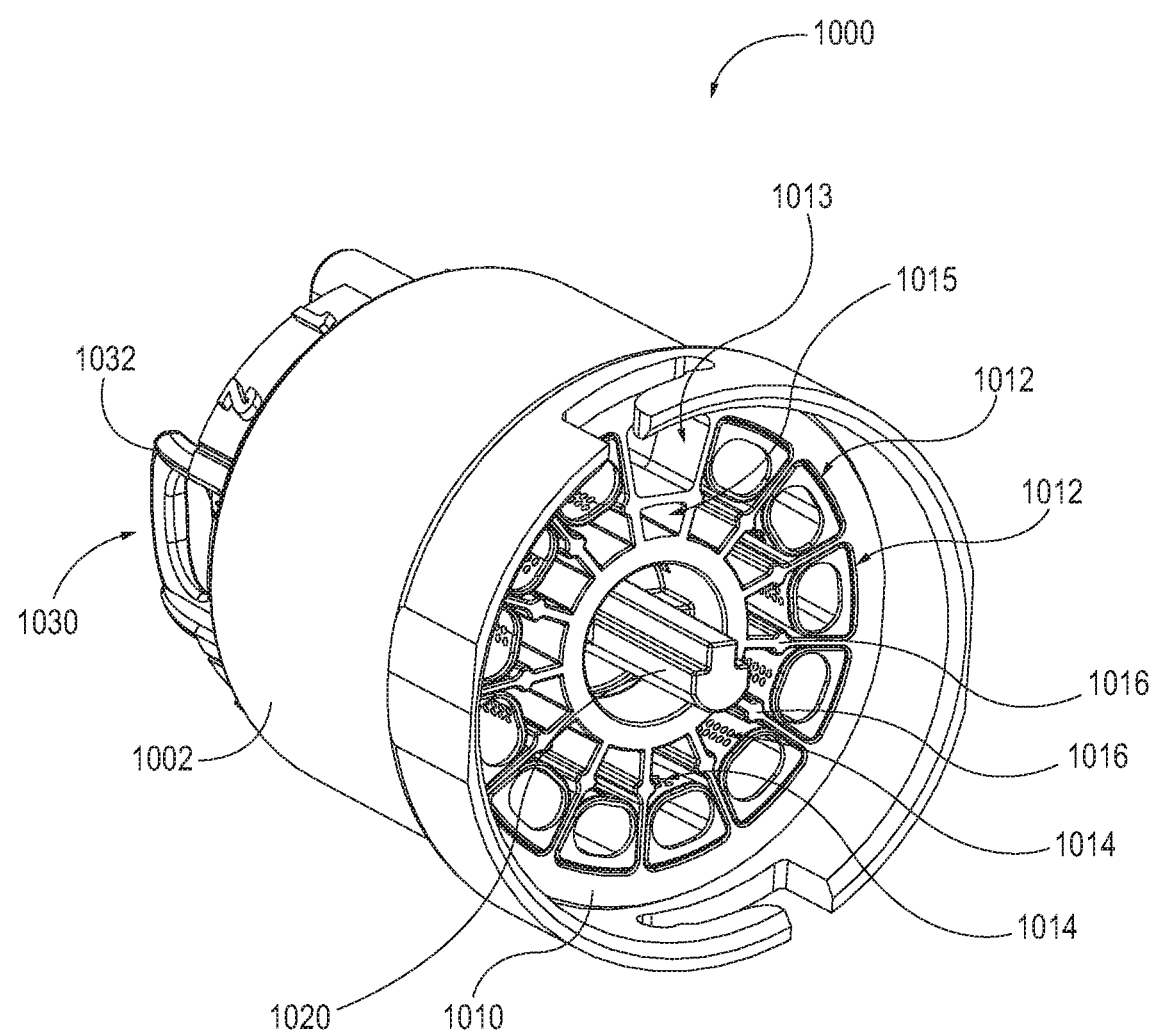
FIG. 30 depicts another perspective view of the tissue sample holder of FIG. 29.
Figure 31:
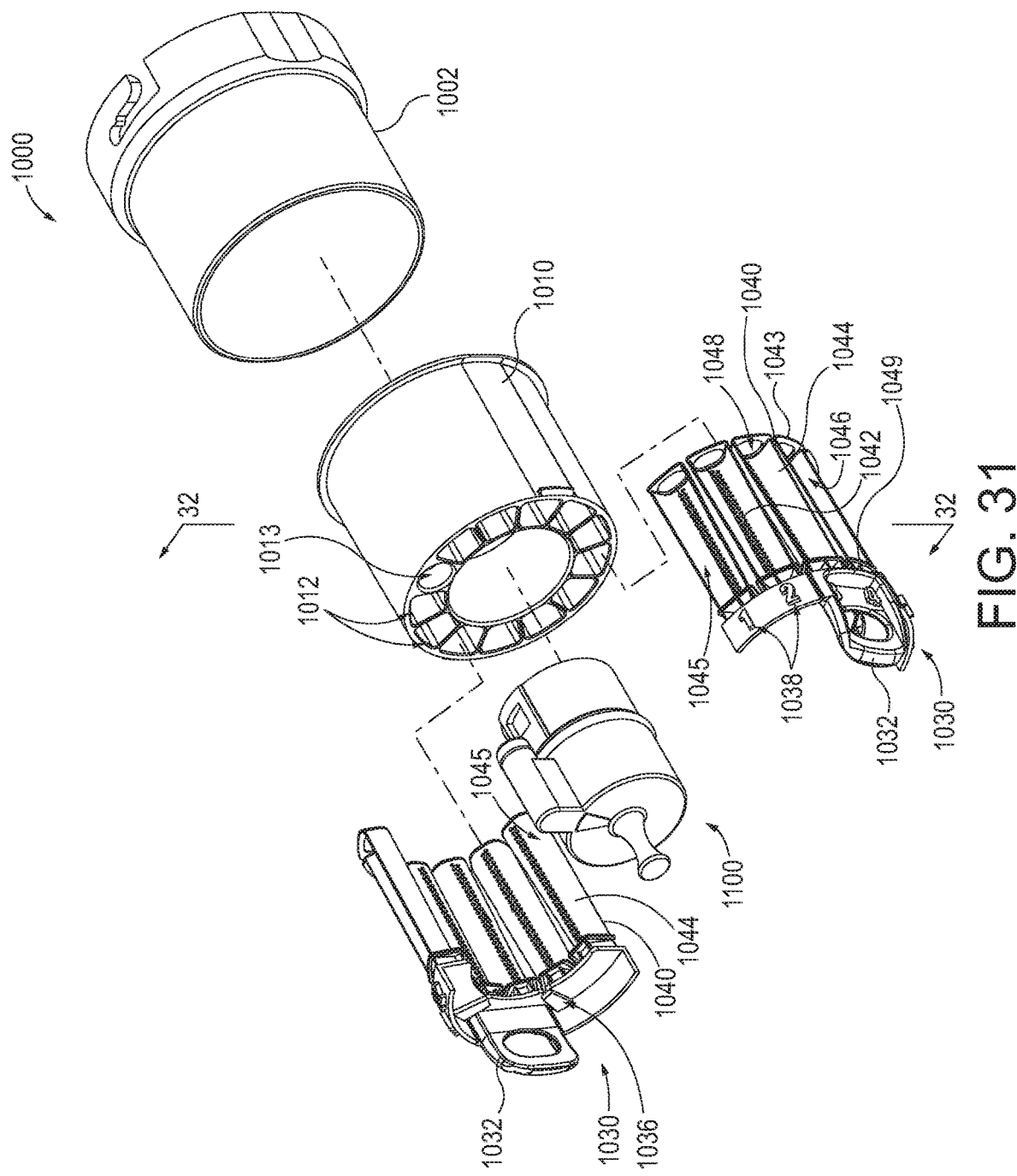
FIG. 31 depicts a perspective exploded view of the tissue sample holder of FIG. 29.

As best seen in FIGS. 30 and 31, rotatable member (1010) of the present example defines a plurality of chambers in the form of passages (1012) that extend longitudinally through rotatable member (1010) and that are angularly arrayed about the central axis of rotatable member (1010). Like with passages (512) described above, a lateral recess (1014) (FIG. 30) is associated with a distal portion of each passage (1012). Shelves (1016) demarcate boundaries between each passage (1012) and the associated lateral recess (1014). As will be described in greater detail below, passages (1012) receive trays (1030) while recesses (1014) provide pneumatic passages.

Similarly to rotatable member (510) described above, rotatable member (1010) includes an additional passage (1013) and recess (1015). Like passage (513) and recess (515) described above, passage (1013) and recess (1015) are not associated with a plug similar to plug (370). Instead, as will be described in greater detail below, passage (1013) and recess (1015) are configured to communicate tissue samples to bulk cup assembly (1100) when lumen (151) of cutter (150) is aligned with passage (1013).

Rotatable member (1010) also includes a central shaft (1020), which is configured to removably engage grasping feature (184). Central shaft (1020) is configured to couple with grasping feature (184) upon coupling of outer cup (1002) with chassis (106), as described above. Engagement between central shaft (1020) and grasping feature (184) provides rotation of rotatable member (1010) upon rotation of gear (182).

As noted above, tissue sample holder trays (1030) are configured to removably engage rotatable member (1010). Each tissue sample holder tray (1030) of the present example includes a grip (1032), a proximal wall (1034), and a plurality of strips (1040) extending distally from proximal wall (1034). Strips (1040) are sized and configured for insertion into associated passages (1012) of rotatable member (1010). Each strip (1040) includes a pair of sidewalls (1044) and a floor (1042). Each pair of sidewalls (1044) and floor (1042) together define a corresponding tissue sample chamber (1046). An opening (1048) is provided at the distal end of each tissue sample chamber (1046). Opening is sized and positioned to correspond with opening (174) of sealing member (170). Thus, the lumen (151) of cutter (150) is in fluid communication with the tissue sample chamber (1046) of the strip (1040) inserted in the passage (1012) that is at the 12 o'clock position. Strips (1040) are configured such that the distal portion of each strip (1040) receives support from a corresponding shelf (1016) of rotatable member (1010). Each floor (1042) includes a plurality of openings (1045) that provide fluid communication between tissue sample chamber (1046) of strip (1040) and lateral recess (1014) of the passage (1012) associated with strip (1040). Thus, vacuum, atmospheric air, etc. that is communicated to opening (176) via tube (20) is further communicated to lumen (151) of cutter (150) via lateral recess (1014), openings (1045), and tissue sample chamber (1046). During operation of biopsy device (10), tissue samples severed by distal edge (152) of cutter (150) are communicated proximally through the lumen (151) of cutter (150) and are then deposited into the tissue sample chamber (1046) that is aligned with lumen (151) of cutter (150). Rotatable member (1010) is rotated to successively align tissue sample chambers (1046) with lumen (151) of cutter (150), enabling several tissue samples to be separately deposited in different tissue sample chambers (1046) during operation of biopsy device (10). Bodily fluids and saline, etc. that are pulled through lumen (151) will pass through tissue sample holder (1000) and tube (20) and are eventually deposited in vacuum canister (70).

Each strip (1040) also includes a pair of wiper seals (1043, 1049) that seal against the interior of passage (1012) when strip (1040) is fully inserted into passage (1012). Wiper seals (1043, 1049) provide a fluid tight seal for tissue sample chambers (1046) and further provide frictional resistance to removal of strips (1040) from rotatable member (1010). Grips (1032) are configured to facilitate removal of strips (1040) from rotatable member (1010), such as during or after a biopsy procedure to retrieve or otherwise directly observe tissue samples deposited in tissue sample chambers (1046). Trays (1030) also include numerical indicia (1038) associated with each tissue sample chamber (1046). In addition, trays (1030) include pinched regions (1036) that facilitate flattening of trays (1030). In particular, pinched regions (1036) provide sufficient flexibility to enable trays (1030) to form an arcuate configuration for insertion into rotatable member (1010); while also enabling trays (1030) to form a generally flat configuration such as after trays (1030) are removed from rotatable member (1010) for inspection of tissue samples in trays (1030).

Figure 32:
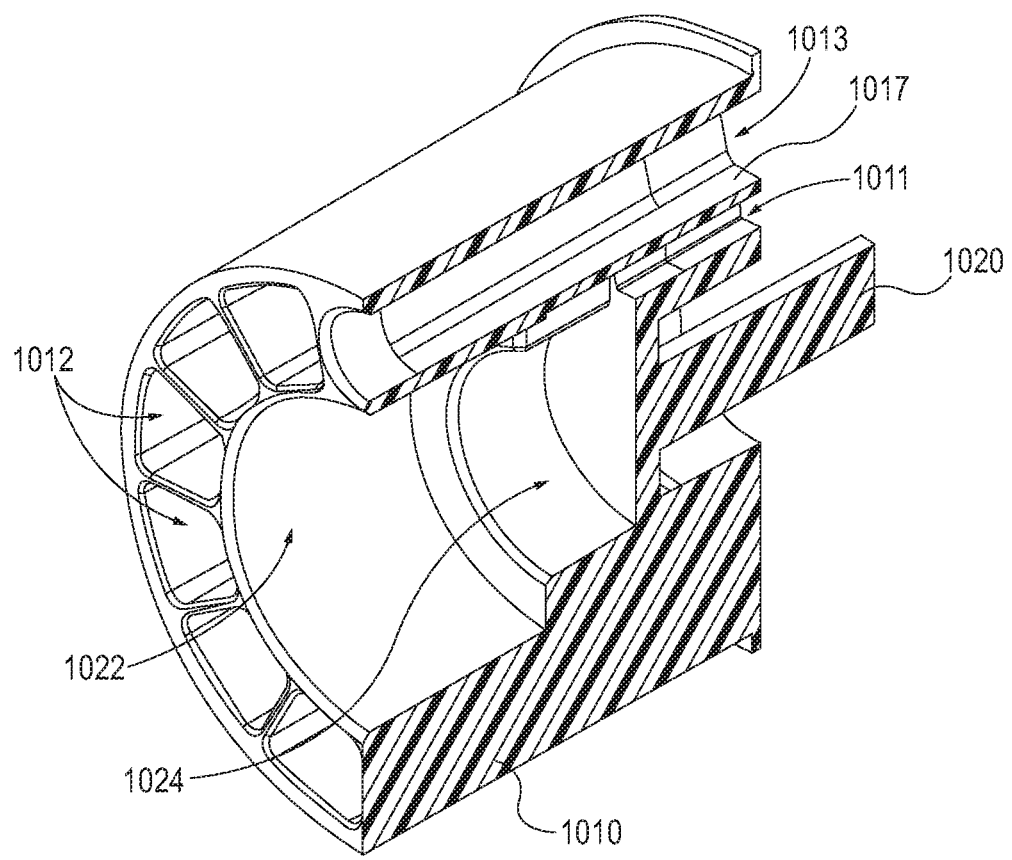
FIG. 32 depicts a perspective cross-sectional view of a rotatable member of the tissue sample holder of FIG. 29, the cross-section taken along line 32-32 of FIG. 31.

Like rotatable member (510) described above, rotatable member (1010) of the present example includes passage (1013) in addition to passages (1012). Also like passage (513) of rotatable member (510), passage (1013) of the present example is configured to communicate fluids from lumen (151) of cutter (150) to the interior of rotatable member (1010). In particular, as can be seen in FIG. 32, passage extends longitudinally though rotatable member (1010). However, unlike passage (513), passage (1013) of the present example includes an open proximal end (1018) that opens to the proximal end of rotatable member (1010). Adjacent to passage (1013) is a shelf (1017). Shelf (1017) also extends longitudinally though rotatable member (1010), and terminates at the proximal end of rotatable member (1010). As will be described in greater detail below, this configuration is configured to permit bulk cup assembly (1100) to couple to rotatable member (1010) at the proximal end thereof.

Shelf (1017) further defines a vacuum passage (1011) disposed below shelf (1017). Vacuum passage (1011) extends longitudinally through rotatable member (1010) and is in communication with the interior of rotatable member (1010). As will be described in greater detail below, passage (1013) is configured to communicate tissue samples from lumen (151) of cutter (150) to the interior of rotatable member (1010), while passage (1011) is configured to communicate vacuum from biopsy device (10) to the interior of rotatable member (1010).

The interior of rotatable member (1010) defines a first cylindrical portion (1022) and a second cylindrical portion (1024). As will be described in greater detail below, cylindrical portions (1022, 1024) are configured to receive a bulk cup assembly (1100) such that passage (1013) may be used to collect multiple tissue samples in a bulk collection mode. In the present example, first cylindrical portion (1022) is in adjacent to proximal end of rotatable member (1010), while second cylindrical portion (1024) is in communication with passage (1011). First cylindrical portion (1022) is further open to the proximal end of rotatable member (1010) such that first cylindrical portion (1022) is in communication with the exterior of rotatable member (1010). First cylindrical portion (1022) of the present example has a generally greater diameter than the diameter of second cylindrical portion (1024). Although cylindrical portions (1022, 1024) of the present example are shown as discrete portions of rotatable member (1010), it should be understood that in other examples, cylindrical portions (1022, 1024) are consolidated into a single cylindrical portion. Additionally, although cylindrical portions (1022, 1024) are described herein as having a generally cylindrical shape, in other examples any other suitable shape is used.

Figure 33:
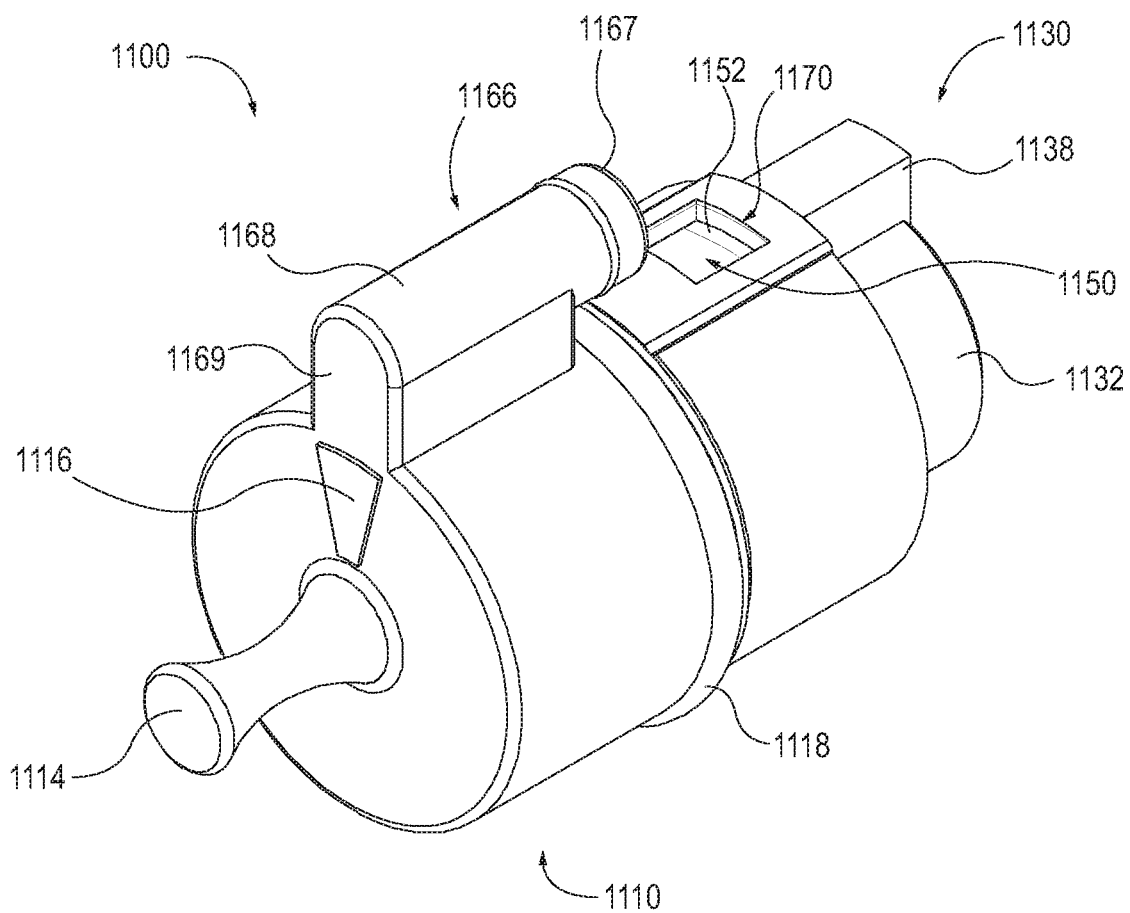
FIG. 33 depicts a perspective view of a bulk cup assembly of the tissue sample holder of FIG. 29.

FIG. 33 shows an exemplary alternative bulk cup assembly (1100) that may be readily used with rotatable member (1010) described above. Bulk cup assembly (1100) of the present example is substantially the same as bulk cup assembly (800) described above, except where otherwise noted herein. For instance, like bulk cup assembly (800) described above, bulk cup assembly (1100) of the present example comprises a body (1110), and a detachable filter (1130). However, unlike bulk cup assembly (800), bulk cup assembly (1100) is generally configured to align with passage (1013) of rotatable member (1010) via the proximal end of rotatable member (1010) instead of from within the interior of rotatable member (1010).

Body (1110) is generally similar to body (810) described above. For instance, body (1110) is cylindrical in shape and is configured to be removably received within first cylindrical portion (1022) of rotatable member (1010). Additionally, like body (810) described above, body (1110) of the present example extends longitudinally for a longer length relative to body (710). This feature defines a sample cavity (1112) that is substantially larger relative to cavity (712). In the present example, cavity (1112) is configured to receive generally double the amount of tissue samples. For instance, while cavity (712) described above is configured to receive as many as 30 tissue samples, cavity (1112) of the present example is configured to receive as many as 60 tissue samples. Of course, in other examples cavity (1112) is configured to receive any suitable number of tissue samples as will be apparent to those of ordinary skill in the art in view of the teachings herein.

The proximal end of body (1110) includes a removal knob (1114), a graphical indicator (1116), and a seal (1118). Knob (1114) is configured to be grasped by an operator to facilitate removal of bulk cup assembly (1100) from the proximal end of rotatable member (1010). Indicator (1116) is configured to indicate proper alignment of body (1110) with rotatable member (1010) when bulk cup assembly (1100) is inserted into rotatable member (1010). Seal (1118) is configured to sealingly engage the interior of first cylindrical portion (1022) to seal body (1110) relative to the proximal end of rotatable member (1010). However, because body (1110) is longer relative to body (710) described above, seal (1118) of the present example is positioned further distally on body (1110). Thus, when body (1110) is inserted into rotatable member (1010), at least some of body (1110) will protrude from the proximal end of rotatable member (1010).

Unlike body (810) described above, body (1110) further includes a proximal tissue communication port (1166). Tissue communication port (1166) is disposed at the upper most portion of body (1110). Tissue communication port (1166) of the present example defines a cylindrical portion (1168) disposed on top of a lateral tissue receiving portion (1169). The distal end of cylindrical portion (1168) includes an open distal end (1167). Distal end (1167) is configured to be received within passage (1013) of rotatable member (1010) to communicate tissue samples from passage (1013) to cavity (1112).

Body (1110) further includes an opening (1170) disposed at the upper most portion of body (1110). Opening (1170) of the present example is generally rectangular in shape and is in communication with cavity (1112). However, unlike opening (867) described above, opening (1170) of the present example is not configured to align with passage (1013) of rotatable member (1010). Instead, opening (1170) of the present example is merely configured to receive a portion of filter (1130) to selectively lock filter (1130) to body (1110).

Figure 34:
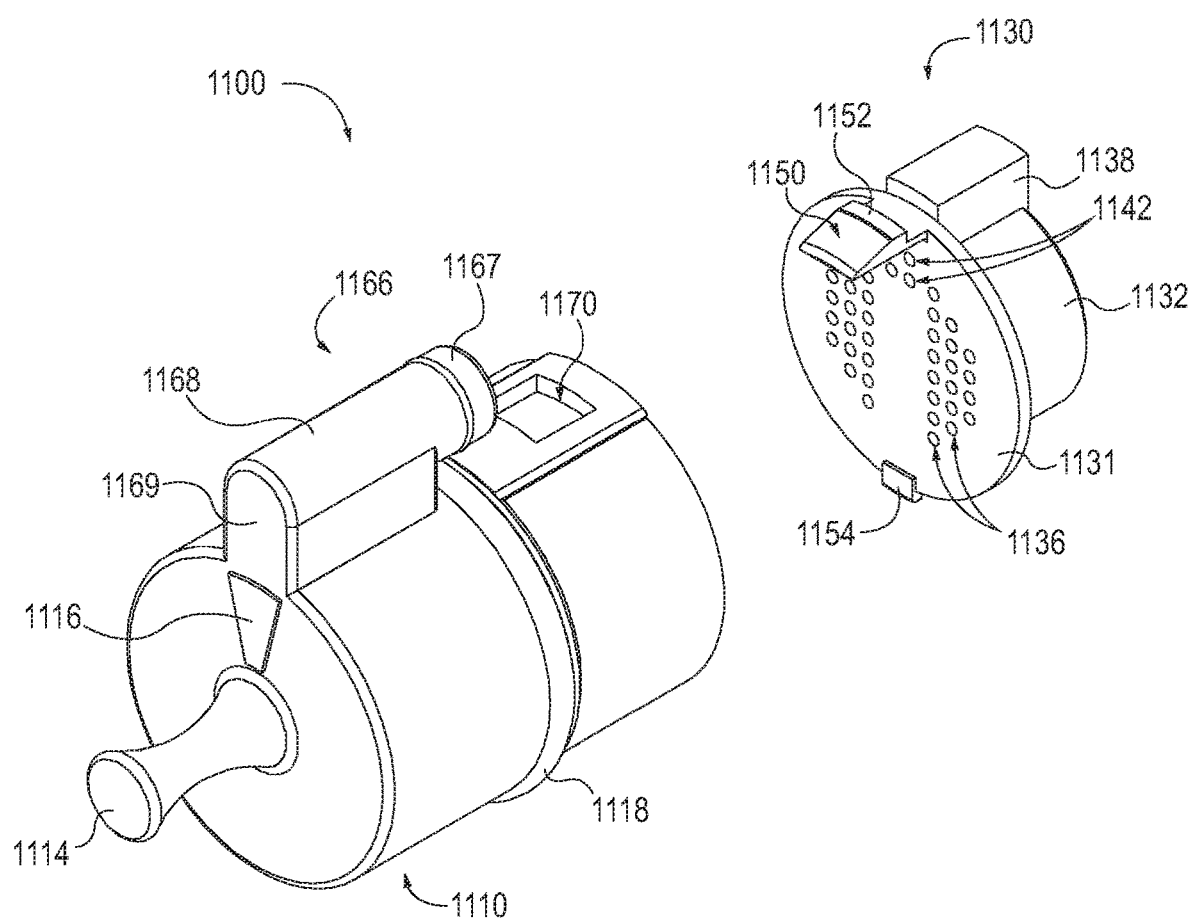
FIG. 34 depicts an exploded perspective view of the bulk cup assembly of FIG. 33.
Figure 35:
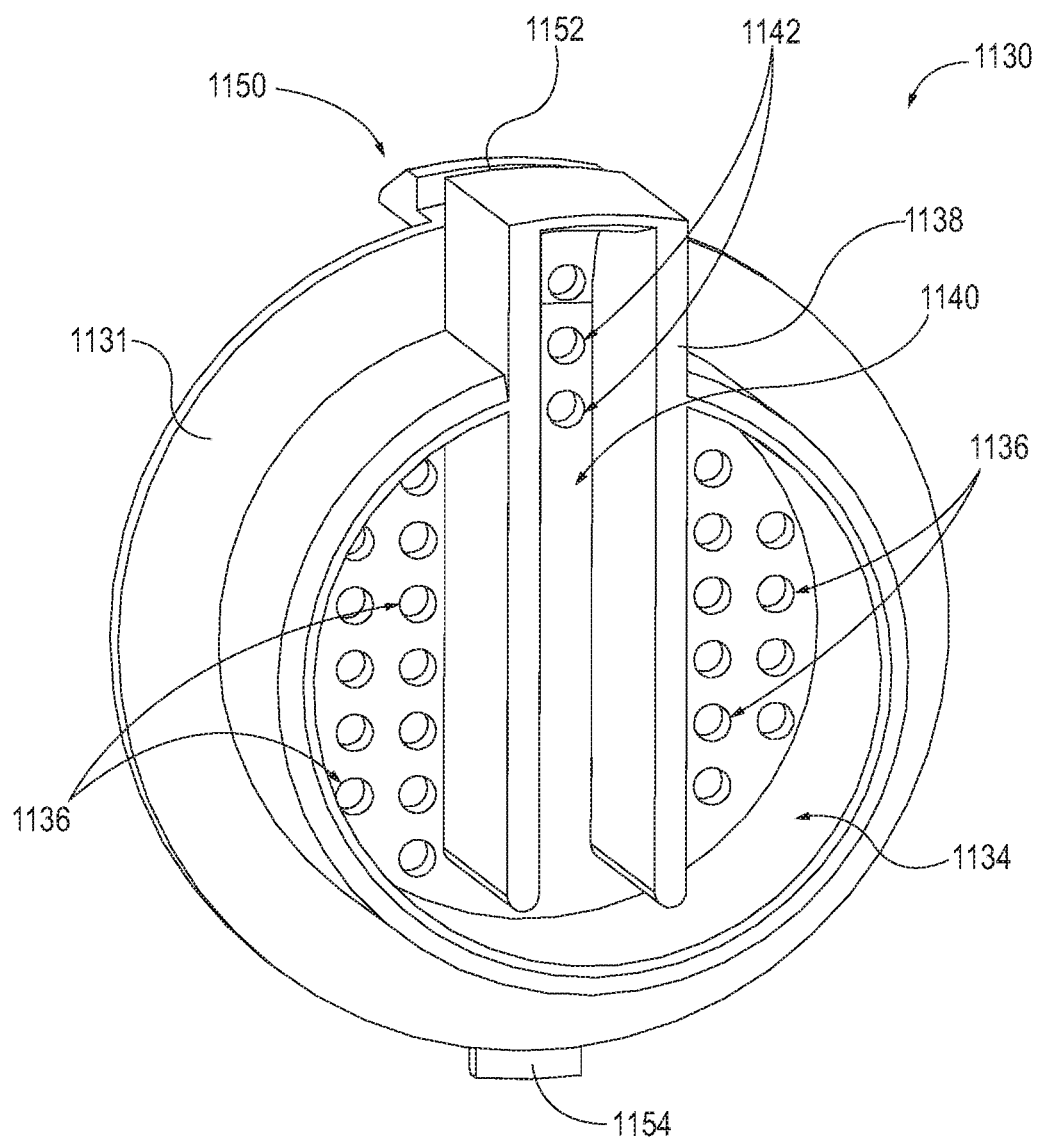
FIG. 35 depicts a perspective view of a filter of the bulk cup assembly of FIG. 33.

FIGS. 34 and 35 show filter (1130) in greater detail. Filter (1130) includes an end portion (1131), a first fluid control member (1132) and a second fluid control member (1138).

End portion (1131) is detachable from body (1110) and is selectively securable to the distal end of body (1110) adjacent to cavity (1112). Unlike end portion (631) described above, end portion (1131) includes a first attachment member (1150) and a second attachment member (1154). Attachment members (1150, 1154) are generally configured to form a snap fit mechanism with body (1110). In particular, first attachment member (1150) is generally configured to be resiliently biased towards the position shown in FIG. 34. To facilitate fastening to body (1110), first attachment member (1150) includes a tooth (1152) extending upwardly from first attachment member (1150). Tooth (1152) is configured to engage with opening (1170) of tissue communication port (1166) to selectively secure filter (1130) to body.

Second attachment member (1154) protrudes downwardly from end portion (1131). Second attachment member (1154) is generally rigid and is configured to engage a corresponding opening (1119) (FIG. 36) in body (1110). This permits second attachment member (1154) to act as a mechanical ground for filter (1130). Thus, when filter (1130) is secured to body (1110), second attachment member (1154) is inserted into opening (1119) of body (1110). First attachment member (1150) is then deflected inwardly as it is inserted into the distal end of body (1110) until tooth (1152) engages with opening (1170) of tissue communication port (1166), thereby permitting first attachment member (1150) to return to the position shown in FIG. 34.

When end portion (1131) is secured to body (1110), end portion (1131) is generally configured to seal the distal end of body (1110) such that cavity (1112) may contain tissue samples. Additionally, as will be described in greater detail below, end portion (1131) is generally configured to control the flow of fluid out of cavity (1112). Although not shown, it should be understood that in some examples bulk cup assembly (1100) may include a seal at the interface between body (1110) and end portion (1131).

As best seen in FIG. 35, first member (1132) of filter (1130) comprises a thin wall with a circular lateral cross-section extending distally from end portion (1131). In particular, first member (1132) defines a generally circular fluid chamber (1134) and surrounds two sets of fluid openings (1136) in end portion (1131). As will be described in greater detail below, fluid chamber (1134) is configured to permit some accumulation of fluid. As will also be described in greater detail below, openings (1136) permit fluids but not tissue to pass though end portion (1131) and into fluid chamber (1134).

Second member (1138) comprises a thin wall with a rectangular lateral cross-section extending distally from end portion (1131). In particular, second member (1138) defines a generally rectangular vacuum chamber (1140) and surrounds a set of vacuum openings (1142) in end portion (1131). An upper portion of second member (1138) extends through first member (1132) such that a portion of vacuum chamber (1140) extends into fluid chamber (1134). As will be described in greater detail below, vacuum chamber (1140) is configured to receive vacuum from biopsy device (10) and direct such a vacuum through vacuum openings (1142) and into chamber (1112) of body (1110). As will also be described in greater detail below, vacuum chamber (1140) is further configured to remove excessive fluid from fluid chamber (1134) using vacuum from biopsy device (10).

Figure 36:
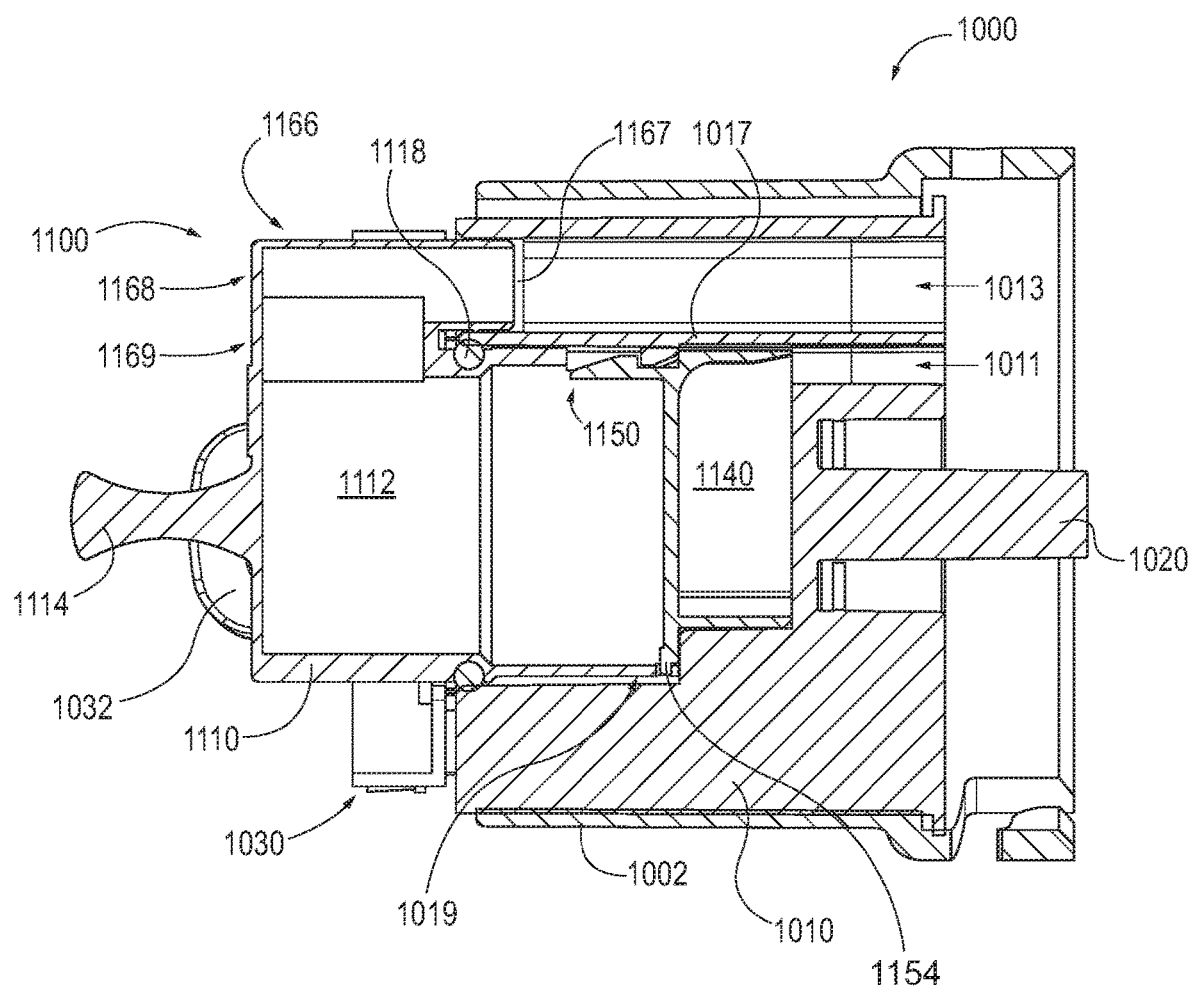
FIG. 36 depicts a side cross-sectional view of the tissue sample holder of FIG. 29, the cross-section taken along line 36-36 of FIG. 29.

FIG. 36 shows an exemplary fluid path through tissue sample holder (1000) when tissue sample holder (1000) is equipped with bulk cup assembly (1100) and is configured for bulk tissue collection. As similarly described above with respect to bulk cup assemblies (600, 700, 800), when tissue sample holder (1000) is configured for bulk tissue collection, rotatable member (1010) is rotatably oriented to position passage (1013) in the twelve o'clock position such that passage (1013) is positioned to communicate with cutter lumen (151) of cutter (150). Additionally, passage (511) is positioned to communicate with port (178) of biopsy device (10) to provide vacuum to passage (1011).

With passage (1011) positioned to receive vacuum from port (178), a air and liquid fluid as well as tissue samples may be pulled through passage (1013). Once through passage, fluid and tissue samples pass through cylindrical portion (1168) and lateral tissue receiving portion (1169) of tissue communication port (1166) before collecting in chamber (1112) of bulk cup assembly (1100). Gaseous fluid will pass through openings (1136, 1142) of filter (1130) into vacuum chamber (1140) and out of tissue sample holder (1000) through passage (1011).

Any liquid (e.g., blood, saline, etc.) passing through passage (1013) and into chamber (1112) may begin to accumulate in chamber. Excessive liquid will flow through fluid openings (1136) of filter and begin to collect in fluid chamber (1134). Once such excessive liquid has reached vacuum chamber (1140) of filter (1130), any excessive fluid will be vacuumed from vacuum chamber (1140) through passage (1011) and out of tissue sample holder (1000).

While fluid may pass through fluid openings (1136), it should be understood that any tissue samples will generally remain in chamber (1112). In particular, each fluid opening (1136) is sized smaller than any tissue sample, such that only fluid may flow through each opening (1136).

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A biopsy device comprising:
    (a) a body;
    (b) a needle extending distally from the body;
    (c) a cutter longitudinally translatable relative to the needle, the cutter defining a cutter lumen; and
    (d) a tissue sample holder including,
        (i) a rotatable member, the rotatable member defining a plurality of passages and a central portion defined by the plurality of passages,
        (ii) a tissue receiving tray including a plurality of strips, each strip of the plurality of strips being insertable into a corresponding passage of the plurality of passages, and
        (iii) a bulk cup assembly for receiving a plurality of tissue samples from the cutter, the bulk cup assembly being insertable into the central portion of the rotatable member.

2. The biopsy device of claim 1, the bulk cup assembly including a body and a filter, the body defining a tissue collection chamber.

3. The biopsy device of claim 2, the bulk cup assembly further including a removable top, at least a portion of the removable top partially defining the tissue collection chamber, the removable top being configured to be selectively removable from the cup body to provide operator access to the tissue collection chamber.

4. The biopsy device of claim 2, the filter being selectively removable from the body.

5. The biopsy device of claim 4, the filter including a resilient feature, the resilient feature being configured to selectively secure the filter to the body.

6. The biopsy device of claim 2, the filter including a plurality of filter openings, the plurality of filter openings being in communication with the tissue collection chamber, each filter opening of the plurality of filter openings being configured to prevent passage of tissue samples through the filter.

7. The biopsy device of claim 1, the bulk cup assembly extending proximally of the rotatable member when the bulk cup assembly is inserted in the central portion of the rotatable member.

8. The biopsy device of claim 1, a body of the bulk cup assembly being disposed entirely within the rotatable member when the bulk cup assembly is inserted in the central portion of the rotatable member.

9. The biopsy device of claim 1, the rotatable member defining a rotation axis, the plurality of passages, and the central portion being coaxial with the rotation axis.

10. The biopsy device of claim 1, the bulk cup assembly including a seal, the seal being configured to sealingly engage with the central portion of the rotatable member.

11. A biopsy device comprising:
    (a) a body;
    (b) a needle extending distally from the body;
    (c) a cutter longitudinally translatable relative to the needle, the cutter defining a cutter lumen; and
    (d) a tissue sample holder including,
        (i) an outer cup,
        (ii) a rotatable member, the rotatable member defining a plurality of outer chambers and an inner chamber,
        (iii) a tissue receiving member including a plurality of trays, each tray of the plurality of trays being insertable into a corresponding outer chamber of the plurality of outer chambers, and
        (iv) an inner cup, the inner cup being insertable into the inner chamber of the rotatable member.

12. The biopsy device of claim 11, the inner cup including a cup body and a filter, the cup body defining a tissue collection chamber.

13. The biopsy device of claim 12, inner cup further including a removable top, at least a portion of the removable top partially defining the tissue collection chamber, the removable top being configured to be selectively removable from the cup body to provide operator access to the tissue collection chamber.

14. The biopsy device of claim 12, the filter being selectively removable from the cup body.

15. The biopsy device of claim 14, the filter including a resilient feature, the resilient feature being configured to selectively secure the filter to the cup body.

16. The biopsy device of claim 12, the filter including a plurality of filter openings, the plurality of filter openings being in communication with the tissue collection chamber, each filter opening of the plurality of filter openings being configured to prevent passage of tissue samples through the filter.

17. The biopsy device of claim 11, the inner cup extending proximally of the rotatable member when the inner cup is inserted in the inner chamber of the rotatable member.

18. The biopsy device of claim 11, the inner cup being disposed entirely within the rotatable member when the inner cup is inserted in the inner chamber of the rotatable member.

19. The biopsy device of claim 11, the rotatable member defining a rotation axis, the plurality of outer chambers, and the inner chamber being coaxial with the rotation axis.

20. The biopsy device of claim 11, the inner cup including a seal, the seal being configured to sealingly engage with the inner chamber of the rotatable member.

* * * * *